(12) United States Patent
Park et al.

(10) Patent No.: US 11,891,445 B1
(45) Date of Patent: Feb. 6, 2024

(54) ANTI-B7-H3 ANTIBODY AND USE THEREOF

(71) Applicant: ABL Bio Inc., Seongnam-si (KR)

(72) Inventors: Kyeongsu Park, Seongnam-si (KR);
Yangsoon Lee, Seongnam-si (KR);
Hyejin Chung, Seongnam-si (KR);
Uijung Jung, Seongnam-si (KR);
Yong-Gyu Son, Seongnam-si (KR);
Sang-Jun Ha, Seongnam-si (KR);
Myeong Joon Kim, Seongnam-si (KR);
Eunyoung Park, Seongnam-si (KR);
Kyungjin Park, Seongnam-si (KR);
Eunsil Sung, Seongnam-si (KR);
Yeunju Kim, Seongnam-si (KR);
Jinhyung Ahn, Seongnam-si (KR);
Byungje Sung, Seongnam-si (KR);
Daehae Song, Seongnam-si (KR);
Youngdon Pak, Seongnam-si (KR)

(73) Assignee: ABL BIO INC., Seongnam-si (KR)

( * ) Notice: Subject to any disclaimer, the term of this patent is extended or adjusted under 35 U.S.C. 154(b) by 326 days.

(21) Appl. No.: 17/057,643

(22) PCT Filed: May 24, 2019

(86) PCT No.: PCT/KR2019/006270
§ 371 (c)(1),
(2) Date: Nov. 20, 2020

(87) PCT Pub. No.: WO2019/226017
PCT Pub. Date: Nov. 28, 2019

(30) Foreign Application Priority Data

May 24, 2018 (KR) .................. 10-2018-0059257
May 25, 2018 (WO) ............... PCT/KR2018/005968

(51) Int. Cl.
C07K 16/28 (2006.01)
G01N 33/574 (2006.01)
A61P 35/00 (2006.01)
A61K 39/00 (2006.01)

(52) U.S. Cl.
CPC .......... *C07K 16/2827* (2013.01); *A61P 35/00* (2018.01); *G01N 33/57492* (2013.01); *A61K 2039/505* (2013.01); *C07K 2317/33* (2013.01); *C07K 2317/565* (2013.01); *C07K 2317/622* (2013.01); *C07K 2317/732* (2013.01); *C07K 2317/76* (2013.01); *C07K 2317/92* (2013.01); *G01N 2333/70532* (2013.01)

(58) Field of Classification Search
CPC ................................................ C07K 16/2827
See application file for complete search history.

(56) References Cited

U.S. PATENT DOCUMENTS

| | | |
|---|---|---|
| 3,773,919 A | 11/1973 | Boswell et al. |
| 4,816,567 A | 3/1989 | Cabilly et al. |
| 4,946,778 A | 8/1990 | Ladner et al. |
| 4,965,195 A | 10/1990 | Namen et al. |
| 4,968,607 A | 11/1990 | Dower et al. |
| 5,011,912 A | 4/1991 | Hopp et al. |
| 5,260,203 A | 11/1993 | Ladner et al. |
| 5,262,522 A | 11/1993 | Gearing |
| 5,426,048 A | 6/1995 | Gearing |
| 5,457,035 A | 10/1995 | Baum et al. |
| 5,530,101 A | 6/1996 | Queen et al. |
| 5,545,806 A | 8/1996 | Lonberg et al. |
| 5,545,807 A | 8/1996 | Surani et al. |
| 5,585,089 A | 12/1996 | Queen et al. |
| 5,693,761 A | 12/1997 | Queen et al. |
| 5,693,762 A | 12/1997 | Queen et al. |
| 5,874,299 A | 2/1999 | Lonberg et al. |
| 5,877,397 A | 3/1999 | Lonberg et al. |
| 6,162,963 A | 12/2000 | Kucherlapati et al. |
| 6,180,370 B1 | 1/2001 | Queen et al. |
| 6,255,458 B1 | 7/2001 | Lonberg et al. |
| 6,270,964 B1 | 8/2001 | Michnick et al. |
| 6,300,129 B1 | 10/2001 | Lonberg et al. |
| 6,673,986 B1 | 1/2004 | Kucherlapati et al. |
| 6,713,610 B1 | 3/2004 | Kucherlapati |
| 8,802,091 B2 | 8/2014 | Johnson et al. |

(Continued)

FOREIGN PATENT DOCUMENTS

| | | |
|---|---|---|
| CN | 101104639 | 1/2008 |
| EP | 036676 | 9/1981 |

(Continued)

OTHER PUBLICATIONS

McCarthy et al., J. Immunol. Methods, 251(1-2): 137-149 (Year: 2001).*
Lin et al. (African Journal of Biotechnology, 10(79):18294-18302) (Year: 2011).*
How to Interpret News About Ways to Prevent Cancer, American Cancer Society, retrieved from: https://www.cancer.org/healthy/cancer-facts/how-to-interpret-news-about-ways-to-prevent-cancer.html (Year: 2021).*

(Continued)

*Primary Examiner* — Adam Weidner
*Assistant Examiner* — Ashley H. Gao
(74) *Attorney, Agent, or Firm* — LEX IP MEISTER, PLLC

(57) ABSTRACT

Provided is an anti-B7-H3 antibody specifically recognizing a B7-H3, which can be usefully as a cancer therapeutic agent, as having an inhibitory activity of an immune checkpoint which induces antibody-dependent cell-mediated cytotoxicity and T cell activation inhibited by B7-H3. In particular, the antibody having the inhibitory activity of an immune checkpoint can be used in combination with other immunoantibody therapeutic agents. In addition, it can be usefully used for cancer targeting treatment including detection of various cancers expressing B7-H3 through specific binding to B7-H3, and drug delivery to specific cancer, etc.

14 Claims, 14 Drawing Sheets

Specification includes a Sequence Listing.

(56) References Cited

U.S. PATENT DOCUMENTS

| | | | |
|---|---|---|---|
| 9,150,656 | B2 | 10/2015 | Johnson et al. |
| 9,371,395 | B2 | 6/2016 | Takahashi et al. |
| 2010/0028370 | A1 | 2/2010 | Zankel et al. |
| 2012/0294796 | A1 | 11/2012 | Johnson et al. |
| 2013/0078234 | A1 | 3/2013 | Takahashi et al. |
| 2017/0355756 | A1* | 12/2017 | Julien ............... A61P 25/00 |
| 2017/0362322 | A1* | 12/2017 | DuBridge ............ C07K 16/30 |

FOREIGN PATENT DOCUMENTS

| | | |
|---|---|---|
| EP | 060846 | 4/1982 |
| EP | 133988 | 3/1985 |
| EP | 058481 | 10/1986 |
| EP | 088046 | 12/1987 |
| EP | 143949 | 10/1988 |
| EP | 0367566 | 5/1990 |
| EP | 546073 | 9/1997 |
| JP | 2013-520994 | 6/2013 |
| KR | 10-2013-0010117 | 1/2013 |
| KR | 10-2014-0033018 | 3/2014 |
| WO | 1990-04036 | 4/1990 |
| WO | 1991-10741 | 7/1991 |
| WO | 1993-15722 | 8/1993 |
| WO | 1994-02602 | 2/1994 |
| WO | 1994-20069 | 9/1994 |
| WO | 1996-33735 | 10/1996 |
| WO | 1999-10494 | 3/1999 |
| WO | 2005-012359 | 2/2005 |
| WO | 2005-035584 | 4/2005 |
| WO | WO-2008068048 A2 * | 6/2008 ............. A61P 31/10 |
| WO | 2008-156712 | 12/2008 |
| WO | 2012-147713 | 11/2012 |
| WO | 2016-033225 | 3/2016 |
| WO | 2016-196298 | 12/2016 |
| WO | 2017-214335 | 12/2017 |

OTHER PUBLICATIONS

Mariuzza, et al., The Structural Basis of Antigen-Antibody Recognition, Ann. Rev. Biophys. Biophys. Chem. 1987. 16: 139-59 (Year: 1987).*

J. M. Adams et al., "The c-myc oncogene driven by immunoglobulin enhancers induces lymphoid malignancy in transgenic mice", 1985, Nature 318:533-538.

Warren S. Alexander et al., "Expression of the c-myc oncogene under control of an immunoglobulin enhancer in E mu-myc transgenic mice", Mol Cell Biol. Apr. 1987; 7(4): 1436-1444.

Ashkenazi et al., "Protection against endotoxic shock by a tumor necrosis factor receptor immunoadhesin", 1991, Proc. Natl. Acad. Sci. USA 88:10535.

Ausubel et al., Current Protocols in Molecular Biology, Greene Publishing Associates, Dec. 4, 2003, ISBN: 047150338X.

Baum et al., "Molecular characterization of murine and human OX40/OX40 ligand systems: identification of a human OX40 ligand as the HTLV-1-regulated protein gp34", 1994, EMBO J. 13:3992-4001.

Benoist and Chambon, "In vivo sequence requirements of the SV40 early promoter region", 1981, Nature 290:304-310.

Allison A. Bianchi, et al., "High-Level Expression of Full-Length Antibodies Using Trans-Complementing Expression Vectors", 2003, Biotech. Biotechnol. Bioeng. 84:439-44.

Robert E. Bird et al., "Single-Chain Antigen-Binding Proteins", 1988, Science 242:423.

James W. Bloom et al., "Intrachain disulfide bond in the core hinge region of human IgG4", 1997, Protein Science 6:407-415.

James U. Bowie et al., "A Method to Identify Protein Sequences That Fold into a Known Three-Dimensional Structure", 1991, Science 253:164-170.

Byrn et al., "Biological properties of a CD4 immunoadhesin", 1990, Nature 344:677.

Carillo et al., "The Multiple Sequence Alignment Problem in Biology*", 1988, SIAM J. Applied Math. 48:1073.

Chalfie et al., "Green Fluorescent Protein as a Marker for Gene Expression", 1994, Science 263:802-805.

Chothia and Lesk, "Canonical Structure for the Hypervariable Regions of Immunoglobulins", J. Mol. Biol. 196:901-917 (1987).

Computer Analysis of Sequence Data, Part I, (Griffin, A. M., and Griffin, H. G., eds.), 1994, New Jersey: Humana Press.

Cosman et al., "Cloning, sequence and expression of human interleukin-2 receptor", 1984, Nature 312:768.

Dayhoff et al., "A Model of Evolutionary Change in Proteins", 1978, Atlas of Protein Sequence and Structure 5:345-352.

Michelle de Graaf et al., "Expression of scFvs and scFv Fusion Proteins in Eukaryotic Cells", 2002, Methods Mol Biol. 178:379-387.

DeBoer et al., "The tac promoter: A functional hybrid derived from the trp and lac promoters", 1983, Proc. Natl. Acad. Sci. U.S.A. 80:21-25.

Devereux et al., "A comprehensive set of sequence analysis programs for the VAX", 1984, Nucl. Acid Res. 12:387.

Eppstein et al., "Biological activity of liposome-encapsulated murine interferon y is mediated by a cell membrane receptor", 1985, Proc. Natl. Acad. Sci. U.S.A. 82:3688-3692.

Evans et al., "Design of Nonpeptidal Ligands for a Peptide Receptor: Cholecystokinin Antagonists", 1987, J. Med. Chem. 30:1229.

William E., Md. Paul, Fundamental Immunology 5th edition (Aug. 2003).

Gribskov et al., "Profile analysis: Detection of distantly related proteins", 1987, Proc. Nat. Acad. Sci. 84:4355-4358.

Grosschedl et al., "Introduction of a p Immunoglobulin Gene into the Mouse Germ Line: Specific Expression in Lymphoid Cells and Synthesis of Functional Antibody", 1984, Cell 38:647-658.

Hammer et al., "Diversity of Aipha-Fetoprotein Gene Expression in Mice is Generated by a Combination of Separate Enhancer Elements", 1987, Science 253:53-58.

Hanahan, "Heritable formation of pancreatic ß-cell tumours in transgenic mice expressing recombinant insulin/simian virus 40 oncogenes", 1985, Nature 315:115-122.

Heim et al., "Engineering green fluorescent protein for improved brightness, longer wavelengths and fluorescence resonance energy transfer", 1996, Curr. Biol. 6:178-182.

Henikoff et al., "Amino acid substitution matrices from protein blocks", 1992, Proc. Natl. Acad. Sci. U.S.A. 89:10915-10919.

Hollenbaugh et al., "Construction of Immunoglobulin Fusion Proteins", in Current Protocols in Immunology, Suppl. 4, pp. 10.19.1-10.19.11.

Holm et al., "Protein folds and families: sequence and structure alignments", 1999, Nucl. Acid. Res. 27:244-247.

Hoogenboom et al., "By-passing immunisation: Human antibodies from synthetic repertoires of germline VH gene segments rearranged in vitro", J. Mol. Biol. 227:381.

Hopp et al., "A Short Polypeptide Marker Sequence Useful for Recombinant Protein Identification and Purification", 1988, Bio/Technology 6:1204.

Huston et al., "Protein engineering of antibody binding sites: Recovery of specific activity in an anti-digoxin single-chain Fv analogue produced in *Escherichia coli*", 1988, Proc. Natl. Acad. Sci. U.S.A. 85:5879.

Hye Young Yang et al., "Construction of a Large Synthetic Human scFv Library with Six Diversified CDRs and High Functional Diversity", Mol. Cells OT, 225-235, Feb. 28, 2009. DOI/10.1007/s10059-009-0028-9.

Ichiki et al., "cells in IL-4-induced human IgE production B cells in IL-4-induced human IgE production", 1993, J. Immunol. 150:5408-5417.

Weng Tao et al., "Encapsulated Cell-Based Delivery of CNTF Reduces Photoreceptor Degeneration in Animal Models of Retinitis Pigmentosa", Invest. Ophthalmol Vis Sci 43:3292-3298, 2002.

Jakobovits et al., "Germ-line transmission and expression of a human-derived yeast artificial chromosome", 1993, Nature 362:255-258.

Jakobovits et al., "Analysis of homozygous mutant chimeric mice: Deletion of the immunoglobulin heavy-chain joining region blocks B-cell development and antibody production", 1993, Proc. Natl. Acad. Sci. USA 90:2551-2555.

(56) References Cited

OTHER PUBLICATIONS

Jalkanen et al., "Intracellular Transport of Phosphatidylcholine to the Plasma Membrane", 1985, J. Cell. Biol. 101:976-985.
Jalkanen et al., "Cell Surface Proteoglycan of Mouse Mammary Epithelial Cells Is Shed by Cleavage of Its Matrix-binding Ectodomain from Its Membrane-associated Domain", 1987, J. Cell Biol. 105:3087-3096.
Jones, "Progress in protein structure prediction", Curr. Opin. Struct. Biol. 1997, 7:377-387.
Kelsey et al., "Species-and tissue-specific expression of human alpha 1-antitrypsin in transgenic mice.", 1987, Genes and Devel. 1:161-171.
Kohler and Milstein, "Continuous cultures of fused cells secreting antibody of predefined specificity", 1975, Nature 256:495.
Kollias et al., "Regulated expression of human Aγ-, β-, and hybrid γβ-globin genes in transgenic mice: Manipulation of the developmental expression patterns", 1986, Cell 46:89-94.
Kortt et al., "Single-chain Fv fragments of anti-neuraminidase antibody NC10 containing five—and ten-residue linkers form dimers and with zero-residue linker a trimer", 1997, Prot. Eng. 10:423.
Kortt et al., "Dimeric and trimeric antibodies: high avidity scFvs for cancer targeting", 2001, Biomol. Eng. 18:95-108.
Kostelny et al., "Formation of a Bispecific Antibody By the Use of Leucine Zippers", 1992, J. Immunol. 148:1547-1553.
Kriangkum et al., "Bispecific and bifunctional single chain recombinant antibodies", 2001, Biomol. Eng. 18:31-40.
Krumlauf et al., "Developmental regulation of alpha-fetoprotein genes in transgenic mice", 1985, Mol. Cell. Biol. 5:1639-1648.
Deryk Loo et al., "Development of an Fc-enhanced anti-B7-H3 monoclonal antibody with potent antitumor activity", Clinical Cancer Research, vol. 18, No. 14, Jul. 15, 2012 (Jul. 15, 2012), , pp. 3834-3845, XP055092714, ISSN: 1078-0432, DOI: 10.1158/1078-0432.CCR-12-0715.
EPO, search report of EP 19807093.0 dated Feb. 22, 2022.
JPO, Office Action of JP 2020-564922 dated Feb. 15, 2022.
Andrei I. Chapoval et al., "B7-H3:A costimulatory molecule for T cell activation and IFN-βproduction", nature immunology 2001; vol. 2 No.3 269-74, Mar. 2001.
Yih-Wen Chen et al., "The Immunoregulatory Protein Human B7H3 is a Tumor-Associated Antigen that Regulates Tumor Cell Migration and Invasion", Current Cancer Drug Targets, 2008, vol. 8, No. 5. pp. 404-413, Aug. 2008.
Elodie Picarda et al., "Molecular Pathways: Targeting B7-H3 (CD276) for Human Cancer Immunotherapy", clinical cancer research Jul. 15, 2016; 22(14): 3425-3431. doi:10.1158/1078-0432.CCR-15-2428.
Martin Loos et al. "Expression of the costimulatory molecule B7-H3 is associated with prolonged survival in human pancreatic cancer" BMC Cancer, vol. 9, article 463, Dec. 26, 2009.
Hye Young Yang et al., "Construction of a Large Synthetic Human scFv Library with Six Diversified CDRs and High Functional Diversity", Mol. Cells 27, 225-235, Feb. 28, 2009.
Drew M. Pardoll. "The blockade of immune checkpoints in cancer immunotherapy", Nature Reviews Cancer vol. 12, pp. 252-264, Apr. 2012.
Wei Zhang et al., "B7-H3 silencing inhibits tumor progression of mantle cell lymphoma and enhances chemosensitivity", International journal of oncology 2015;46(6):2562-72, Apr. 2015.
Zhimeng Ye et al., B7-H3 Overexpression Predicts Poor Survival of Cancer Patients: A Meta-Analysis, Cellular Physiology and Biochemistry 2016;39:1568-1580, Published online: Sep. 15, 2016.
Kipo, PCT Search Report & Written Opinion of PCT/KR2019/006270, dated Aug. 26, 2019.
Ruhong Yan et al., "A Novel Monoclonal Antibody Against Mouse B7-H3 Developed in Rats", HYBRIDOMA vol. 31, No. 4, 2012, pp. 267-271, Aug. 2012.
Young-hee Lee et al., "Inhibition of the B7-H3 immune checkpoint limits tumor growth by enhancing cytotoxic lymphocyte function", Cell Research, 2017, vol. 27, pp. 1034-1045, published online Jul. 7, 2017.
Kipo, PCT Search Report & Written Opinion of PCT/KR2018/005968, dated Feb. 22, 2019.
Zheng-Rong Chen et al., "Therapeutic effects of antieB7-H3 antibody in an ovalbumin-induced mouse asthma model". Annals of allergy, asthma & immunology 111(4), pp. 276-281, Oct. 2013.
Kyte et al., "A Simple Method for Displaying the Hydropathic Character of a Protein", 1982, J. Mol. Biol. 157:105-131.
Langer et al., 1981, "Biocompatibility of polymeric delivery systems for macromolecules", J. Biomed. Mater. Res. 15:167-277.
Lantto et al., "Chain Shuffling to Modify Properties of Recombinant Immunoglobulins", 2002, Methods Mol. Biol. 178:303-316.
Leder et al., "Consequences of Widespread Deregulation the c-myc Gene in Transgenic Mice: Multiple Neoplasms and Normal Development", 1986, Cell 45:485-495.
MacDonald, "Expression of the Pancreatic Elastase I Gene in Transgenic Mice", 1987, Hepatology 7:425-515.
Maniatis et al., "Regulation of Inducible and Tissue-Specific Gene Expression", 1987, Science 236:1237.
Marks et al., "By-passing Immunization Human Antibodies from V-gene Libraries Displayed on Phage", 1991, J.Mol. Bio. 222:581-597.
Marks et al., "By-Passing Immunization: Building High Afffinity Human Antibodies By Chain Shuffling", 1992, BioTechnology 10:779-783.
Mason et al., "The Hypogonadal Mouse: Reproductive Functions Restored by Gene Therapy", 1986, Science 234:1372-1378.
Mogram et al., "Developmental regulation of a cloned adult γ-globin gene in transgenic mice", 1985, Nature 315:338-340.
Morrison et al., "Chimeric human antibody molecules: Mouse antigen-binding domains with human constant region domains", 1985, Proc. Natl. Acad. Sci. USA 81:6851-6855.
Needleman et al., "A General Method Applicable to the Search for Similarities in the Amino Acid Sequence of Two Proteins", 1970, J. Mol. Biol. 48:443-453.
Nolan et al., "Fluorescence-activated cell analysis and sorting of viable mammalian cells based on beta-D-galactosidase activity after transduction of *Escherichia coli* lacZ.", 1988, Proc. Natl. Acad. Sci. U.S.A. 85:2603-2607.
Pinkert et al., "An albumin enhancer located 10 kb upstream functions along with its promoter to direct efficient, liver-specific expression in transgenic mice", 1987, Genes and Devel. 1:268-276.
Prinster et al., "Regulation of metallothionein-thymidine kinase fusion plasmids injected into mouse eggs", 1982, Nature 296:39-42.
Paul A. Sieving et al., "Ciliary neurotrophic factor (CNTF) for human retinal degeneration: Phase I trial of CNTF delivered by encapsulated cell intraocular implants", Proc. Natl. Acad. Sciences 103:3896-3901, 2006.
T E Creighton, "Proteins, Structures and Molecular Principles", 1984, W. H. New York: Freeman and Company.
Readhead et al., "Expression of a Myelin Basic Protein Gene in Transgenic Shiverer Mice: Correction of the Dysmyelinating Phenotype", 1987, Cell 48:703-712.
Rizo and Gierasch, "Constrained Peptides: Models of Bioactive Peptides and Protein Substructures", 1992, Ann. Rev. Biochem. 61:387.
Russell et al., "Structural Features can be Unconserved in Proteins with Smilar Folds", J. Mol Biol., 244: 332-350 (1994).
Sambrook et al., Molecular Cloning: A Laboratory Manual, 4th ed., Cold Spring Harbor Laboratory Press, Cold Spring Harbor, N.Y. (2012).
Shani, "Tissue-specific expression of rat myosin light-chain 2 gene in transgenic mice", 1985, Nature 314:283-286.
Gribskov, M. and Devereux, J., Sequence Analysis Primer, 1991, New York: M. Stockton Press.
Sidman et al., "Controlled Release of Macromolecules and Pharmaceuticals from Synthetic Polypeptides Based on Glutamic Acid", 1983, Biopolymers 2:547-556.
Sippl et al., "Threading thrills and threats", 1996, Structure 4:15-19.
Songsivilai and Lachmann, "Bispecific antibody: a tool for diagnosis and treatment of disease", 1990, Clin. Exp. Immunol. 79:315-321.
Stauber, "Development and Applications of Enhanced Green Fluorescent Protein Mutants", 1998 Biotechniques 24:462-471.

(56) References Cited

OTHER PUBLICATIONS

Swift et al., "Tissue-Specific Expression of the Rat Pancreatic Elastase I Gene in Transgenic Mice", 1984, Cell 38:639-646.

Thornsen et al., "Promoter-regulatory region of the major immediate early gene of human cytomegalovirus", 1984, Proc. Natl. Acad. U.S.A. 81:659-663.

Thornton et al., "Prediction of progress at last", 1991, Nature 354:105.

Veber and Freidinger, "The design of metalbolically-stable peptide analogs", 1985, TINS p. 392.

Villa-Kamaroff et al., "A bacterial clone synthesizing proinsulin", 1978, Proc. Natl. Acad. Sci. U.S.A. 75:3727-3731.

Voss et al., "The role of enhancers in the regulation of cell-type-specific transcriptional control", 1986, Trends Biochem. Sci. 11:287.

Wagner et al., "Nucleotide sequence of the thymidine kinase gene of herpes simplex virus type 1", 1981, Proc. Natl. Acad. Sci. U.S.A. 78:1444-1445.

Ward et al., "Binding activities of a repertoire of single immunoglobulin variable domains secreted from *Escherichia coli*", 1989, Nature 334:544.

Yamamoto et al., "Identification of a Functional Promoter in the Long Terminal Repeat of Rous Sarcoma Virus", 1980, Cell 22:787-797.

\* cited by examiner

SEQUENCE LISTING

<160> NUMBER OF SEQ ID NOS: 75

<210> SEQ ID NO 1
<211> LENGTH: 5
<212> TYPE: PRT
<213> ORGANISM: Artificial Sequence
<220> FEATURE:
<223> OTHER INFORMATION: Synthetic: Heavy cahin CDR1

<400> SEQUENCE: 1

Asp Tyr Ala Met Ser
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic: Heavy cahin CDR1

<400> SEQUENCE: 2

Gly Tyr Tyr Met Ser
1               5

<210> SEQ ID NO 3
<211> LENGTH: 5

```
<212> TYPE: PRT
<213> ORGANISM: Artificial Sequence
<220> FEATURE:
<223> OTHER INFORMATION: Synthetic: Heavy cahin CDR1

<400> SEQUENCE: 3

Ser Tyr Ser Met Ser
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic: Heavy cahin CDR1

<400> SEQUENCE: 4

Ser Tyr Gly Met Ser
1               5

<210> SEQ ID NO 5
<211> LENGTH: 17
<212> TYPE: PRT
<213> ORGANISM: Artificial Sequence
<220> FEATURE:
<223> OTHER INFORMATION: Synthetic: Heavy cahin CDR2

<400> SEQUENCE: 5

Ser Ile Ser Ser Gly Ser Gly Ser Ile Tyr Tyr Ala Asp Ser Val Lys
1               5                   10                  15

Gly

<210> SEQ ID NO 6
<211> LENGTH: 17
<212> TYPE: PRT
<213> ORGANISM: Artificial Sequence
<220> FEATURE:
<223> OTHER INFORMATION: Synthetic: Heavy cahin CDR2

<400> SEQUENCE: 6

Leu Ile Ser Pro Ser Ser Gly Ser Ile Tyr Tyr Ala Asp Ser Val Lys
1               5                   10                  15

Gly

<210> SEQ ID NO 7
<211> LENGTH: 17
<212> TYPE: PRT
<213> ORGANISM: Artificial Sequence
<220> FEATURE:
<223> OTHER INFORMATION: Synthetic: Heavy cahin CDR2

<400> SEQUENCE: 7

Gly Ile Tyr Ser Asp Gly Ser Asn Thr Tyr Tyr Ala Asp Ser Val Lys
1               5                   10                  15

Gly

<210> SEQ ID NO 8
<211> LENGTH: 17
<212> TYPE: PRT
<213> ORGANISM: Artificial Sequence
<220> FEATURE:
<223> OTHER INFORMATION: Synthetic: Heavy cahin CDR2

<400> SEQUENCE: 8

Gly Ile Ser Pro Gly Gly Ser Asn Thr Tyr Tyr Ala Asp Ser Val Lys
```

-continued

```
1               5                   10                  15

Gly

<210> SEQ ID NO 9
<211> LENGTH: 17
<212> TYPE: PRT
<213> ORGANISM: Artificial Sequence
<220> FEATURE:
<223> OTHER INFORMATION: Synthetic: Heavy cahin CDR2

<400> SEQUENCE: 9

Gly Ile Tyr Ser Gly Gly Ser Ser Lys Tyr Tyr Ala Asp Ser Val Lys
1               5                   10                  15

Gly

<210> SEQ ID NO 10
<211> LENGTH: 7
<212> TYPE: PRT
<213> ORGANISM: Artificial Sequence
<220> FEATURE:
<223> OTHER INFORMATION: Synthetic: Heavy cahin CDR3

<400> SEQUENCE: 10

Asn Leu Ile Pro Leu Asp Tyr
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic: Heavy cahin CDR3

<400> SEQUENCE: 11

Gly Leu Thr Lys Phe Asp Tyr
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic: Heavy cahin CDR3

<400> SEQUENCE: 12

Met Leu His Arg Phe Asp Tyr
1               5

<210> SEQ ID NO 13
<211> LENGTH: 12
<212> TYPE: PRT
<213> ORGANISM: Artificial Sequence
<220> FEATURE:
<223> OTHER INFORMATION: Synthetic: Heavy cahin CDR3

<400> SEQUENCE: 13

Asp Ala Trp Ile Ala Arg Leu Leu Leu Phe Asp Tyr
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Synthetic: Heavy cahin CDR3
```

```
<400> SEQUENCE: 14

Asn Arg Leu Arg Phe Asp Tyr
1               5

<210> SEQ ID NO 15
<211> LENGTH: 13
<212> TYPE: PRT
<213> ORGANISM: Artificial Sequence
<220> FEATURE:
<223> OTHER INFORMATION: Synthetic: Light cahin CDR1

<400> SEQUENCE: 15

Ser Gly Ser Ser Ser Asn Ile Gly Ser Asn Ala Val Ser
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Synthetic: Light cahin CDR1

<400> SEQUENCE: 16

Thr Gly Ser Ser Ser Asn Ile Gly Ser Asn Asp Val Ser
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Synthetic: Light cahin CDR1

<400> SEQUENCE: 17

Ser Gly Ser Ser Ser Asn Ile Gly Ser Asn Ser Val Thr
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Synthetic: Light cahin CDR1

<400> SEQUENCE: 18

Ser Gly Ser Ser Ser Asn Ile Gly Ser Asn Ala Val Thr
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Synthetic: Light cahin CDR1

<400> SEQUENCE: 19

Thr Gly Ser Ser Ser Asn Ile Gly Ser Asn Ser Val Thr
1               5                   10

<210> SEQ ID NO 20
<211> LENGTH: 7
<212> TYPE: PRT
<213> ORGANISM: Artificial Sequence
<220> FEATURE:
<223> OTHER INFORMATION: Synthetic: Light cahin CDR2

<400> SEQUENCE: 20
```

```
Tyr Asn Ser His Arg Pro Ser
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic: Light cahin CDR2

<400> SEQUENCE: 21

Ala Asn Ser His Arg Pro Ser
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic: Light cahin CDR2

<400> SEQUENCE: 22

Ala Asp Ser Gln Arg Pro Ser
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic: Light cahin CDR2

<400> SEQUENCE: 23

Tyr Asn Asn Lys Arg Pro Ser
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic: Light cahin CDR2

<400> SEQUENCE: 24

Ser Asp Ser His Arg Pro Ser
1               5

<210> SEQ ID NO 25
<211> LENGTH: 11
<212> TYPE: PRT
<213> ORGANISM: Artificial Sequence
<220> FEATURE:
<223> OTHER INFORMATION: Synthetic: Light cahin CDR3

<400> SEQUENCE: 25

Gly Ser Trp Asp Ala Ser Leu Asn Ala Tyr Val
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Synthetic: Light cahin CDR3

<400> SEQUENCE: 26
```

```
Gly Ser Trp Asp Asp Ser Leu Ser Gly Tyr Val
1               5                   10
```

<210> SEQ ID NO 27
<211> LENGTH: 11
<212> TYPE: PRT
<213> ORGANISM: Artificial Sequence
<220> FEATURE:
<223> OTHER INFORMATION: Synthetic: Light cahin CDR3

<400> SEQUENCE: 27

```
Gly Thr Trp Asp Ser Ser Leu Asn Ala Tyr Val
1               5                   10
```

<210> SEQ ID NO 28
<211> LENGTH: 11
<212> TYPE: PRT
<213> ORGANISM: Artificial Sequence
<220> FEATURE:
<223> OTHER INFORMATION: Synthetic: Light cahin CDR3

<400> SEQUENCE: 28

```
Gly Thr Trp Asp Asp Ser Leu Ser Gly Tyr Val
1               5                   10
```

<210> SEQ ID NO 29
<211> LENGTH: 11
<212> TYPE: PRT
<213> ORGANISM: Artificial Sequence
<220> FEATURE:
<223> OTHER INFORMATION: Synthetic: Light cahin CDR3

<400> SEQUENCE: 29

```
Gly Thr Trp Asp Ala Ser Leu Asn Ala Tyr Val
1               5                   10
```

<210> SEQ ID NO 30
<211> LENGTH: 116
<212> TYPE: PRT
<213> ORGANISM: Artificial Sequence
<220> FEATURE:
<223> OTHER INFORMATION: Synthetic: Heavy chain variable region

<400> SEQUENCE: 30

```
Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Ser Ile Ser Ser Gly Ser Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Leu Ile Pro Leu Asp Tyr Trp Gly Gln Gly Thr Leu Val
            100                 105                 110

Thr Val Ser Ser
        115
```

<210> SEQ ID NO 31
<211> LENGTH: 116

-continued

```
<212> TYPE: PRT
<213> ORGANISM: Artificial Sequence
<220> FEATURE:
<223> OTHER INFORMATION: Synthetic: Heavy chain variable region

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Tyr Met Ser Trp Val Arg Gln Ala Pro Gly Lys Gly Leu Glu Trp Val
        35                  40                  45

Ser Leu Ile Ser Pro Ser Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Leu Thr Lys Phe Asp Tyr Trp Gly Gln Gly Thr Leu Val
            100                 105                 110

Thr Val Ser Ser
        115

<210> SEQ ID NO 32
<211> LENGTH: 116
<212> TYPE: PRT
<213> ORGANISM: Artificial Sequence
<220> FEATURE:
<223> OTHER INFORMATION: Synthetic: Heavy chain variable region

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45

Ser Gly Ile Tyr Ser Asp Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Met Leu His Arg Phe Asp Tyr Trp Gly Gln Gly Thr Leu Val
            100                 105                 110

Thr Val Ser Ser
        115

<210> SEQ ID NO 33
<211> LENGTH: 121
<212> TYPE: PRT
<213> ORGANISM: Artificial Sequence
<220> FEATURE:
<223> OTHER INFORMATION: Synthetic: Heavy chain variable region

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
```

```
                 20                  25                  30
Ala Met Ser Trp Val Arg Gln Ala Pro Gly Lys Gly Leu Glu Trp Val
             35                  40                  45

Ser Gly Ile Ser Pro Gly Gly Ser Asn Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ala Trp Ile Ala Arg Leu Leu Phe Asp Tyr Trp Gly
            100                 105                 110

Gln Gly Thr Leu Val Thr Val Ser Ser
            115                 120

<210> SEQ ID NO 34
<211> LENGTH: 116
<212> TYPE: PRT
<213> ORGANISM: Artificial Sequence
<220> FEATURE:
<223> OTHER INFORMATION: Synthetic: Heavy chain variable region

<400> SEQUENCE: 34

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Gly Met Ser Trp Val Arg Gln Ala Pro Gly Lys Gly Leu Glu Trp Val
             35                  40                  45

Ser Gly Ile Tyr Ser Gly Gly Ser Ser Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asn Arg Leu Arg Phe Asp Tyr Trp Gly Gln Gly Thr Leu Val
            100                 105                 110

Thr Val Ser Ser
        115

<210> SEQ ID NO 35
<211> LENGTH: 111
<212> TYPE: PRT
<213> ORGANISM: Artificial Sequence
<220> FEATURE:
<223> OTHER INFORMATION: Synthetic: Light chain variable region

<400> SEQUENCE: 35

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Asn Ile Gly Ser Asn
                 20                  25                  30

Ala Val Ser Trp Tyr Gln Gln Leu Pro Gly Thr Ala Pro Lys Leu Leu
             35                  40                  45

Ile Tyr Tyr Asn Ser His Arg Pro Ser Gly Val Pro Asp Arg Phe Ser
         50                  55                  60

Gly Ser Lys Ser Gly Thr Ser Ala Ser Leu Ala Ile Ser Gly Leu Arg
 65                  70                  75                  80
```

Ser Glu Asp Glu Ala Asp Tyr Tyr Cys Gly Ser Trp Asp Ala Ser Leu
            85                  90                  95

Asn Ala Tyr Val Phe Gly Gly Gly Thr Lys Leu Thr Val Leu Gly
            100                 105                 110

<210> SEQ ID NO 36
<211> LENGTH: 111
<212> TYPE: PRT
<213> ORGANISM: Artificial Sequence
<220> FEATURE:
<223> OTHER INFORMATION: Synthetic: Light chain variable region

<400> SEQUENCE: 36

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30

Asp Val Ser Trp Tyr Gln Gln Leu Pro Gly Thr Ala Pro Lys Leu Leu
        35                  40                  45

Ile Tyr Ala Asn Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Asp Ser Leu
            85                  90                  95

Ser Gly Tyr Val Phe Gly Gly Gly Thr Lys Leu Thr Val Leu Gly
            100                 105                 110

<210> SEQ ID NO 37
<211> LENGTH: 111
<212> TYPE: PRT
<213> ORGANISM: Artificial Sequence
<220> FEATURE:
<223> OTHER INFORMATION: Synthetic: Light chain variable region

<400> SEQUENCE: 37

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Ser Val Thr Trp Tyr Gln Gln Leu Pro Gly Thr Ala Pro Lys Leu Leu
        35                  40                  45

Ile Tyr Ala Asp Ser Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Ser Ser Leu
            85                  90                  95

Asn Ala Tyr Val Phe Gly Gly Gly Thr Lys Leu Thr Val Leu Gly
            100                 105                 110

<210> SEQ ID NO 38
<211> LENGTH: 111
<212> TYPE: PRT
<213> ORGANISM: Artificial Sequence
<220> FEATURE:
<223> OTHER INFORMATION: Synthetic: Light chain variable region

<400> SEQUENCE: 38

Gln Ser Val Leu Thr Gln Pro Pro Ser Ala Ser Gly Thr Pro Gly Gln

```
 1               5                   10                  15
Arg Val Thr Ile Ser Cys Ser Gly Ser Ser Asn Ile Gly Ser Asn
                20                  25                  30

Ala Val Thr Trp Tyr Gln Gln Leu Pro Gly Thr Ala Pro Lys Leu Leu
                35                  40                  45

Ile Tyr Tyr Asn Asn Lys Arg Pro Ser Gly Val Pro Asp Arg Phe Ser
        50                  55                  60

Gly Ser Lys Ser Gly Thr Ser Ala Ser Leu Ala Ile Ser Gly Leu Arg
 65                 70                  75                  80

Ser Glu Asp Glu Ala Asp Tyr Tyr Cys Gly Thr Trp Asp Asp Ser Leu
                85                  90                  95

Ser Gly Tyr Val Phe Gly Gly Gly Thr Lys Leu Thr Val Leu Gly
                100                 105                 110
```

<210> SEQ ID NO 39
<211> LENGTH: 111
<212> TYPE: PRT
<213> ORGANISM: Artificial Sequence
<220> FEATURE:
<223> OTHER INFORMATION: Synthetic: Light chain variable region

<400> SEQUENCE: 39

```
Gln Ser Val Leu Thr Gln Pro Pro Ser Ala Ser Gly Thr Pro Gly Gln
 1               5                   10                  15

Arg Val Thr Ile Ser Cys Thr Gly Ser Ser Asn Ile Gly Ser Asn
                20                  25                  30

Ser Val Thr Trp Tyr Gln Gln Leu Pro Gly Thr Ala Pro Lys Leu Leu
                35                  40                  45

Ile Tyr Ser Asp Ser His Arg Pro Ser Gly Val Pro Asp Arg Phe Ser
        50                  55                  60

Gly Ser Lys Ser Gly Thr Ser Ala Ser Leu Ala Ile Ser Gly Leu Arg
 65                 70                  75                  80

Ser Glu Asp Glu Ala Asp Tyr Tyr Cys Gly Thr Trp Asp Ala Ser Leu
                85                  90                  95

Asn Ala Tyr Val Phe Gly Gly Gly Thr Lys Leu Thr Val Leu Gly
                100                 105                 110
```

<210> SEQ ID NO 40
<211> LENGTH: 446
<212> TYPE: PRT
<213> ORGANISM: Artificial Sequence
<220> FEATURE:
<223> OTHER INFORMATION: Synthetic: Heavy chain (full-length)

<400> SEQUENCE: 40

```
Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Asp Tyr
                20                  25                  30

Ala Met Ser Trp Val Arg Gln Ala Pro Gly Lys Gly Leu Glu Trp Val
                35                  40                  45

Ser Ser Ile Ser Ser Gly Ser Gly Ser Ile Tyr Tyr Ala Asp Ser Val
        50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95
```

Ala Lys Asn Leu Ile Pro Leu Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 41
<211> LENGTH: 446
<212> TYPE: PRT
<213> ORGANISM: Artificial Sequence
<220> FEATURE:
<223> OTHER INFORMATION: Synthetic: Heavy chain (full-length)

<400> SEQUENCE: 41

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Ser Gly Tyr
            20                  25                  30

Tyr Met Ser Trp Val Arg Gln Ala Pro Gly Lys Gly Leu Glu Trp Val
        35                  40                  45

Ser Leu Ile Ser Pro Ser Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Leu Thr Lys Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
```

-continued

```
            435                 440                 445
```

<210> SEQ ID NO 42
<211> LENGTH: 446
<212> TYPE: PRT
<213> ORGANISM: Artificial Sequence
<220> FEATURE:
<223> OTHER INFORMATION: Synthetic: Heavy chain (full-length)

<400> SEQUENCE: 42

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45

Ser Gly Ile Tyr Ser Asp Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Met Leu His Arg Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
```

```
            355                 360                 365
Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
            435                 440                 445

<210> SEQ ID NO 43
<211> LENGTH: 451
<212> TYPE: PRT
<213> ORGANISM: Artificial Sequence
<220> FEATURE:
<223> OTHER INFORMATION: Synthetic: Heavy chain (full-length)

<400> SEQUENCE: 43

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Gly Ile Ser Pro Gly Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ala Trp Ile Ala Arg Leu Leu Leu Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
```

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 44
<211> LENGTH: 446
<212> TYPE: PRT
<213> ORGANISM: Artificial Sequence
<220> FEATURE:
<223> OTHER INFORMATION: Synthetic: Heavy chain (full-length)

<400> SEQUENCE: 44

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ser Gly Ile Tyr Ser Gly Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Arg Leu Arg Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu

```
                    180                 185                 190
Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
            210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 45
<211> LENGTH: 216
<212> TYPE: PRT
<213> ORGANISM: Artificial Sequence
<220> FEATURE:
<223> OTHER INFORMATION: Synthetic: Light chain (full-length)

<400> SEQUENCE: 45

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Ala Val Ser Trp Tyr Gln Gln Leu Pro Gly Thr Ala Pro Lys Leu Leu
        35                  40                  45

Ile Tyr Tyr Asn Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Ala Ser Leu
                85                  90                  95

Asn Ala Tyr Val Phe Gly Gly Gly Thr Lys Leu Thr Val Leu Gly Gln
```

```
                    100                 105                 110
Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Ala Glu Cys Ser
    210                 215

<210> SEQ ID NO 46
<211> LENGTH: 216
<212> TYPE: PRT
<213> ORGANISM: Artificial Sequence
<220> FEATURE:
<223> OTHER INFORMATION: Synthetic: Light chain (full-length)

<400> SEQUENCE: 46

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30

Asp Val Ser Trp Tyr Gln Gln Leu Pro Gly Thr Ala Pro Lys Leu Leu
        35                  40                  45

Ile Tyr Ala Asn Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Asp Ser Leu
                85                  90                  95

Ser Gly Tyr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Ala Glu Cys Ser
    210                 215

<210> SEQ ID NO 47
<211> LENGTH: 216
<212> TYPE: PRT
```

<213> ORGANISM: Artificial Sequence
<220> FEATURE:
<223> OTHER INFORMATION: Synthetic: Light chain (full-length)

<400> SEQUENCE: 47

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Ser Val Thr Trp Tyr Gln Gln Leu Pro Gly Thr Ala Pro Lys Leu Leu
            35                  40                  45

Ile Tyr Ala Asp Ser Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Ser Ser Leu
                85                  90                  95

Asn Ala Tyr Val Phe Gly Gly Gly Thr Lys Leu Thr Val Leu Gly Gln
                100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Ala Glu Cys Ser
        210                 215
```

<210> SEQ ID NO 48
<211> LENGTH: 216
<212> TYPE: PRT
<213> ORGANISM: Artificial Sequence
<220> FEATURE:
<223> OTHER INFORMATION: Synthetic: Light chain (full-length)

<400> SEQUENCE: 48

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Ala Val Thr Trp Tyr Gln Gln Leu Pro Gly Thr Ala Pro Lys Leu Leu
            35                  40                  45

Ile Tyr Tyr Asn Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Ser Ser Leu
                85                  90                  95

Ser Gly Tyr Val Phe Gly Gly Gly Thr Lys Leu Thr Val Leu Gly Gln
                100                 105                 110
```

```
Pro Lys Ala Ala Pro Ser Val Thr Leu Phe Pro Ser Ser Glu Glu
            115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Ala Glu Cys Ser
    210                 215

<210> SEQ ID NO 49
<211> LENGTH: 216
<212> TYPE: PRT
<213> ORGANISM: Artificial Sequence
<220> FEATURE:
<223> OTHER INFORMATION: Synthetic: Light chain (full-length)

<400> SEQUENCE: 49

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ser Asn
            20                  25                  30

Ser Val Thr Trp Tyr Gln Gln Leu Pro Gly Thr Ala Pro Lys Leu Leu
            35                  40                  45

Ile Tyr Ser Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Ala Ser Leu
                85                  90                  95

Asn Ala Tyr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Ala Glu Cys Ser
    210                 215

<210> SEQ ID NO 50
<211> LENGTH: 1338
<212> TYPE: DNA
<213> ORGANISM: Artificial Sequence
<220> FEATURE:
```

<223> OTHER INFORMATION: Synthetic: Heavy chain (full-length) coding
       gene

<400> SEQUENCE: 50

```
gaagttcagc tgttggaatc tggcggcgga ttggttcagc ctggcggatc tctgagactg    60
tcttgtgccg cctctggctt caccttctcc gactacgcta tgtcctgggt ccgacaggct   120
cctggcaaag gactggaatg ggtgtcctcc atctcttccg gctccggctc tatctactac   180
gccgactctg tgaagggcag attcaccatc agccgggaca ctccaagaa  caccctgtac   240
ctgcagatga actccctgag agccgaggac accgccgtgt actactgcgc caagaatctg   300
atccctctgg actattgggg ccagggcaca ctggttaccg tgtcctctgc ttctaccaag   360
ggacccctctg tgttccctct ggctccttcc agcaagtcta cctctggtgg aaccgctgct   420
ctgggctgcc tggtcaagga ttactttcct gagcctgtga ccgtgtcttg aactccggt    480
gctctgacat ctggcgtgca cacctttcca gctgtgctgc agtcctctgg cctgtactct   540
ctgtcctctg tcgtgaccgt gccttctagc tctctgggca cccagaccta catctgcaac   600
gtgaaccaca gccttccaa  caccaaggtg acaagaagg tggaacccaa gtcctgcgac   660
aagacccaca cctgtccacc atgtcctgct ccagaactgc tcggcggtcc ctccgttttc   720
ctgtttccac ctaagcctaa ggacaccctg atgatctctc ggaccccctga agtgacctgc   780
gtggtggtgg atgtgtctca cgaggatccc gaagtgaagt tcaattggta cgtggacggc   840
gtggaagtgc acaacgccaa gaccaagcct agagaggaac agtacaactc cacctacaga   900
gtggtgtccg tgctgaccgt gctgcaccag gattggctga  cggcaaaga gtacaagtgc   960
aaggtgtcca caaggccct gcctgctcct atcgaaaaga ccatctccaa ggctaagggc  1020
cagcctcggg aacctcaagt gtacaccttg ccaccttcca gagaagagat gaccaagaac  1080
caggtgtccc tgacctgcct cgtgaaggc ttctacccctt ccgatatcgc cgtggaatgg  1140
gagtctaacg gccagccaga gaacaactac aagacaaccc ctcctgtgct ggactccgac  1200
ggctcattct tcctgtactc caagctgaca gtggacaagt ctcggtggca gcagggcaac  1260
gtgttctcct gttctgtgat gcacgaggcc ctgcacaacc actacaccca gaagtccctg  1320
tctctgtccc ctggcaaa                                                1338
```

<210> SEQ ID NO 51
<211> LENGTH: 1338
<212> TYPE: DNA
<213> ORGANISM: Artificial Sequence
<220> FEATURE:
<223> OTHER INFORMATION: Synthetic: Heavy chain (full-length) coding
       gene

<400> SEQUENCE: 51

```
gaagtccaac tcctggagtc cggtggtggt ctcgttcaac ccggaggtag tctccgtctg    60
agttgtgcag cttctggttt caccttttca ggttactata tgtcctgggt acgccaggca   120
cctggaaaag gcttggaatg ggtctcccctt attagtccaa gcagtggtag tatttactac   180
gctgactctg taaaaggtcg tttcactatt tcaagagaca caagcaagaa cacactttac   240
ttgcaaatga atagcctgag ggccgaagac accgccgtct attactgtgc caaaggcttg   300
acaaaatttg attactgggg acaaggtaca ttggtgactg ttagctcagc ctccaccaag   360
ggccccctccg tgttccccct ggccccctcc tccaagtcca cctccggcgg caccgccgcc   420
ctgggctgcc tggtgaagga ctacttcccc gagcccgtga ccgtgtcctg aactccggc    480
gccctgacct ccggcgtgca caccttcccc gccgtgctgc agtcctccgg cctgtactcc   540
```

```
ctgtcctccg tcgtgaccgt gccctcctcc tccctgggca cccagaccta catctgcaac    600
gtgaaccaca agccctccaa caccaaggtg acaagaagg tggagcccaa gtcctgcgac     660
aagacccaca cctgccctcc ctgccccgcc cccgagctgc tgggcggccc ctccgtgttc    720
ctgttccctc ctaagcccaa ggacaccctg atgatctccc ggaccccga ggtgacttgc     780 gtggtggtgg acgtgtccca cgaggacccc gaggtgaagt tcaactggta cgtggacggc    840
gtggaggtgc acaacgccaa gaccaagccc cgggaggagc agtacaactc cacctaccgg    900
gtggtgtccg tgctgaccgt gctgcaccag gactggctga acggcaagga gtacaagtgc    960
aaggtgtcca acaaggccct gcccgccccc atcgagaaga ccatctccaa ggccaagggc   1020
cagccccggg agccccaggt gtacaccctg ccccctccc gggaggagat gaccaagaac    1080
caggtgtccc tgacctgcct ggtgaagggc ttctaccct ccgacatcgc cgtggagtgg     1140
gagtccaacg gccagcccga gaacaactac aagaccaccc ccccgtgct ggactccgac    1200 ggctccttct cctgtactc caagctgacc gtggacaagt cccggtggca gcagggcaac    1260
gtgttctcct gctccgtgat gcacgaggcc ctgcacaacc actacaccca gaagtccctg    1320
tccctgtccc ccggcaag                                                  1338
```

<210> SEQ ID NO 52
<211> LENGTH: 1338
<212> TYPE: DNA
<213> ORGANISM: Artificial Sequence
<220> FEATURE:
<223> OTHER INFORMATION: Synthetic: Heavy chain (full-length) coding
      gene

<400> SEQUENCE: 52

```
gaggtccagc tcctggagag cggaggagga ttggttcaac ccggaggatc actccgtttg      60
agttgcgcag ccagtggatt cacttttcct agttattcaa tgtcctgggt tcgtcaggcc    120
cccggcaagg gattggagtg ggtcagcggg atatatagcg atggatcaaa tacctattat    180
gctgatagcg tgaaagggcg atttactata tcacgggaca attccaagaa tacattgtac    240
cttcagatga actcccttag gccgaagac actgccgtgt actattgtgc aaagatgctt    300
catcgttttg attattgggg gcaaggaact ctggtgactg tctcaagcgc ctccaccaag    360 ggccctccg tgttccccct ggccccctcc tccaagtcca cctccggcgg caccgccgcc    420
ctgggctgcc tggtgaagga ctacttcccc gagcccgtga ccgtgtcctg aactccggc     480 gccctgacct ccggcgtgca caccttcccc gccgtgctgc agtcctccgg cctgtactcc    540
ctgtcctccg tcgtgaccgt gccctcctcc tccctgggca cccagaccta catctgcaac    600
gtgaaccaca agccctccaa caccaaggtg acaagaagg tggagcccaa gtcctgcgac     660
aagacccaca cctgccctcc ctgccccgcc cccgagctgc tgggcggccc ctccgtgttc    720
ctgttccctc ctaagcccaa ggacaccctg atgatctccc ggaccccga ggtgacttgc     780 gtggtggtgg acgtgtccca cgaggacccc gaggtgaagt tcaactggta cgtggacggc    840
gtggaggtgc acaacgccaa gaccaagccc cgggaggagc agtacaactc cacctaccgg    900
gtggtgtccg tgctgaccgt gctgcaccag gactggctga acggcaagga gtacaagtgc    960
aaggtgtcca acaaggccct gcccgccccc atcgagaaga ccatctccaa ggccaagggc   1020
cagccccggg agccccaggt gtacaccctg ccccctccc gggaggagat gaccaagaac    1080
caggtgtccc tgacctgcct ggtgaagggc ttctaccct ccgacatcgc cgtggagtgg     1140
gagtccaacg gccagcccga gaacaactac aagaccaccc ccccgtgct ggactccgac    1200
```

```
ggctccttct tcctgtactc caagctgacc gtggacaagt cccggtggca gcagggcaac    1260
gtgttctcct gctccgtgat gcacgaggcc ctgcacaacc actacaccca gaagtccctg    1320
tccctgtccc ccggcaag                                                  1338
```

<210> SEQ ID NO 53
<211> LENGTH: 1353
<212> TYPE: DNA
<213> ORGANISM: Artificial Sequence
<220> FEATURE:
<223> OTHER INFORMATION: Synthetic: Heavy chain (full-length) coding
      gene

<400> SEQUENCE: 53

```
gaagttcagc tgttggaatc tggcggcgga ttggttcagc ctggcggatc tctgagactg     60
tcttgtgccg cctctggctt caccttctcc gactacgcta tgtcctgggt ccgacaggct    120
cctggcaaag gattgagtg ggtgtccgga atttcccctg cggctctaa caccctactac    180 gccgattccg tgaagggcag attcaccatc agccgggaca actccaagaa cacccctgtac   240 ctgcagatga actccctgag agccgaggac accgccgtgt actactgtgc caaggatgcc    300
tggatcgcca gactgctgct gttcgattat tggggcaggg gcacactggt caccgtgtcc    360
tctgcttcta ccaagggacc ctctgtgttc cctctggctc cttccagcaa gtctacctct    420
ggtggaaccg ctgctctggg ctgcctggtc aaggattact tcctgagcc tgtgaccgtg    480 tcttggaact ccggtgctct gacatctggc gtgcacacct ttccagctgt gctgcagtcc    540
tctggcctgt actctctgtc ctctgtcgtg accgtgcctt ctagctctct gggcacccag    600
acctacatct gcaacgtgaa ccacaagcct tccaacacca aggtggacaa gaaggtggaa    660
cccaagtcct gcgacaagac ccacacctgt cctccatgtc ctgctccaga actgctcggc    720
ggtccctccg ttttcctgtt tccacctaag cctaaggaca cctgatgat ctctcggacc    780 cctgaagtga cctgcgtggt ggtggatgtg tctcacgagg atcccgaagt gaagttcaat    840
tggtacgtgg acggcgtgga agtgcacaac gccaagacca gcctagaga ggaacagtac    900 aactccacct acagagtggt gtccgtgctg accgtgctgc accaggattg gctgaacggc    960
aaagagtaca agtgcaaggt gtccaacaag gccctgcctg ctcctatcga aaagaccatc   1020
tccaaggcta agggccagcc tcgggaacct caggtgtaca ccctgcctcc atctcgggaa   1080
gagatgacca agaaccaggt gtccctgacc tgcctcgtga agggattcta cccttccgat   1140
atcgccgtgg aatgggagtc caatggccag cctgagaaca actacaagac aacccctcct   1200
gtgctggact ccgacggctc attcttcctg tactccaagc tgacagtgga caagtctcgg   1260
tggcagcagg gcaacgtgtt ctcctgttct gtgatgcacg aggccctgca caaccactac   1320
acccagaagt ccctgtctct gtcccctggc aaa                                1353
```

<210> SEQ ID NO 54
<211> LENGTH: 1338
<212> TYPE: DNA
<213> ORGANISM: Artificial Sequence
<220> FEATURE:
<223> OTHER INFORMATION: Synthetic: Heavy chain (full-length) coding
      gene

<400> SEQUENCE: 54

```
gaggttcagc tccttgaatc aggggggggt cttgtccagc ccggaggttc ccttcgcttg     60
agctgtgcag catcagggtt taccttcagt tcttatggga tgtcttgggt acgtcaggca    120
```

```
cctggcaaag gtctcgaatg ggtcagtggt atatattctg gcggaagcag taagtactac    180
gccgatagcg taaaaggtcg tttcaccatc tctagggaca attccaagaa taccttgtac    240
ttgcagatga acagtctccg agctgaagat acagctgtct actattgtgc taaaaacagg    300
cttcgattcg attattgggg ccagggtact cttgttactg tcagtagtgc ctccaccaag    360 ggccctccg tgttccccct ggccccctcc tccaagtcca cctccggcgg caccgccgcc    420
ctgggctgcc tggtgaagga ctacttcccc gagcccgtga ccgtgtcctg gaactccggc    480
gccctgacct ccggcgtgca caccttcccc gccgtgctgc agtcctccgg cctgtactcc    540
ctgtcctccg tcgtgaccgt gccctcctcc ccctgggca cccagaccta catctgcaac    600
gtgaaccaca agccctccaa caccaaggtg gacaagaagg tggagcccaa gtcctgcgac    660
aagacccaca cctgccctcc ctgccccgcc cccgagctgc tgggcggccc ctccgtgttc    720
ctgttccctc ctaagcccaa ggacaccctg atgatctccc ggaccccga ggtgacttgc    780 gtggtggtgg acgtgtccca cgaggacccc gaggtgaagt tcaactggta cgtggacggc    840
gtggaggtgc acaacgccaa gaccaagccc cgggaggagc agtacaactc cacctaccgg    900
gtggtgtccg tgctgaccgt gctgcaccag gactggctga acggcaagga gtacaagtgc    960
aaggtgtcca acaaggccct gccccgccccc atcgagaaga ccatctccaa ggccaagggc   1020
cagccccggg agcccaggt gtacaccctg cccccctccc gggaggagat gaccaagaac   1080
caggtgtccc tgacctgcct ggtgaagggc ttctaccct ccgacatcgc cgtggagtgg   1140
gagtccaacg ccagcccga gaacaactac aagaccaccc ccccgtgct ggactccgac   1200 ggctccttct cctgtactc caagctgacc gtggacaagt cccggtggca gcagggcaac   1260
gtgttctcct gctccgtgat gcacgaggcc ctgcacaacc actacaccca gaagtccctg   1320
tccctgtccc ccggcaag                                                  1338
```

<210> SEQ ID NO 55
<211> LENGTH: 648
<212> TYPE: DNA
<213> ORGANISM: Artificial Sequence
<220> FEATURE:
<223> OTHER INFORMATION: Synthetic: Light chain (full-length) coding gene

<400> SEQUENCE: 55

```
cagtctgttc tgactcagcc tccttctgct tctggcaccc ctggccagag agtgaccatc     60
tcttgttccg gctcctcctc caacatcggc tctaacgccg tgtcctggta tcagcagttg    120
cctggcacag cccctaagct gctgatctac tacaactctc acagaccctc cggcgtgccc    180
gacagattct ctggctctaa gtctggcacc tccgccagcc tggctatctc tggactgaga    240
tctgaggacg aggccgacta ctactgcggc tcttgggatg cctctctgaa cgcttatgtg    300
ttcggcggag gcaccaagct gacagtgttg ggacaaccta aggccgctcc tagcgtgacc    360
ctgtttcctc catcttctga ggaactgcag gccaacaagg ctaccctcgt gtgcctgatc    420
tctgactttt accctggcgc tgtgaccgtg gcctggaagg ctgatagttc tcctgtgaag    480
gccggcgtgg aaaccaccac accttccaag cagtccaaca caaatacgc cgcctcctcc    540 tacctgtctc tgacccctga acagtggaag tcccaccggt cctactcttg ccaagtgacc    600
catgagggct ccaccgtgga aaagacagtg gcccctgctg agtgctct                648
```

<210> SEQ ID NO 56
<211> LENGTH: 648
<212> TYPE: DNA

<213> ORGANISM: Artificial Sequence
<220> FEATURE:
<223> OTHER INFORMATION: Synthetic: Light chain (full-length) coding
      gene

<400> SEQUENCE: 56

| | | | | | |
|---|---|---|---|---|---|
| cagtctgtgc | ttacccaacc | tcctagtgca | agtggtaccc | tggacaacg | agtaacaatc | 60 |
| agttgcactg | gtagttcaag | taatatagga | tctaacgacg | taagttggta | tcagcaactt | 120 |
| cctggtacag | cacctaagtt | gctcatttac | gcaaactccc | atagacctc | tggcgtccct | 180 |
| gatcgtttca | gcggtagtaa | atccggtaca | tcagcttcct | tggctatatc | tggtctcaga | 240 |
| tccgaggacg | aagctgacta | ttactgtggg | agttgggatg | actctttgtc | cggctacgtt | 300 |
| tttggaggag | gcaccaagtt | gacagtgctg | ggtcagccca | aggccgcccc | ctccgtgacc | 360 |
| ctgttccccc | cctcctccga | ggagctgcag | gccaacaagg | ccaccctggt | gtgcctgatc | 420 |
| tccgacttct | accccggcgc | cgtgaccgtg | gcctggaagg | ccgactcctc | ccccgtgaag | 480 |
| gccggcgtgg | agaccaccac | ccctccaag | cagtccaaca | caagtacgc | cgcctcctcc | 540 |
| tacctgtccc | tgaccccga | gcagtggaag | tcccaccggt | cctactcctg | ccaggtgacc | 600 |
| cacgagggct | ccaccgtgga | gaagaccgtg | gcccccgccg | agtgctcc | | 648 |

<210> SEQ ID NO 57
<211> LENGTH: 648
<212> TYPE: DNA
<213> ORGANISM: Artificial Sequence
<220> FEATURE:
<223> OTHER INFORMATION: Synthetic: Light chain (full-length) coding
      gene

<400> SEQUENCE: 57

| | | | | | |
|---|---|---|---|---|---|
| caatctgtgc | tgacccaacc | acccagtgct | tcaggcacac | ccggacagag | ggtgactata | 60 |
| agttgcagcg | ggtcaagttc | aaatatcgga | agcaattccg | tgacctggta | ccaacagctc | 120 |
| cccggtactg | caccaaagct | ccttatctat | gctgattctc | agcggcctag | tggagtgcct | 180 |
| gatcggttca | gcggttcaaa | gtccggtacc | tccgcttctt | tggcaataag | tggattgcgc | 240 |
| tccgaggatg | aggcagatta | ttattgcggg | acatgggata | gcagtcttaa | tgcctacgta | 300 |
| ttcggcggtg | gtaccaaact | tacagttctc | ggccagccca | aggccgcccc | ctccgtgacc | 360 |
| ctgttccccc | cctcctccga | ggagctgcag | gccaacaagg | ccaccctggt | gtgcctgatc | 420 |
| tccgacttct | accccggcgc | cgtgaccgtg | gcctggaagg | ccgactcctc | ccccgtgaag | 480 |
| gccggcgtgg | agaccaccac | ccctccaag | cagtccaaca | caagtacgc | cgcctcctcc | 540 |
| tacctgtccc | tgaccccga | gcagtggaag | tcccaccggt | cctactcctg | ccaggtgacc | 600 |
| cacgagggct | ccaccgtgga | gaagaccgtg | gcccccgccg | agtgctcc | | 648 |

<210> SEQ ID NO 58
<211> LENGTH: 648
<212> TYPE: DNA
<213> ORGANISM: Artificial Sequence
<220> FEATURE:
<223> OTHER INFORMATION: Synthetic: Light chain (full-length) coding
      gene

<400> SEQUENCE: 58

| | | | | | |
|---|---|---|---|---|---|
| cagtctgttc | tgactcagcc | tccttctgct | tctggcaccc | ctggccagag | agtgaccatc | 60 |
| tcttgttccg | gctcctcctc | caacatcggc | tctaacgctg | tgacctggta | tcagcagctg | 120 |
| cctggcacag | cccctaaact | gctgatctac | tacaacaaca | agcggccctc | tggcgtgccc | 180 |

```
gacagattct ctggatctaa gtccggcacc tctgccagcc tggctatctc tggactgaga    240
tctgaggacg aggccgacta ctactgcggc acctgggatg attctctgtc cggctatgtg    300
ttcggcggag cacaaaact gacagtgctg ggacagccta aggccgctcc ttctgtgacc     360
ctgtttcctc catcctctga ggaactgcag gccaacaagg ctaccctcgt gtgcctgatc    420
tctgactttt atcctggcgc cgtgaccgtg gcctggaagg ctgatagttc tcctgtgaag    480
gccggcgtgg aaaccaccac accttccaag cagtccaaca caaatacgc cgcctcctcc    540 tacctgtctc tgaccctga acagtggaag tcccaccggt cctactcttg ccaagtgacc    600
catgagggct ccaccgtgga aagacagtg gcccctgctg agtgctct                  648
```

<210> SEQ ID NO 59
<211> LENGTH: 648
<212> TYPE: DNA
<213> ORGANISM: Artificial Sequence
<220> FEATURE:
<223> OTHER INFORMATION: Synthetic: Light chain (full-length) coding gene

<400> SEQUENCE: 59

```
caaagcgttt tgactcagcc tccttcagct tctggaactc caggacaacg tgtcaccatc     60
agttgcaccg gctcttcctc caacatcgga agtaacagcg ttacctggta tcagcagctc    120
ccaggcactg ccccaaagct cttgatatac tcagactccc atcgaccatc cggagttcct    180
gacagattca gcggttcaaa atctggtact tctgcatcac ttgccatttc cggtctccga    240
tcagaagacg aagctgacta ttattgtgga acctgggatg cctcccttaa cgcttacgtt    300
ttcggaggtg caccaagct cacagttctc ggacagccca aggccgcccc ctccgtgacc     360 ctgttcccc cctcctccga ggagctgcag gccaacaagg ccaccctggt gtgcctgatc     420
tccgacttct accccggcgc cgtgaccgtg gcctggaagg ccgactcctc ccccgtgaag    480
gccggcgtgg agaccaccac ccctccaag cagtccaaca caagtacgc cgcctcctcc     540 tacctgtccc tgacccccga gcagtggaag tcccaccggt cctactcctg ccaggtgacc    600
cacgagggct ccaccgtgga gaagaccgtg gccccgccg agtgctcc                   648
```

<210> SEQ ID NO 60
<211> LENGTH: 330
<212> TYPE: PRT
<213> ORGANISM: Artificial Sequence
<220> FEATURE:
<223> OTHER INFORMATION: Synthetic: Heavy chain constant region

<400> SEQUENCE: 60

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110
```

Pro Ala Pro Glu Leu Leu Gly Gly Pro Ser Val Phe Leu Phe Pro Pro
            115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
            195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
        290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 61
<211> LENGTH: 1001
<212> TYPE: DNA
<213> ORGANISM: Artificial Sequence
<220> FEATURE:
<223> OTHER INFORMATION: Synthetic: Heavy chain constant region coding
      gene

<400> SEQUENCE: 61
gcctccacca agggcccctc cgtgttcccc ctggccccct cctccaagtc cacctccggc      60
ggcaccgccg ccctgggctg cctggtgaag gactacttcc ccgagcccgt gaccgtgtcc     120
tggaactccg gcgccctgac ctccggcgtg cacaccttcc ccgccgtgct gcagtcctcc     180
ggcctgtact ccctgtcctc cgtcgtgacc gtgccctcct cctccctggg cacccagacc     240
tacatctgca acgtgaacca caagccctcc aacaccaagg tggacaagaa ggtggagccc     300
aagtcctgcg acaagaccca cacctgcccc cctgccccg ccccgagct gctgggcggc      360 ccctccgtgt tcctgttccc tcctaagccc aaggacaccc tgatgatctc ccggaccccc     420
gaggtgactt gcgtggtggt ggacgtgtcc cacgaggacc ccgaggtgaa gttcaactgg     480
tacgtggacg gcgtggaggt gcacaacgcc aagaccaagc ccgggagga gcagtacaac     540 tccacctacc gggtggtgtc cgtgctgacc gtgctgcacc aggactggct gaacggcaag     600
gagtacaagt gcaaggtgtc caacaaggcc ctgcccgccc ccatcgagaa gaccatctcc     660
aaggccaagg gccagccccg ggagccccag gtgtacaccc tgccccctc ccggggagga     720 atgaccaaga accaggtgtc cctgacctgc ctggtgaagg gcttctaccc ctccgacatc     780

```
gccgtggagt gggagtccaa cggccagccc gagaacaact acaagaccac ccccccgtg    840 ctggactccg acggctcctt cttcctgtac tccaagctga ccgtggacaa gtcccggtgg    900
cagcagggca acgtgttctc ctgctccgtg atgcacgagg ccctgcacaa ccactacacc    960
cagaagtccc tgtccctgtc ccccggcaag tgagcggccg c                        1001
```

<210> SEQ ID NO 62
<211> LENGTH: 990
<212> TYPE: DNA
<213> ORGANISM: Artificial Sequence
<220> FEATURE:
<223> OTHER INFORMATION: Synthetic: Heavy chain constant region coding gene

<400> SEQUENCE: 62

```
gcttctacca agggaccctc tgtgttccct ctggctcctt ccagcaagtc tacctctggt     60
ggaaccgctg ctctgggctg cctggtcaag gattactttc ctgagcctgt gaccgtgtct    120
tggaactccg gtgctctgac atctggcgtg cacacctttc agctgtgct gcagtcctct    180 ggcctgtact ctctgtcctc tgtcgtgacc gtgccttcta gctctctggg cacccagacc    240
tacatctgca acgtgaacca caagccttcc aacaccaagg tggacaagaa ggtggaaccc    300
aagtcctgcg acaagaccca cacctgtcca ccatgtcctg ctccagaact gctcggcgt     360 ccctccgttt tcctgtttcc acctaagcct aaggacaccc tgatgatctc tcggacccct    420
gaagtgacct gcgtggtggt ggatgtgtct cacgaggatc cgaagtgaa gttcaattgg    480 tacgtggacg gcgtggaagt gcacaacgcc aagaccaagc ctagagagga acagtacaac    540
tccacctaca gagtggtgtc cgtgctgacc gtgctgcacc aggattggct gaacggcaaa    600
gagtacaagt gcaaggtgtc caacaaggcc ctgcctgctc ctatcgaaaa gaccatctcc    660
aaggctaagg gccagcctcg ggaacctcaa gtgtacacct gccacccttc cagagaagag    720
atgaccaaga accaggtgtc cctgacctgc ctcgtgaagg gcttctaccc ttccgatatc    780
gccgtggaat gggagtctaa cggccagcca gagaacaact acaagacaac ccctcctgtg    840
ctggactccg acggctcatt cttcctgtac tccaagctga cagtggacaa gtctcggtgg    900
cagcagggca acgtgttctc ctgttctgtg atgcacgagg ccctgcacaa ccactacacc    960
cagaagtccc tgtctctgtc ccctggcaaa                                    990
```

<210> SEQ ID NO 63
<211> LENGTH: 990
<212> TYPE: DNA
<213> ORGANISM: Artificial Sequence
<220> FEATURE:
<223> OTHER INFORMATION: Synthetic: Heavy chain constant region coding gene

<400> SEQUENCE: 63

```
gcttctacca agggaccctc tgtgttccct ctggctcctt ccagcaagtc tacctctggt     60
ggaaccgctg ctctgggctg cctggtcaag gattactttc ctgagcctgt gaccgtgtct    120
tggaactccg gtgctctgac atctggcgtg cacacctttc agctgtgct gcagtcctct    180 ggcctgtact ctctgtcctc tgtcgtgacc gtgccttcta gctctctggg cacccagacc    240
tacatctgca acgtgaacca caagccttcc aacaccaagg tggacaagaa ggtggaaccc    300
aagtcctgcg acaagaccca cacctgtcct ccatgtcctg ctccagaact gctcggcggt    360
ccctccgttt tcctgtttcc acctaagcct aaggacaccc tgatgatctc tcggacccct    420
```

```
gaagtgacct gcgtggtggt ggatgtgtct cacgaggatc cgaagtgaa gttcaattgg    480 tacgtggacg gcgtggaagt gcacaacgcc aagaccaagc ctagagagga acagtacaac    540
tccacctaca gagtggtgtc cgtgctgacc gtgctgcacc aggattggct gaacggcaaa    600
gagtacaagt gcaaggtgtc caacaaggcc ctgcctgctc ctatcgaaaa gaccatctcc    660
aaggctaagg gccagcctcg ggaacctcag gtgtacaccc tgcctccatc tcgggaagag    720
atgaccaaga accaggtgtc cctgacctgc ctcgtgaagg gattctaccc ttccgatatc    780
gccgtggaat gggagtccaa tggccagcct gagaacaact acaagacaac ccctcctgtg    840
ctggactccg acggctcatt cttcctgtac tccaagctga cagtggacaa gtctcggtgg    900
cagcagggca acgtgttctc ctgttctgtg atgcacgagg ccctgcacaa ccactacacc    960
cagaagtccc tgtctctgtc ccctggcaaa                                    990
```

<210> SEQ ID NO 64
<211> LENGTH: 105
<212> TYPE: PRT
<213> ORGANISM: Artificial Sequence
<220> FEATURE:
<223> OTHER INFORMATION: Synthetic: Light chain constant region

<400> SEQUENCE: 64

```
Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Ala Glu Cys Ser
            100                 105
```

<210> SEQ ID NO 65
<211> LENGTH: 315
<212> TYPE: DNA
<213> ORGANISM: Artificial Sequence
<220> FEATURE:
<223> OTHER INFORMATION: Synthetic: Light chain constant region coding
      gene

<400> SEQUENCE: 65

```
cagcccaagg ccgcccctc cgtgaccctg ttccccccct cctccgagga gctgcaggcc    60
aacaaggcca ccctggtgtg cctgatctcc gacttctacc ccggcgccgt gaccgtggcc   120
tggaaggccg actcctcccc cgtgaaggcc ggcgtggaga ccaccacccc ctccaagcag   180
tccaacaaca agtacgccgc ctcctcctac ctgtccctga ccccgagca gtggaagtcc    240 caccggtcct actcctgcca ggtgacccac gagggctcca ccgtggagaa gaccgtggcc   300
cccgccgagt gctcc                                                   315
```

<210> SEQ ID NO 66
<211> LENGTH: 315
<212> TYPE: DNA
<213> ORGANISM: Artificial Sequence
<220> FEATURE:
<223> OTHER INFORMATION: Synthetic: Light chain constant region coding
      gene

<400> SEQUENCE: 66
caacctaagg ccgctcctag cgtgaccctg tttcctccat cttctgagga actgcaggcc      60
aacaaggcta ccctcgtgtg cctgatctct gacttttacc ctggcgctgt gaccgtggcc     120
tggaaggctg atagttctcc tgtgaaggcc ggcgtggaaa ccaccacacc ttccaagcag     180
tccaacaaca aatacgccgc ctcctcctac ctgtctctga cccctgaaca gtggaagtcc     240
caccggtcct actcttgcca agtgacccat gagggctcca ccgtggaaaa gacagtggcc     300
cctgctgagt gctct                                                      315

<210> SEQ ID NO 67
<211> LENGTH: 315
<212> TYPE: DNA
<213> ORGANISM: Artificial Sequence
<220> FEATURE:
<223> OTHER INFORMATION: Synthetic: Light chain constant region coding
      gene

<400> SEQUENCE: 67
cagcctaagg ccgctccttc tgtgaccctg tttcctccat cctctgagga actgcaggcc      60
aacaaggcta ccctcgtgtg cctgatctct gactttatc ctggcgccgt gaccgtggcc     120
tggaaggctg atagttctcc tgtgaaggcc ggcgtggaaa ccaccacacc ttccaagcag     180
tccaacaaca aatacgccgc ctcctcctac ctgtctctga cccctgaaca gtggaagtcc     240
caccggtcct actcttgcca agtgacccat gagggctcca ccgtggaaaa gacagtggcc     300
cctgctgagt gctct                                                      315

<210> SEQ ID NO 68
<211> LENGTH: 17
<212> TYPE: PRT
<213> ORGANISM: Artificial Sequence
<220> FEATURE:
<223> OTHER INFORMATION: Synthetic: Heavy chain CDR2

<400> SEQUENCE: 68

Gly Ile Tyr Ser Asp Ala Ser Asn Thr Tyr Tyr Ala Asp Ser Val Lys
1               5                   10                  15
Gly

<210> SEQ ID NO 69
<211> LENGTH: 7
<212> TYPE: PRT
<213> ORGANISM: Artificial Sequence
<220> FEATURE:
<223> OTHER INFORMATION: Synthetic: Light chain CDR2

<400> SEQUENCE: 69

Ala Asp Val Gln Arg Pro Ser
1               5

<210> SEQ ID NO 70
<211> LENGTH: 116
<212> TYPE: PRT
<213> ORGANISM: Artificial Sequence
<220> FEATURE:
<223> OTHER INFORMATION: Synthetic: Heavy chain variable region

<400> SEQUENCE: 70

-continued

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45

Ser Gly Ile Tyr Ser Asp Ala Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Met Leu His Arg Phe Asp Tyr Trp Gly Gln Gly Thr Leu Val
            100                 105                 110

Thr Val Ser Ser
            115
```

<210> SEQ ID NO 71
<211> LENGTH: 111
<212> TYPE: PRT
<213> ORGANISM: Artificial Sequence
<220> FEATURE:
<223> OTHER INFORMATION: Synthetic: Light chain variable region

<400> SEQUENCE: 71

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Ser Val Thr Trp Tyr Gln Gln Leu Pro Gly Thr Ala Pro Lys Leu Leu
        35                  40                  45

Ile Tyr Ala Asp Val Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Ser Ser Leu
                85                  90                  95

Asn Ala Tyr Val Phe Gly Gly Gly Thr Lys Leu Thr Val Leu Gly
            100                 105                 110
```

<210> SEQ ID NO 72
<211> LENGTH: 446
<212> TYPE: PRT
<213> ORGANISM: Artificial Sequence
<220> FEATURE:
<223> OTHER INFORMATION: Synthetic: Heavy chain

<400> SEQUENCE: 72

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45

Ser Gly Ile Tyr Ser Asp Ala Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
                85                  90                  95

Ala Lys Met Leu His Arg Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 73
<211> LENGTH: 216
<212> TYPE: PRT
<213> ORGANISM: Artificial Sequence
<220> FEATURE:
<223> OTHER INFORMATION: Synthetic: Light chain

<400> SEQUENCE: 73

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Ser Val Thr Trp Tyr Gln Gln Leu Pro Gly Thr Ala Pro Lys Leu Leu
        35                  40                  45

Ile Tyr Ala Asp Val Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Ser Ser Leu
                85                  90                  95

Asn Ala Tyr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Ala Glu Cys Ser
    210                 215

<210> SEQ ID NO 74
<211> LENGTH: 1338
<212> TYPE: DNA
<213> ORGANISM: Artificial Sequence
<220> FEATURE:
<223> OTHER INFORMATION: Synthetic: Heavy chain coding gene

<400> SEQUENCE: 74
gaggtccagc tcctggagag cggaggagga ttggttcaac ccggaggatc actccgtttg      60
agttgcgcag ccagtggatt cacttttttct agttattcaa tgtcctgggt tcgtcaggcc    120
cccggcaagg gattggagtg ggtcagcggg atatatagcg atgcttcaaa tacctattat    180
gctgatagcg tgaaagggcg atttactata tcacgggaca attccaagaa tacattgtac    240
cttcagatga actcccttag gccgaagac actgccgtgt actattgtgc aaagatgctt    300
catcgttttg attattgggg gcaaggaact ctggtgactg tctcaagcgc ctccaccaag    360
ggcccctccg tgttcccccct ggccccctcc tccaagtcca cctccggcgg caccgccgcc    420
ctgggctgcc tggtgaagga ctacttcccc gagcccgtga ccgtgtcctg aactccggc     480 gccctgacct ccggcgtgca caccttcccc gccgtgctgc agtcctccgg cctgtactcc    540
ctgtcctccg tcgtgaccgt gccctcctcc tccctgggca cccagaccta catctgcaac    600
gtgaaccaca agccctccaa caccaaggtg gacaagaagg tggagcccaa gtcctgcgac    660
aagacccaca cctgccctcc ctgccccgcc ccgagctgc tgggcggccc ctccgtgttc     720
ctgttccctc ctaagcccaa ggacaccctg atgatctccc ggaccccga ggtgacttgc     780

```
gtggtggtgg acgtgtccca cgaggacccc gaggtgaagt tcaactggta cgtggacggc    840
gtggaggtgc acaacgccaa gaccaagccc cggaggagc  agtacaactc cacctaccgg    900
gtggtgtccg tgctgaccgt gctgcaccag gactggctga acggcaagga gtacaagtgc    960
aaggtgtcca acaaggccct gcccgccccc atcgagaaga ccatctccaa ggccaagggc   1020
cagccccggg agcccaggt  gtacaccctg ccccctccc  gggaggagat gaccaagaac   1080
caggtgtccc tgacctgcct ggtgaagggc ttctacccct ccgacatcgc cgtggagtgg   1140
gagtccaacg gccagcccga gaacaactac aagaccaccc ccccgtgct  ggactccgac   1200 ggctccttct tcctgtactc caagctgacc gtggacaagt cccggtggca gcagggcaac   1260
gtgttctcct gctccgtgat gcacgaggcc ctgcacaacc actacaccca gaagtccctg   1320
tccctgtccc ccggcaag                                                 1338

<210> SEQ ID NO 75
<211> LENGTH: 648
<212> TYPE: DNA
<213> ORGANISM: Artificial Sequence
<220> FEATURE:
<223> OTHER INFORMATION: Synthetic: Light chain coding gene

<400> SEQUENCE: 75
caatctgtgc tgacccaacc acccagtgct tcaggcacac ccggacagag ggtgactata     60
agttgcagcg ggtcaagttc aaatatcgga agcaattccg tgacctggta ccaacagctc    120
cccggtactg caccaaagct ccttatctat gctgatgtgc agcggcctag tggagtgcct    180
gatcggttca gcggttcaaa gtccggtacc tccgcttctt tggcaataag tggattgcgc    240
tccgaggatg aggcagatta ttattgcggg acatgggata gcagtcttaa tgcctacgta    300
ttcggcggtg gtaccaaact tacagttctc ggccagccca aggccgcccc ctccgtgacc    360
ctgttccccc cctcctccga ggagctgcag gccaacaagg ccaccctggt gtgcctgatc    420
tccgacttct accccggcgc cgtgaccgtg gcctggaagg ccgactcctc ccccgtgaag    480
gccggcgtgg agaccaccac ccctccaag  cagtccaaca caagtacgc  cgcctcctcc    540 tacctgtccc tgacccccga gcagtggaag tccaccggt  cctactcctg ccaggtgacc    600
cacgagggct ccaccgtgga gaagaccgtg gcccccgccg agtgctcc               648
```

ANTI-B7-H3 ANTIBODY AND USE THEREOF

BACKGROUND OF THE INVENTION

1. Field

Provided is an anti-B7-H3 antibody or an antigen-binding fragment thereof, and its use.

2. Description of the Related Art

B7-H3 (CD276) is a member of the B7 family, and is a transmembrane protein containing an extracellular domain, transmembrane domain and intracellular domain. The two extracellular domains of B7-H3 consist of a single pair (2Ig B7-H3) or two identical pairs (4Ig B7-H3) of immunoglobulin variable domain and immunoglobulin constant domain due to exon duplication. The functional difference between these two forms was not confirmed. The intracellular domain of B7-H3 is short and there is no known motif (Chapoval A I, Ni J, Lau J S, Wilcox R A, Flies D B, Liu D, et al. NatImmunol 2001; 2:269-74.).

The B7-H3 has 20-27% amino acid identity with other members of B7 family. A human B7-H3 has 88% amino acid identity with a mouse B7-H3. While the mouse B7-H3 has one subtype (2IgB7-H3), the human B7-H3 has two subtypes (2Ig B7-H3, 4Ig B7-H3). 4Ig B7-H3 is confirmed in a human tissue superiorly.

It was found that the mouse B7-H3 bound to TLT1 of a CD8+ T cell, thereby enhancing proliferation of T cell, cytokine production and cytotoxicity, and therefore it was suggested that TLT2 could act as a B7-H3 receptor. However, afterwards, the evidence for this interaction has not been found in both mouse and human (M. Loos, D. M. Hedderich, and D. M. Hedderich, et al. *BMC Cancer*, vol. 9, article 463, 2009).

The B7-H3 protein is not always expressed in a natural killer cell (NK cell) and an antigen presenting cell (APC) in a normal tissue, but its expression may be induced. Although the expression of B7-1 and B7-2 is mostly limited to an immunocyte such as the antigen presenting cell, the B7-H3 protein is present in not only osteoblast, fibroblast, fibroblast-like synovial cell and epithelial cell but also liver, lung, bladder, testis, prostate, breast, placenta and lymphatic vessel organs of human. This wide expression pattern suggests more various immunological and non-immunologic function in B7-H3, particularly in a peripheral tissue.

In recent years, the B7-H3 expression has been confirmed in various solid cancer such as non-small cell lung cancer, renal cell carcinoma, neuroblastoma, colorectal cancer, pancreatic cancer, gastric cancer, lung cancer, prostate cancer, endometrial cancer, hepatocellular carcinoma, breast cancer, cervical cancer, osteosarcoma, oral cancer, bladder cancer, glioma, melanoma, etc., and it has been reported that it is expressed in hematologic malignancy such as acute leukemia, multiple myeloma, various kinds of lymphomas (Zhimeng Yea, Zhuojun Zhengb et al, Cell Physiol Biochem (2016), Elodie Picarda, Kim C. Ohaegbulam and Xingxing Zang, clinical cancer research (2016), Wei Zhang, Yanfang Wang, Jing Wang et al, international journal of oncology (2015)).

B7-H3 is overexpressed in various cancer kinds, but the expression in a normal tissue is very low. In many researches, in a majority of cancer types, abnormal expression of B7-H3 is shown, and it was shown that it was found in a tumor-related vascular system as well as in cytoplasm or a nucleus of cancer cell. When estimating various clinicopathologic indexes such as size of tumor, metastasis, cancer stage, survival rate and relapse rate, etc., the overexpression of B7-H3 is correlated with bad prognosis and bad clinical results. According to one research of prostate cancer patients, the oncocytic patients in which the B7-H3 expression is strong have significantly high disease transmission risk at the time of surgery, clinical cancer relapse and cancer-related death risk. The expression of B7-H3 to lung cancer is related to reduction of tumor-infiltrating lymphocytes (TILs) and lymphatic gland metastasis, and suggest a role of B7-H3 on immune evasion and tumor formation (Elodie Picarda, Kim C. Ohaegbulam and Xingxing Zang, Clin Cancer Res, 2017 Jul. 12; 22).

B7-H3 has a non-immunologic function controlling tumor aggression in addition to a role of controlling tumor immune. It was shown that that controlled migration to fibronectin, invasion and request of various cancer cells through Jak2/Stat3/MMP-9 signaling pathway (Elodie Picarda, Kim C. Ohaegbulam and Xingxing Zang, Clin Cancer Res, 2017 Jul. 12; 22). A tumor-related antigen, B7-H3 reduced cell adhesion to fibronectin and reduced migration and infiltration in melanoma and breast cancer cells by 70% or more, through down-regulation by siRNA (Chen Y W, Tekle C, Fodstad O, Curr Cancer Drug Targets 2008; 8). These results suggest that B7-H3 can be a useful target for cancer treatment.

B7-H3 is a protein which belongs to an immune checkpoint ligand. The immune checkpoint protein acts to control immunocytes in a human body to prevent them from making false abnormal behavior. When the immune checkpoint protein is overexpressed in a cancer cell, immunocytes receive an abnormal signal which the cancer cell sends as a normal signal, and recognize the cancer cell as a healthy cell. An immune checkpoint inhibitor is an anti-cancer immune-therapeutic agent which blocks such an abnormal signal of the cancer cell, thereby treating cancer by immunologic function of a patient himself. B7-H3 which is one of the immune checkpoint ligands binds to a B7-H3 receptor on a T cell surface and induces inhibition of immunoreaction of the T cell, but it is still not revealed what receptor B7-H3 binds.

An antibody which can block such an immune checkpoint ligand shows anti-cancer immune-therapeutic effect by partially or completely neutralizing interaction of immune checkpoint ligands and immune checkpoint receptors and inhibiting immune checkpoint, thereby reactivating the degraded activity of immunocytes. A receptor binding to B7-H3 is not been found yet, but an anti-B7-H3 antibody binding to B7-H3 can show an anti-cancer immune-therapeutic effect by blocking binding between the immune checkpoint receptor and B7-H3 and inhibiting such an immune checkpoint, thereby reactivating the degraded activity of immunocytes. In other words, the anti-B7-H3 monoclonal antibody blocking the binding to the B7-H3 receptor may be expected to have an anti-cancer therapeutic effect (Elodie Picarda, Kim C. Ohaegbulam and Xingxing Zang, Clin Cancer Res, 2017 Jul. 12; 22). U.S. Pat. Nos. 8,802,091 and 9,371,395 disclose antibodies to B7-H3.

Since antibodies against the same B7-H3 antigen can be developed to various anti-cancer antibodies depending on properties or uses of each antibody, considering cancer-specific expression of B7-H3, its expression in various cancers, and its function as an immune checkpoint ligand, it is necessary to develop various antibodies that can replace or complement existing antibodies.

SUMMARY OF THE INVENTION

The present invention provides a protein, for example an antibody or its antigen-binding fragment, which is capable of specifically recognizing B7-H3.

One embodiment provides an isolated antibody specifically binding to an extracellular domain of B7-H3 or its antigen-binding fragment and use thereof. In particular, the antibody may specifically recognize a human B7-H3, and shows cross-reactivity to a monkey and mouse B7-H3.

In one embodiment, the antibody or antigen-binding fragment may be a polypeptide comprising (i) heavy chain complementary determining regions of CDRH1, CDRH2 and CDRH3, and (ii) light chain complementarity determining regions of CDRL1, CDRL2 and CDRL3, wherein the CDRH1 may comprise or consist essentially of any one selected from SEQ ID NOs: 1 to 4; the CDRH2 may comprise or consist essentially of any one selected from SEQ ID NOs: 5 to 9, and 68; the CDRH3 may comprise or consist essentially of any one selected from SEQ ID NOs: 10 to 14; the CDRL1 may comprise or consist essentially of any one selected from SEQ ID NOs: 15 to 19; the CDRL2 may comprise or consist essentially of any one selected from SEQ ID NOs: 20 to 24, and 69; and the CDRL3 may comprise or consist essentially of any one selected from SEQ ID NOs: 25 to 29. The term "CDRH" represents a CDR comprised in a heavy chain variable region, and the term "CDRL" represents a CDR comprised in a light chain variable region.

In another embodiment, the antibody or antigen-binding fragment may comprise (i) a heavy chain variable region comprising complementary determining regions of CDRH1, CDRH2 and CDRH3 and/or (ii) a light chain variable region comprising complementary determining regions of CDRL1, CDRL2 and CDRL3, wherein the CDRH1 may comprise or consist essentially of any one selected from SEQ ID NOs: 1 to 4; the CDRH2 may comprise or consist essentially of any one selected from SEQ ID NOs: 5 to 9, and 68; the CDRH3 may comprise or consist essentially of any one selected from SEQ ID NOs: 10 to 14; the CDRL1 may comprise or consist essentially of any one selected from SEQ ID NOs: 15 to 19; the CDRL2 may comprise or consist essentially of any one selected from SEQ ID NOs: 20 to 24, and 69; and the CDRL3 may comprise or consist essentially of any one selected from SEQ ID NOs: 25 to 29.

In other embodiment, the CDRH1, CDRH2 and CDRH3 may be a combination selected from the followings: SEQ ID NOs: 1, 5, and 10; SEQ ID NOs: 2, 6, and 11; SEQ ID NOs: 3, 7, and 12; SEQ ID NOs: 1, 8, and 13; or SEQ ID NOs: 4, 9, and 14, or SEQ ID NOs: 3, 68, and 12, respectively.

In other embodiment, the CDRL1, CDRL2 and CDRL3 may be a combination selected from the followings: SEQ ID NOs: 15, 20 and 25; SEQ ID NOs: 16, 21 and 26; SEQ ID NOs: 17, 22 and 27; SEQ ID NOs: 18, 23 and 28; SEQ ID NOs: 19, 24 and 29, or SEQ ID NOs: 17, 69, and 27, respectively.

In other embodiment, the antibody or antigen-binding fragment may be a polypeptide comprising (i) heavy chain complementary determining regions of CDRH1, CDRH2 and CDRH3, and/or (ii) light chain complementarity determining regions of CDRL1, CDRL2 and CDRL3, and the CDRH1, CDRH2 and CDRH3 are one of the following combinations: SEQ ID NOs: 1, 5, and 10, respectively; SEQ ID NOs: 2, 6, and 11, respectively; SEQ ID NOs: 3, 7, and 12, respectively; SEQ ID NOs: 1, 8, and 13, respectively; SEQ ID NOs: 4, 9, and 14, respectively; or SEQ ID NO: 3, 68, and 12, respectively; and the CDRL1, CDRL2, and CDRL3 are one of the following combinations: SEQ ID NOs: 15, 20 and 25, respectively; SEQ ID NOs: 16, 21 and 26, respectively; SEQ ID NOs: 17, 22 and 27, respectively; SEQ ID NOs: 18, 23 and 28, respectively; SEQ ID NOs: 19, 24 and 29, respectively; SEQ ID NOs: 17, 69, and 27, respectively.

One of the combinations of CDRs derived from the heavy chain variable regions and one of the combinations of CDRs derived from the light chain variable regions may be freely combined.

In other embodiment, the sequence of CDRH1, CDRH2 and CDRH3; and the CDRL1, CDRL2 and CDRL3 may be a combination of any one of the followings:

(a) CDRH1, CDRH2 and CDRH3 are SEQ ID NOs: 1, 5, and 10, respectively, and the CDRL1, CDRL2, and CDRL3 are SEQ ID NOs: 15, 20, and 25, respectively;

(b) CDRH1, CDRH2 and CDRH3 are SEQ ID NOs: 2, 6, and 11, respectively, and the CDRL1, CDRL2, and CDRL3 are SEQ ID NOs: 16, 21, and 26, respectively;

(c) CDRH1, CDRH2 and CDRH3 are SEQ ID NOs: 3, 7, and 12, respectively, and the CDRL1, CDRL2, and CDRL3 are SEQ ID NOs: 17, 22, and 27, respectively;

(d) CDRH1, CDRH2 and CDRH3 are SEQ ID NOs: 1, 8, and 13, respectively, and the CDRL1, CDRL2, and CDRL3 are SEQ ID NOs: 18, 23, and 28, respectively;

(e) CDRH1, CDRH2 and CDRH3 are SEQ ID NOs: 4, 9, and 14, respectively, and the CDRL1, CDRL2, and CDRL3 are SEQ ID NOs: 19, 24, and 29, respectively;

(f) CDRH1, CDRH2 and CDRH3 are SEQ ID NOs: 3, 68, and 12, respectively, and the CDRL1, CDRL2, and CDRL3 are SEQ ID NOs: 17, 22, and 27, respectively; or (g) CDRH1, CDRH2 and CDRH3 are SEQ ID NOs: 3, 68, and 12, respectively, and the CDRL1, CDRL2, and CDRL3 are SEQ ID NOs: 17, 69, and 27, respectively.

In other embodiment, the antibody or antigen-binding fragment may comprise a heavy chain variable region represented by any one selected from the group consisting of amino acid sequences of SEQ ID NOs: 30 to 34, and 70.

In other embodiment, the antibody or antigen-binding fragment may comprise a light chain variable region represented by any one selected from the group consisting of amino acid sequences of SEQ ID NOs: 35 to 39, and 71.

Each of the heavy chain variable regions and the light chain variable regions may be combined each other.

In one embodiment, the antibody or antigen-binding fragment may comprise a heavy chain variable region and a light chain variable region, wherein the heavy chain and light chain variable regions may be a combination of the following sequences: SEQ ID NOs: 30 and 35; SEQ ID NOs: 31 and 36; SEQ ID NOs: 32 and 37; SEQ ID NOs: 33 and 38; SEQ ID NOs: 34 and 39; SEQ ID NOs: 70 and 37; or SEQ ID NOs: 70 and 71.

In other embodiment, the antibody may be an IgG type, for example, human, monkey, or mouse IgG1, IgG2, IgG3 or IgG4 type.

In other embodiment, the antibody or antigen-binding fragment provides a heavy chain constant region represented by SEQ ID NO: 60 and/or a light chain constant region represented by SEQ ID NO: 64. For example, heavy chains comprising the heavy chain constant region of SEQ ID NO: 60 may be represented by any one of SEQ ID NOs: 40 to 44, and 72. For example, light chains comprising the light chain constant region of SEQ ID NO: 64 may be represented by any one of SEQ ID NOs: 45 to 49, or 73.

In other embodiment, the antibody may comprise or consist essentially of a combination of a heavy chain and a light chain, which are represented by the following sequence: SEQ ID NOs: 40 and 45; SEQ ID NOs: 41 and 46; SEQ ID NOs: 42 and 47; SEQ ID NOs: 43 and 48; SEQ ID NOs: 44 and 49; SEQ ID NOs: 72 and 47, or SEQ ID NOs: 72 and 73.

In other embodiment, the antibody or antigen-binding fragment may be a humanized antibody, a human antibody (e.g., complete human antibody), or antigen-binding fragment and may have cross-reactivity to B7-H3 of monkey and mouse. The antibody or antigen-binding fragment may be of non-naturally occurring; for example, it may be synthetic or recombinant, but not be limited thereto.

In other embodiment, the antibody may be a monoclonal antibody, in particular, a human monoclonal antibody. In an embodiment, the antibody may have cross-reactivity to monkey B7-H3 and mouse B7-H3.

In other embodiment, the antibody or antigen-binding fragment specifically recognizes human B7-H3, monkey B7-H3, and/or mouse B7-H3.

In other embodiment, the antibody or antigen-binding fragment includes Fab, Fab', F(ab')$_2$, scFab, Fv, dsFv, scFV, scFV-Fc, minibody, diabody, scAb, dAb, bivalent antibody or multivalent antibody, but not limited thereto.

In other embodiment, the antibody or antigen-binding fragment can inhibit or block a B7-H3 immune checkpoint, thereby reactivating a T cell in which the activity is degraded or inhibited by the B7-H3 immune checkpoint. Thus, the antibody or antigen-binding fragment may be usefully used for reactivation of a T cell inhibited by the B7-H3 immune checkpoint and treatment of various diseases requiring the reactivation, through such B7-H3 immune checkpoint inhibition.

In other aspect, the present invention also provides an isolated polynucleotide encoding the antibody or antigen-binding fragment.

In one embodiment, the polynucleotide may be a polynucleotide encoding at least one selected from the group consisting of heavy chain CDRs and light chain CDRs, for example, heavy chain CDRs comprising CDRH1, CDRH2, and CDRH3, and/or light chain CDRs comprising CDRL1, CDRL2, and CDRL3, as disclosed herein.

In other embodiment, the polynucleotide may be a polynucleotide encoding a heavy chain and/or light chain variable region disclosed herein.

In other embodiment, the polynucleotide may be a polynucleotide encoding a heavy chain and/or light chain disclosed herein.

In other aspect, a vector comprising the polynucleotide is provided. In one embodiment, the vector may comprise an expression vector for antibody production or a vector for CAR-T cell (Chimeric Antigen receptor redirected T cells) or CAR-NK (Natural Killer) cell.

In other aspect, provided is a cell line transformed by the vector.

Another embodiment provides a method of preparation of an isolated antibody specifically binding to B7-H3 or its antigen-binding fragment, comprising a step of isolating an antibody or its antigen-binding fragment from the cell line.

Another embodiment provides a composition or pharmaceutical composition comprising the antibody or its antigen-binding fragment and a pharmaceutically acceptable excipient.

In one embodiment, the pharmaceutical composition is a pharmaceutical composition for treating and/or preventing a disease, for example, cancer.

Another embodiment provides a method of detection of B7-H3 in a biological sample, comprising a step of contacting an antibody or antigen-binding fragment thereof as described herein with a biological sample requiring detection of B7-H3 expression.

The method may further comprise, after the step of contacting, a step of measuring an antigen-antibody response in the biological sample treated (contacted) with the antibody or antigen-binding fragment thereof.

In one embodiment, the method may be performed in vitro or in vivo.

In other embodiment, a kit comprising the antibody or its antigen-binding fragment or the composition comprising the antibody or antigen-binding fragment is provided. The kit may be provided as a kit for B7-H3 detection or a kit for administration for cancer treatment or a kit for cancer treatment, depending on a specific purpose for which the kit is used, and depending on its specific purpose, an additional component may be comprised. For example, a component for immunological analysis, for example, buffer and instructions for a kit for detection or diagnosis, or an apparatus for administration and instructions for a kit for antibody administration or cancer treatment may be further comprised.

The antibody or its antigen-binding fragment may (1) specifically recognize or bind to a B7-H3 expressed on a cell surface derived from human, mouse, or monkey or (2) specifically recognize or bind to an extracellular domain of B7-H3 which is not present on a cell surface.

The monoclonal antibody of the present invention shows both antibody-dependent cell-mediated cytotoxicity (ADCC) inducing capacity and immunocyte activation inducing capacity, and thereby it can inhibit death of a cancer cell or growth of cancer effectively through at least two mechanisms. Thus, the antibody showing high ADCC specific to B7-H3 may be usefully used for treatment of cancer through cancer cell-specific death, and it shows higher antibody-dependent cell-mediated cytotoxicity, compared to the conventional anti-B7-H3 antibodies, and therefore it can be effectively used for treatment of a cancer cell, replacing the conventional antibodies.

In addition, the monoclonal antibody of the present invention shows an effect as an immune checkpoint inhibitor which activates a T cell of which activity is degraded by an immune checkpoint ligand, B7-H3 protein, thereby being usefully used for cancer treatment through activation of immunocytes.

Furthermore, the antibody may be used for example, for drug delivery to specific cancer, etc., or detection, diagnosis and/or targeting of cancer by specific binding.

In addition, the monoclonal antibody disclosed herein has intraspecific cross-reactivity having the binding affinity to human, monkey and mouse B7-H3. This may be very useful for development of drugs, etc., compared to other human antibodies which do not show the binding affinity to mouse or monkey B7-H3. For example, the monoclonal antibody or various forms of therapeutic agents using the antibody can progress the development of drugs more economically and effectively by obtaining the initial result in a low cost of mouse model, before progressing a high cost of monkey-based experiment.

In order that an antibody to a specific antigen is used in vivo as an antibody for treatment, etc., it is a necessary factor to bind to a cell surface expression antigen. In case of some antibodies, they bind to a purified antigen, but do not bind to an antigen expressed on the cell surface. In this case, the antibody administered into a body cannot bind to a cell in the body and therefore it is not possible to act in vivo as an antibody for treatment, etc. Thus, this result shows that the anti-B7-H3 antibody of the present invention can bind to cell surface B7-H3 and show activity in vivo, thereby being usefully used as an antibody for treatment.

Figure 7:
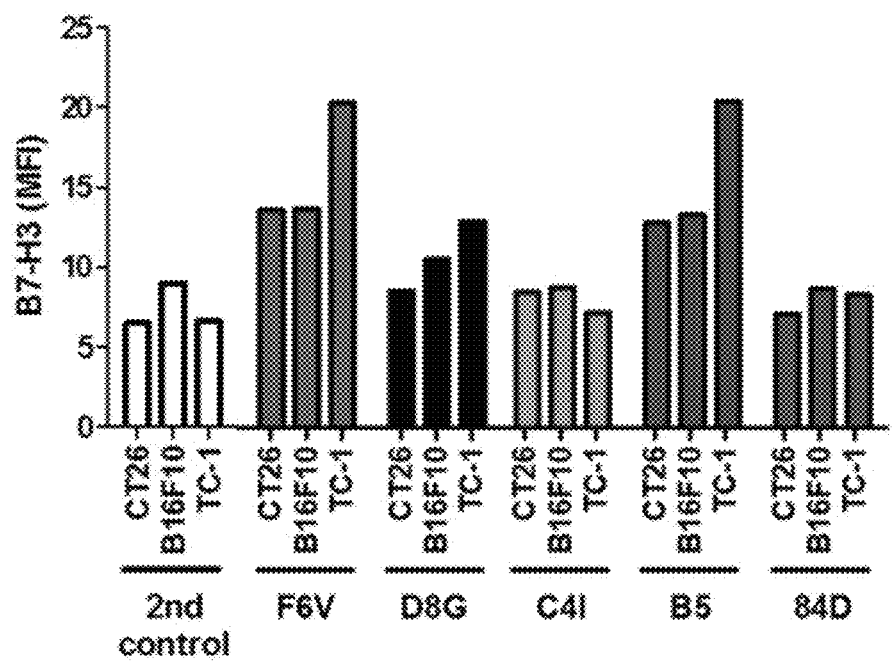

FIG. 7 is the result of measurement (FACS) for the binding capacity of the anti-B7-H3 antibody to mouse-derived cancer cell lines (CT26, B16F10, and TC-1). It was shown that every B7-H3 monoclonal antibody specifically recognized B7-H3 expressed on a surface of mouse-derived cancer cell lines, too.

Figure 8:
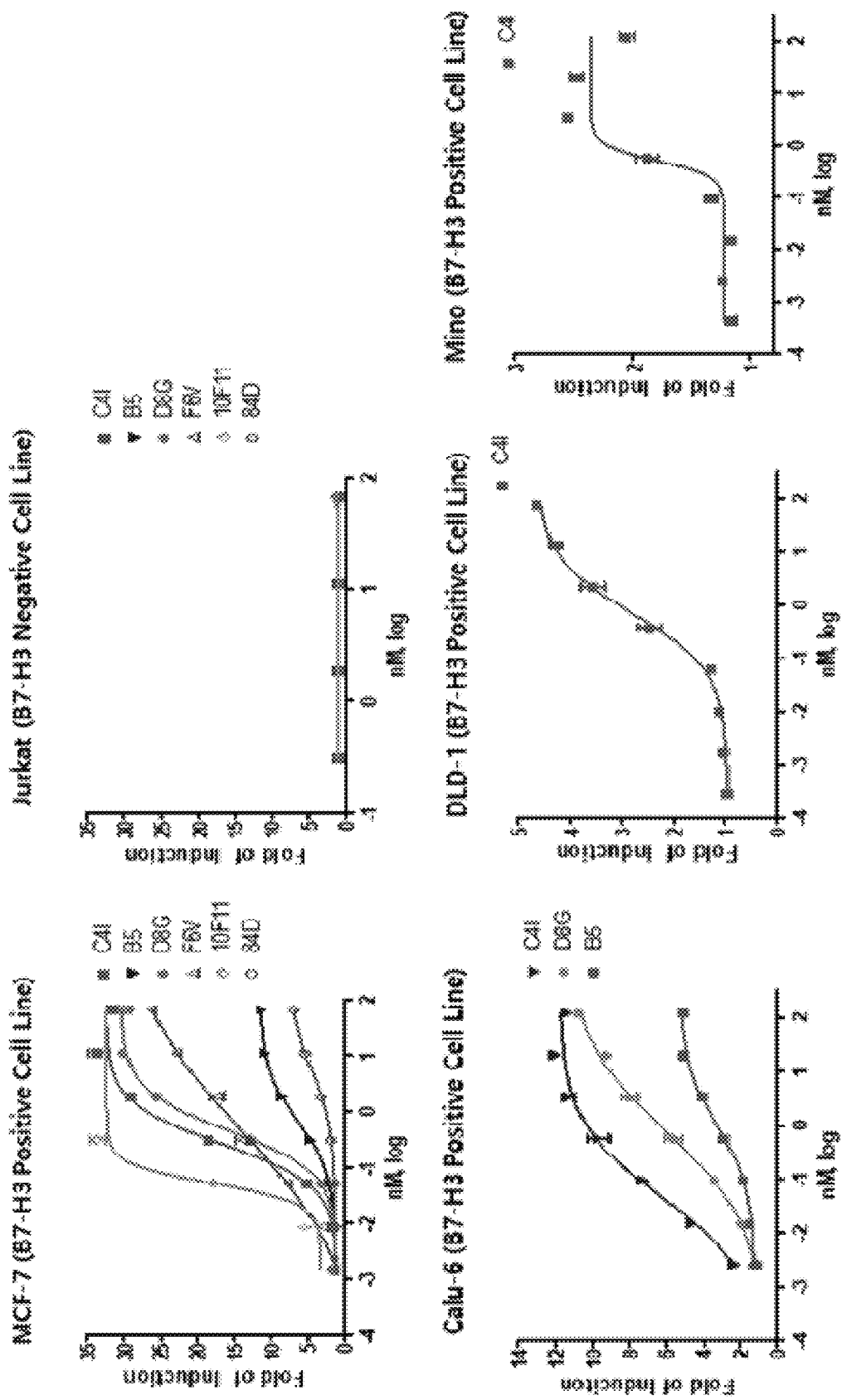

FIG. 8 is the result of measurement for the ADCC-inducing capacity of the anti-B7-H3 antibody prepared according to one embodiment of the present invention. The antibody prepared according to one embodiment of the present invention showed ADCC induction specific to human B7-H3 positive cell lines only, including MCF-7, Calu-6, DLD-1 and Mino. ADCC was not observed in the human B7-H3 negative cell line, Jurkat.

This shows that the antibody can be effectively used for death of cancer cells, since it specifically binds only to B7-H3 expressing cancer cells and induces antibody-dependent cell-mediated cytotoxicity. In particular, it shows that the anti-B7-H3 antibody of the present invention can be more effectively used for cancer treatment, since it has a lower EC50 and stronger strength of signal of antibody-dependent cell-mediated cytotoxicity, compared to the comparison antibody, 84D.

Figure 9A:
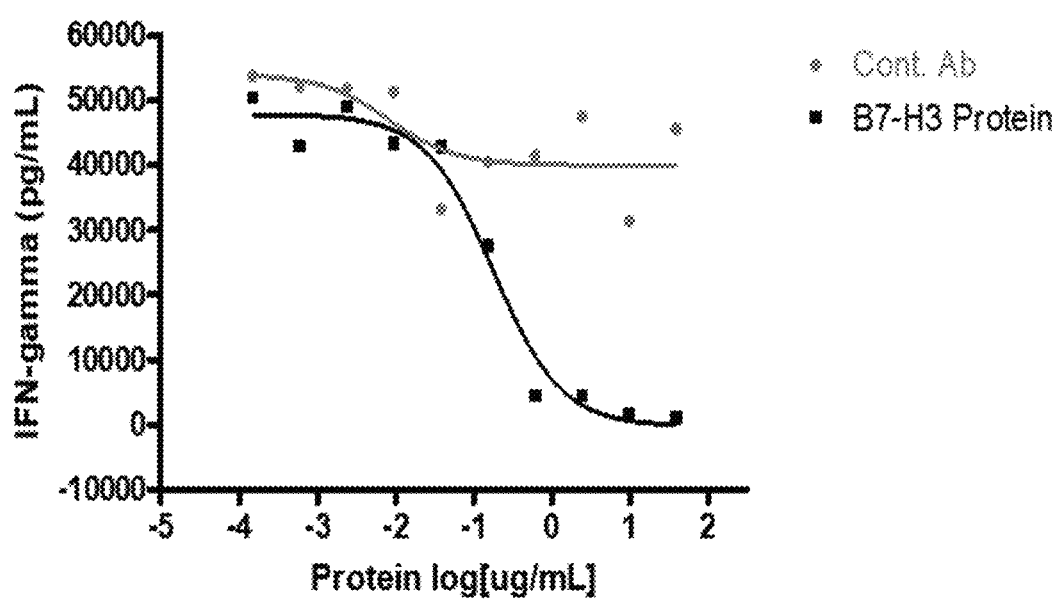

FIG. 9a shows the T cell activity inhibited by B7-H3 protein and the consequently inhibited production of interferon gamma. It was shown that the B7-H3 protein inhibited the production of interferon gamma in a concentration-dependent manner.

Figure 9B:
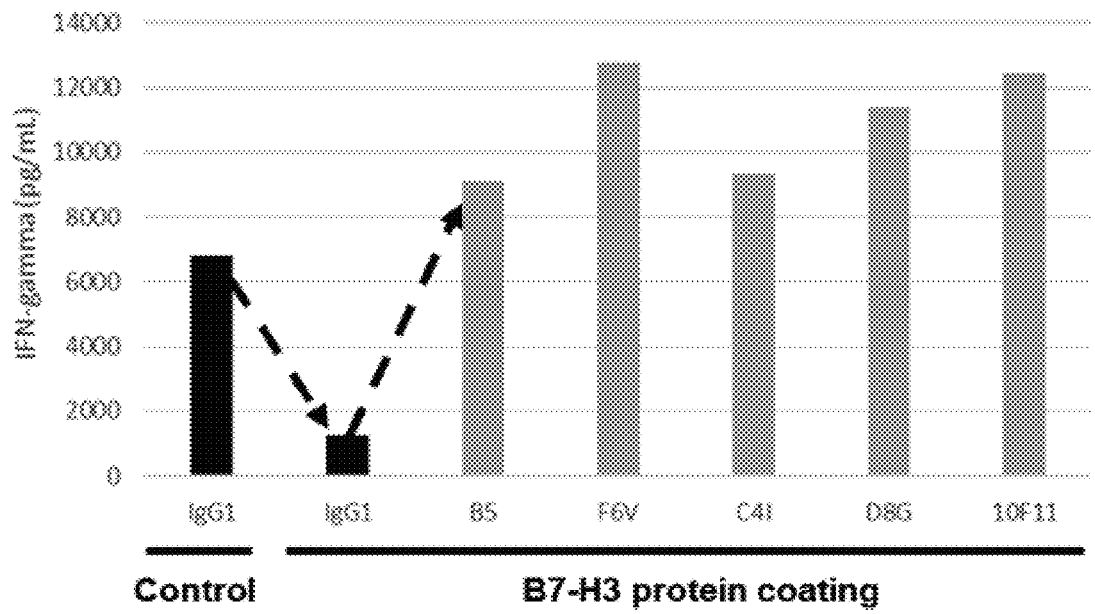
Figure 9B:
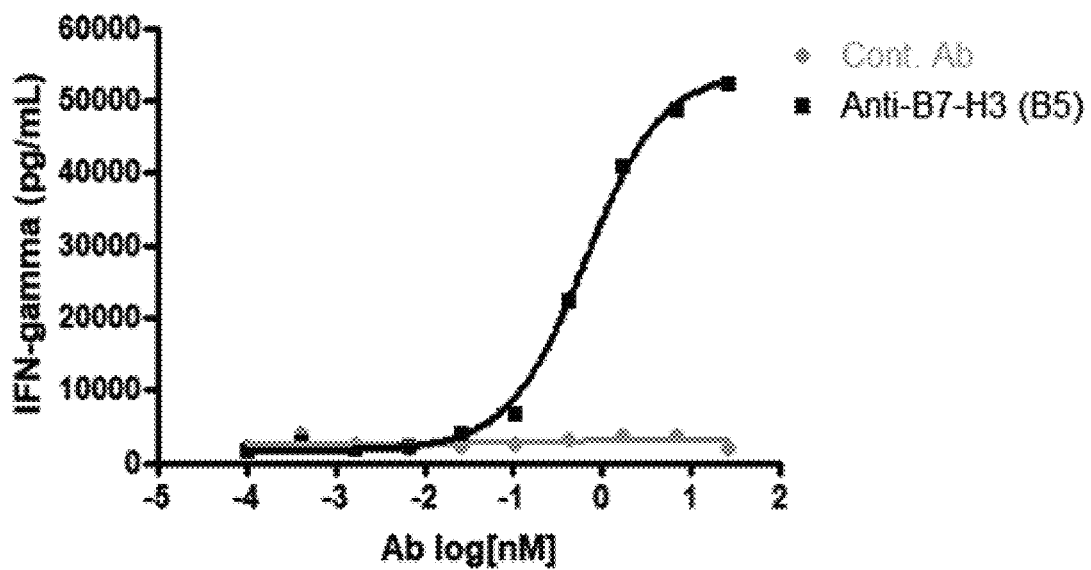

FIG. 9b shows that the anti-B7-H3 antibody prepared according to one embodiment of the present invention can reactivate a T cell activity as inhibited by B7-H3 protein as in FIG. 9a, which was measured by interferon gamma production. The results of FIG. 9a and FIG. 9b mean that the anti-B7-H3 monoclonal antibody of the present invention can neutralize or block immune-suppression of a T cell by B7-H3 protein. In other words, the B7-H3 antibody of the present invention can induce death of a cancer cell by a T cell by reactivating a T cell of which activity is inhibited, and this shows that the B7-H3 antibody of the present invention can be effectively used for cancer treatment.

Figure 10:
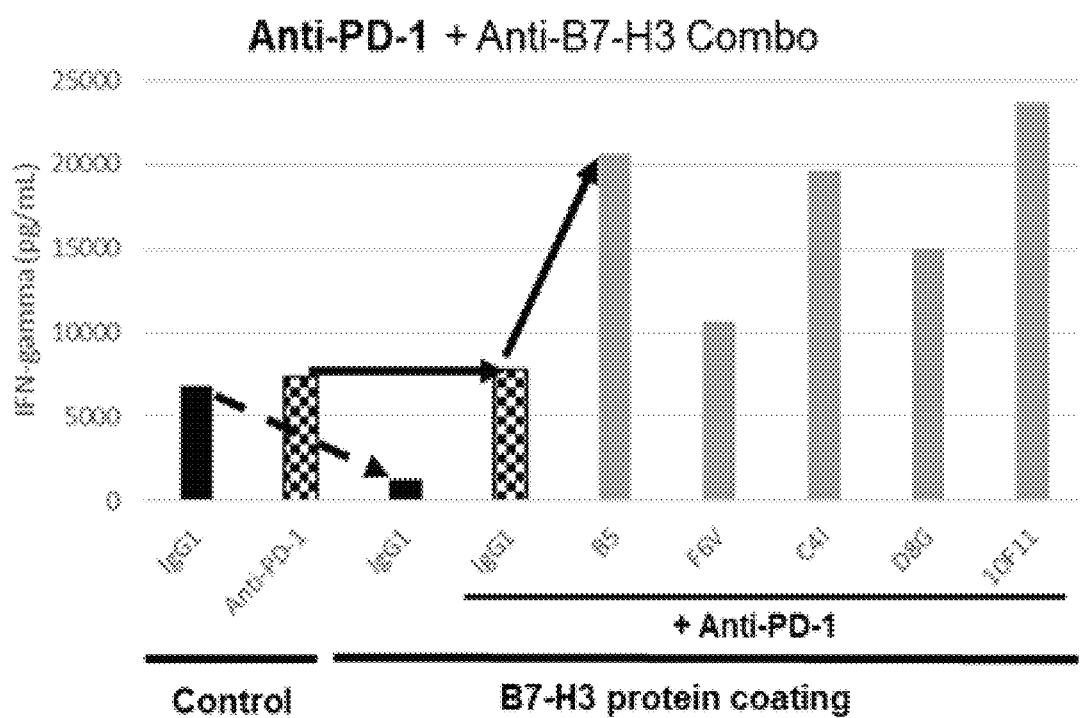

FIG. 10 shows an influence of the anti-B7-H3 antibody prepared according to one embodiment of the present invention on T cell activation by interferon, when used along with an anti-PD-1 antibody, which was measured by gamma production. It was shown that the anti-B7-H3 antibody, alone or with the anti-cancer immune antibody, effectively facilitates the production of interferon gamma by activating the T cell. This shows that the antibody may be effectively used for treatment of cancer by activating the T cell, alone or when combined with other anti-cancer immune antibody.

Figure 11:
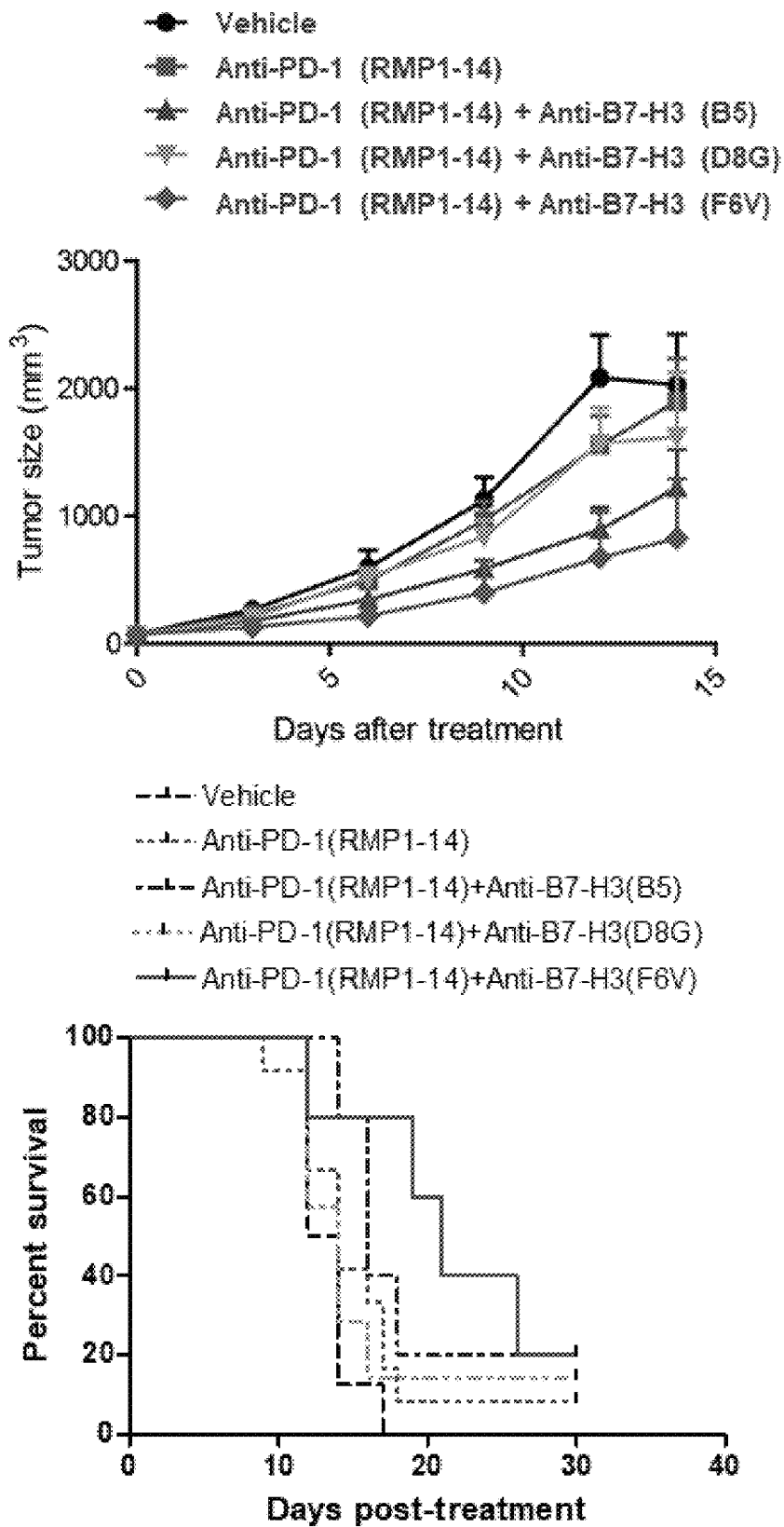

FIG. 11 is the result confirming that the tumor growth is inhibited and the survival rate is improved, when the anti-B7-H3 antibody prepared according to one embodiment of the present invention is co-administered with anti-PD-1 antibody in an isogenic tumor transplantation model in which CT26, a mouse B7-H3 positive cancer cell line, is transplanted. Anti-PD-L1 antibody acts through immune checkpoint inhibition. The result shows that the anti-B7-H3 antibody can be effectively used for treatment of cancer, when co-administered with anti-PD-1 antibody, improving survival rate.

Figure 12:
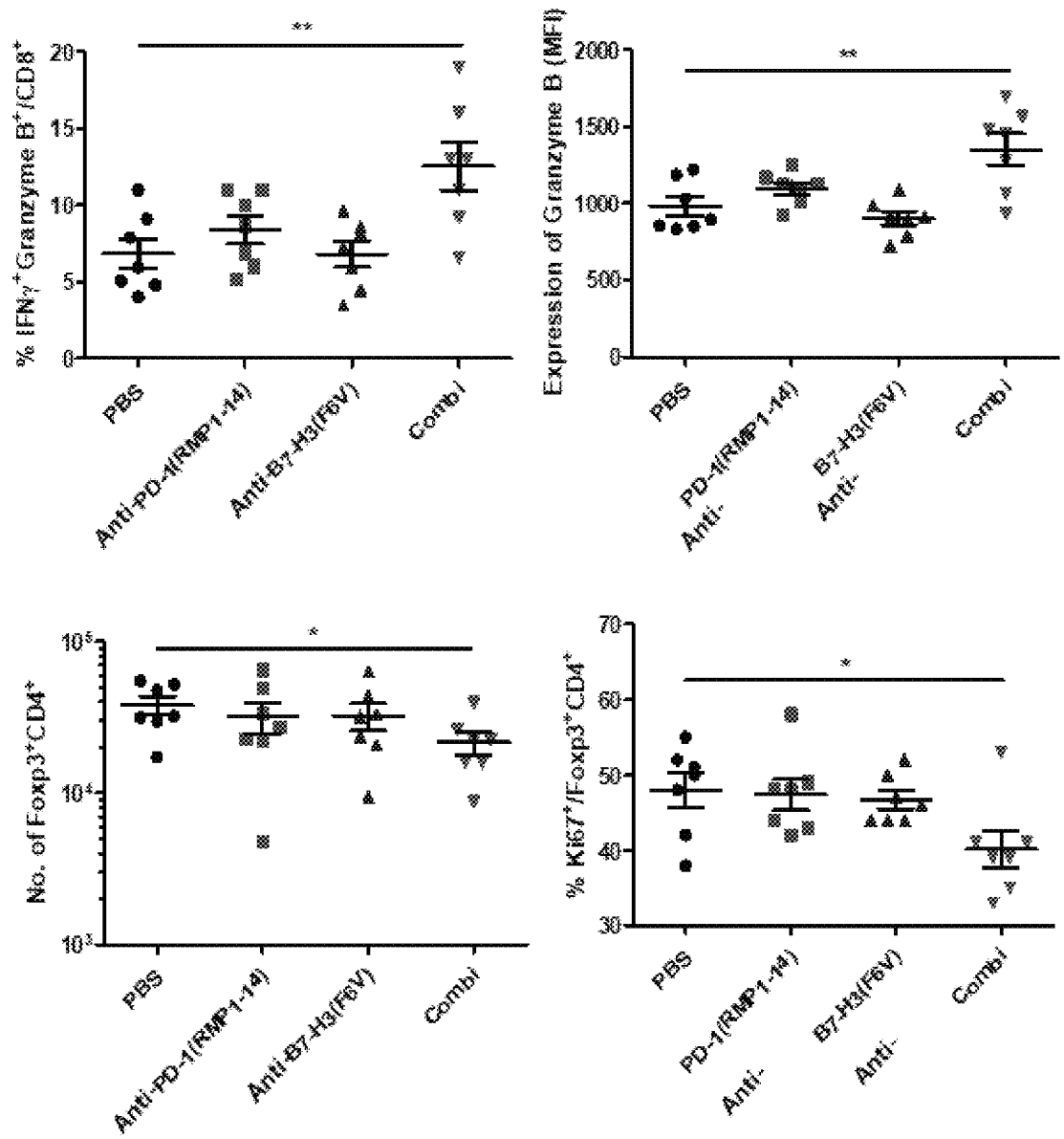

FIG. 12 is the result of analyzing the tumor-infiltrating lymphocytes flow in tumor, when the anti-B7-H3 antibody prepared according to one embodiment of the present invention is co-administered with anti-PD-a antibody in an isogenic tumor transplantation model in which CT26, a mouse B7-H3 positive cancer cell line, is transplanted. It was shown that the activity of CD8+ T cell is increased and the proliferation of a regulatory T cell is inhibited, by co-administration of the anti-B7-H3 antibody and anti-PD-1 antibody. This means that the anti-cancer effect by co-administration of the anti-B7-H3 antibody and the immune checkpoint inhibitor, anti-PD-1 antibody, appears through changes of the CD8+ T cell and regulatory T cell.

DETAILED DESCRIPTION OF THE INVENTION

The present invention is based on the development of an antibody which can specifically recognize an extracellular domain of B7-H3.

The titles used in the present section are for convenience of specification only, and do not limit the present invention.

Unless otherwise defined herein, the scientific and technical terms used herein have the same meaning as commonly understood by those skilled in the art. Further, unless the context specifically requires, the singular includes the plural, and the plural includes the singular.

All the amino acid sequences and nucleotide sequences described herein, that are represented by specific SEQ ID NOs, may comprise, consist essentially of, or consist of not only the sequences of the specific SEQ ID NOs, but also the sequences having at least 90%, at least 92%, at least 94%, at least 95%, at least 96%, at least 97%, at least 98%, or at least 99% identity with the sequences of the specific SEQ ID NOs, so long as they maintain their activities as anti-B7-H3 antibodies.

Definition

Herein, "polynucleotide" or "nucleic acid" includes a single or double strand nucleotide polymer. The nucleotide comprising such a polynucleotide may be a ribonucleotide or deoxyribonucleotide or their modified forms.

Unless otherwise stated herein, the left end of the polynucleotide stated herein is 5' end and its right end represents 3' end.

Herein, "isolated nucleic acid molecule" means DNA or RNA of genomic origin or mRNA, cDNA of synthetic origin or their combinations, which is linked to the polynucleotide that all or a portion of it is not associated with a polynucleotide present in nature, or it is not observed in nature. On the purpose of the present invention, the nucleic acid molecule comprising a specific nucleic acid sequence does not comprise an intact chromosome. Instead, the isolated nucleic acid molecule comprising a specific nucleic acid sequence may comprise at least several additional protein coding sequences, in addition to its specific sequence, or may further comprise a regulatory sequence and/or vector for expression of the specific nucleic acid sequence.

Herein, the term "regulatory sequence" means a polynucleotide sequence which can affect the expression and processing of a coding sequence by being operably connected thereto. This property of the regulatory sequence may be influenced by kinds of hosts. For example, the regulatory sequence applicable in a prokaryotic cell may include a promoter, occasionally an operator, a ribosome-binding site and a transcription termination sequence. In a eukaryotic cell, the regulatory sequence may comprise a promote comprising multiple recognition sites, a transcription enhancer, a polyadenylation sequence and a transcription termination sequence. The regulatory sequence may further comprise a reader sequence and/or a fusion partner sequence.

Herein, "vector" means any molecule used for delivering a nucleic acid molecule encoding a protein to a host cell, comprising for example, a nucleic acid, a plasmid, a bacteriophage or a virus.

Herein, "expression vector" means a vector which is suitable for transformation of a host cell and comprises a nucleic acid sequence that is operably connected to an expression vector and regulates the expression of heterologous sequences encoding a targeting protein. This expression vector may be also operably connected to the coding sequence, and in case of transcription, translation and that an intron is present, it may comprise a sequence regulating RNA splicing or affecting it.

Herein, "operably connected" means that nucleic acid sequences to be connected are positioned so as to perform a targeting function under an appropriate condition. For example, if the transcription of the coding sequence is affected by the regulatory sequence under an appropriate condition in a vector comprising a coding sequence and a regulatory sequence, it is operably connected.

Herein, "host cell" means a cell which can express a target gene that is transformed or to be transformed by a targeting nucleic acid sequence. The term includes progeny of the host cell, as long as expressing the targeting gene, regardless of identity of host cell and form and genetic makeup.

Herein, "transduction" commonly means movement of a nucleic acid from one bacterium to another bacterium by a bacteriophage. For example, it includes movement of a nucleic acid to a eukaryotic cell using a retrovirus which cannot replicate.

Herein, "transfection" means that a cell takes a foreign or exogenous DNA, and in this case, DNA is introduced in a cell through a cell membrane. This may refer methods known in the art, for example, Sambrook et al., Molecular Cloning: A Laboratory Manual, 4th ed., Cold Spring Harbor Laboratory Press, Cold Spring Harbor, N.Y. (2012), Ausubel et al., Current Protocols in Molecular Biology, Greene Publishing Associates.

Herein, "transformation" means a change of genetic properties of a cell, which are modified so that a cell comprises a new DNA or RNA. For example, a cell may be transformed as its genetic properties are changed, by introducing a new genetic material through transduction, transfection, or other techniques. The DNA transformed by methods including transduction or transfection, etc. may be present by being physically integrated in a chromosome of a cell, or may be temporarily present as an episome form without replication or a replicable plasmid. When the transformed DNA is replicated with division of a host cell, it is considered as stably transformed.

Herein, "amino acid" includes the common meaning understood in the art. Twenty natural-occurring amino acids and their abbreviations are as those commonly used in the art (Immunology-A Synthesis, 2nd Edition, E. S. Golub and D. R. Green, eds., Sinauer Associates: Sunderland, Mass. 1991). The amino acid includes typical amino acids, stereoisomers of typical 20 amino acids (D-amino acids), non-natural amino acids, for example, α-,α-disubstituted amino acids, N-alkyl amino acids, and other non-typical amino acids. As examples of non-typical amino acids, 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine and other similar amino acids and imino acids (for example, 4-hydroxyproline). In the mark of polypeptide used herein, as commonly used in the art, the left of a sequence is an amino terminal and the right represents a carboxy terminal.

Herein, "polypeptide" or "protein" means a polymer of an amino acid residue, and it is used interchangeably herein. This also includes not only polymers of naturally occurring amino acid residues but also polymers of their analogues or mimetics. In addition, the polypeptide or protein may comprise modification such as addition of carbohydrates for phosphorylation or glycosylation, etc. Moreover, the polypeptide or protein may be produced in a recombinant or naturally found cell. Furthermore, the polypeptide or protein may include those in which a portion of a wild type sequence or the amino acid sequence is deleted, added and/or substituted. In addition, the polypeptide or protein includes an antibody, for example, an anti-B7-H3 antibody (or named as B7-H3 antibody), B7-H3 binding protein, or an antigen-binding fragment, or a sequence in which one or more amino acids are deleted, added and/or substituted. Moreover, "polypeptide fragment" means a polypeptide having deletion of an amino acid sequence of an amino terminal, deletion of an amino acid sequence of a carboxyl terminal and/or an internal deletion, compared to a full-length protein. This fragment may also include modified amino acids compared to a full-length protein. In one embodiment, the fragment may be about 5 to 900 amino acids in length, for example, at least 5, 6, 8, 10, 14, 20, 50, 70, 100, 110, 150, 200, 250, 300, 350, 400, 450, 500, 550, 600, 650, 700, 750, 800, 850 or more amino acids in length. Considering the purpose of the present invention, the useful polypeptide fragment includes an immunological functional fragment of an antibody comprising an antigen-binding domain. In case of B7-H3 binding antibody, such a useful fragment includes a CDR sequence comprising 1, 2, or 3 of heavy chains or light chains, or all or a portion of antibody chain comprising a variable region or constant region of a heavy chain or light chain, but not limited thereto.

Herein, "isolated polypeptide, antibody or protein" is that there is not any other protein to be found together with them commonly and at least about 50% or more of lipids, carbohydrates and polynucleotides naturally connected to them are removed. Typically, the isolated protein, polypeptide or antibody comprises at least about 5%, at least about 10%, at least about 25% or at least about 50%, in a certain composition. This polypeptide may be encoded by genome DNA, cDNA, mRNA or other RNA of synthetic origins or any combinations thereof. In particular, the isolated protein, polypeptide or antibody is substantially free of contaminants of other proteins or other polypeptides, which interfere with its therapeutic, diagnostic and prophylactic researches or application for other uses.

Herein, "variant" of a polypeptide such as for example, an antigen-binding fragment, a protein or an antibody is a polypeptide in which one or more amino acid residues are inserted, deleted, added and/or substituted, as compared to another polypeptide sequence, and includes a fusion polypeptide. In addition, a protein variant includes one modified by protein enzyme cutting, phosphorylation or other post-translational modification, but maintaining biological activity of the antibody disclosed herein, for example, specific binding to B7-H3 and biological activity. The variant may be about 99%, 98%, 97%, 96%, 95%, 94%, 93%, 92%, 91%, 90%, 89%, 88%, 87%, 86%, 85%, 84%, 83%, 82%, 81%, or 80% identical to the sequence of the antibody or its antigen-binding fragment disclosed herein. The percent identity (%) or homology may be calculated with reference to the following description.

In one embodiment, the percent homology or identity may be calculated as $100 \times [(\text{identical position})/\min(TG_A, TG_B)]$, and in the formula, $TG_A$, $TG_B$ are the sum of the number of residues of sequences A and B compared and the internal gap position (Russell et al., J. Mol Biol., 244: 332-350 (1994).

Herein, the conservative amino acid substitution means the substitution which does not substantially affect the activity or antigenicity of a polypeptide. The polypeptide may comprise one or more conservative substitutions. Non-limiting examples are disclosed in the following Table 3.

The "derivative" of the polypeptide herein means a polypeptide chemically modified through conjugation with other chemical moiety, which is different from an insertion, deletion, addition or substitution variant.

Herein, the term "naturally found" used with regard to a polypeptide, nucleic acid, host cell, etc. means a material present naturally.

The B7-H3 (B7 Homolog 3, CD276), that is recognized by the antibody or antigen-binding fragment thereof described herein, may refer to a transmembrane protein of a B7 family belonging to an immunoglobulin (Ig) superfamily, and comprises an extracellular domain, a transmembrane domain and an intracellular domain. The B7-H3 which the antibody recognizes may be an extracellular domain which is present in a cell membrane or is not present in a cell membrane. The human protein of B7-H3 consists of 534 amino acids, and it is disclosed as NCBI Reference Sequence: NP_001019907.1. Unless apparent from the context used herein, the B7-H3 refers to a human B7-H3, but the antibody has the binding capacity to monkey and mouse B7-H3 specifically. The monkey B7-H3 protein consists of 534 amino acids, and is disclosed as NCBI Reference Sequence: XP_005560056.1. The mouse B7-H3 protein consists of 316 amino acids, and is disclosed as NCBI Reference Sequence: NP_598744.1.

Herein "identity" or homology means the sequence similarity of two or more polypeptides or two or more polynucleotides, which are determined by arranging and comparing two or more polypeptides or two or more polynucleotides. This identity between sequences is commonly represented by "identity percent", and this means the ratio of identical amino acids or nucleotides between molecules to be compared, and it is calculated on the basis of the smallest size of molecule, among molecules to be compared. The following documents may be referred for methods to be used for calculating the identity between many molecules by arranging nucleic acids or polypeptides: *Computational Molecular Biology*, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, *SIAM J. Applied Math.* 48:1073.

When the identity percent is calculated, sequences to be compared are arranged in the way of providing the maximum matching between sequences, and in the arranged sequences, gap, matching and mis-match may be present, and this is treated by a specific mathematical model or a computer algorithm. In one embodiment, this identity percent may be determined using a GCG program package including a GAP program which arranges two sequences in the way of maximizing the match between sequences to be compared and minimizing the number of gaps, using Needlman and Wunsch algorithm (Devereux et al., 1984, *Nucl. Acid Res.* 12:387; Genetics Computer Group, University of Wisconsin, Madison, WI, USA). The computer algorithm GAP determines "matching span" by arranging two sequences in the way of maximizing the match between them and minimizing the number of gaps in two polypeptide or polynucleotide sequences to be compared. The algorithm also uses a gap opening penalty [this is calculated as 3× average diagonal, wherein "average diagonal" is the average of diagonals of comparison matrix to be used; and "diagonal" is a score or number assigned for each complete amino acid match by a specific comparison matrix] and a gap extension penalty (this is commonly ⅒ fold of the gap opening penalty), and a comparison matrix, for example, PAM 250 or BLOSUM 62 together. In a specific embodiment, a standard comparison matrix (refer to Dayhoff et al., 1978, *Atlas of Protein Sequence and Structure* 5:345-352 for PAM 250 comparison matrix; refer to Henikoff et al., 1992, Proc. Natl. Acad. Sci. U.S.A. 89:10915-10919 for BLOSUM 62 comparison matrix) is used. In one embodiment, parameters recommended for determining the identity percent of polypeptides or polynucleotides in which the GAP program is used are as follows: algorithm: Needleman et al., 1970, J. Mol. Biol. 48:443-453; comparison matrix: BLOSUM 62 (Henikoff et al., 1992, supra); gap penalty: 12 (no penalty for a terminal gap); gap length penalty: 4; similarity threshold: 0.

When two sequences are arranged using specific parameters, although there is no significant relation between two sequences, the result that they are matched with high identity in a short sequence region may be derived. In this case, in order that two sequences are arranged through at least 50 sequential amino acids, parameters of the algorithm used as the GAP program can be corrected.

"Substantially pure" used herein is that a targeting molecule is present as a predominant species. In other words, it means that on the basis of mole, the concentration is higher than any other individual species in the same mixture. In one embodiment, a substantially pure molecule is comprised as at least about 50% (based on mole), at least about 80%, about 85%, at least about 90%, or at least about 99%, among all polymers comprised in a composition. In other embodiment, the targeting molecule is substantially homogeneously purified until any more contaminants are not detected by using a conventional method, and therefore the composition comprises one kind of homogeneous polymer material.

In one aspect, the present invention relates to a recombinant antibody specifically binding to a B7-H3 protein or its antigen-binding fragment. In this aspect, "recombinant protein" is a protein prepared using a recombination technique, namely, through the expression of the recombinant nucleic acid described in the present invention. The methods and techniques for production of a recombinant protein are widely known in the art.

Herein, "affinity" is the strength of interaction between an antibody or its antigen-binding fragment and an antigen, and it is determined by properties of the antigen such as size, shape and/or charge of antigen, and CDR sequences of the antibody or antigen-binding fragment. The methods for determining the affinity are known in the art, and the followings can be referred.

The antibody or its antigen-binding fragment is called "specifically binding" to its target such as an antigen, when a dissociation constant ($K_D$) is ≤$10^{-6}$ M. The antibody specifically binds to a target with "high affinity", when $K_D$ is ≤$1 \times 10^{-8}$ M.

Herein, "antigen-binding region or site" means a protein or a part of protein specifically binding to a specific antigen. For example, a part of an antibody comprising an amino acid residue providing the antibody with specificity and affinity to an antigen, by interacting with the antigen. This antigen-binding region typically comprises one or more "complementary determining regions (CDR)". A specific antigen-binding region also comprises one or more "framework" regions. The framework region helps to maintain an appropriate conformation of these CDRs, thereby facilitating binding between the antigen-binding region and an antigen.

Herein, "antibody" means an antigen-binding fragment which can compete to an intact antibody for binding to any isotype of intact immunoglobulin, or a target antigen. For example, it includes chimeric, humanized, complete human and multi-specific antibodies or their antigen-binding fragments. The antibody is one kind of antigen binding proteins by itself. The intact antibody commonly comprises at least 2 full-length heavy chains and 2 full-length light chains, but in some cases as naturally found in Camelid animals, the antibody may comprise only heavy chains. The antibody or its antigen-binding fragment may be derived from only one source or chimeric. The chimeric antibody comprises a part derived from two kinds of different antibodies, and is described in more detail below. The antibody or its antigen-binding fragment can be produced by hybridoma, recombinant DNA technique or enzymatic or chemical cutting of an intact antibody. Unless otherwise stated, herein, the term, antibody includes an antibody comprising 2 full-length heavy chains and 2 full-length light chains, and its derivatives, variants, fragments, and mutants, and their examples are as described below.

Herein, "light chain" includes a full-length light chain having a variable region sequence enough to provide binding specificity to an antigen or epitope and its fragment. The full-length light chain comprises a variable region domain VL and a constant region domain CL. The variable region domain of light chain is present in an amino terminal of a light chain polypeptide. The kinds of light chains include kappa and lambda chains.

Herein, "heavy chain" includes a full-length heavy chain having a variable region sequence enough to provide binding specificity to an antigen or epitope and its fragment. The full-length heavy chain comprises a variable region domain VH and 3 constant region domains CH1, CH2 and CH3. The VH domain is present in an amino terminal of a heavy chain polypeptide and the CH domain is present in a carboxy terminal, and the CH3 is positioned closest to a carboxy terminal. The heavy chain comprises IgG (comprising IgG1, IgG2, IgG3 and IgG4 subtypes), IgA (comprising IgA1 and IgA2 subtypes), and isotypes of IgM and IgE.

Used herein, "antigen-binding fragment" of a chain (heavy chain or light chain) of an antibody or immunoglobulin includes a part of an antibody which lacks some amino acids compared to a full-length chain, but can specifically bind to an antigen. This fragment can be considered as having biological activity, in an aspect that it can specifically bind to a target antigen, or can compete to other antibodies or an antigen-binding fragment to bind a specific epitope. In one aspect, this fragment comprises at least one CDR present in a full-length light chain or heavy chain, and in some embodiments, it comprises a short-chain heavy chain and/or light chain, or its part. This biological active fragment may be produced by a recombinant DNA technique or may be produced for example, by cutting an intact antibody enzymatically or chemically. An immunologically functional immunoglobulin fragment includes Fab, Fab', F(ab')2, scFab, dsFv, Fv, scFV, scFV-Fc, diabody, minibody, scAb, and dAb, but not limited thereto. In addition, it may be derived from any mammal including human, mouse, rat, camelid or rabbit, but not limited thereto. The functional part of the antibody such as one or more CDRs described herein may be linked with a secondary protein or small molecular compound by a covalent bond, thereby being used as a target therapeutic agent to a specific target.

Herein, "Fc" region comprises two heavy chain fragments comprising CH2 and CH3 domains of an antibody. These 2 heavy chain fragments are combined each other by hydrophobic interaction of two or more of disulfide bonds and CH3 domain.

Herein, "Fab fragment" consists of 1 light chain and 1 heavy chain comprising CH1 and a variable region only. The heavy chain of Fab molecule cannot form a disulfide bond with other heavy chain molecule.

Herein, "Fab' fragment" comprises a region between CH1 and CH2 domains of a heavy chain, in addition to Fab fragment, and it can form a disulfide bond between two heavy chains of two molecules of Fab' fragment, to form a F(ab')$_2$ molecule.

Herein, "F(ab')2 fragment" comprises two light chains, and two heavy chains comprising a variable region, CH1 and a part of a constant region between CH1 and CH2 domains, as aforementioned, and thereby an intrachain disulfide bond between 2 heavy chains is formed. Thus, the F(ab')2 fragment consists of two Fab' fragments, and the two Fab' fragments are meeting each other by the disulfide bond between them.

Herein, "Fv region" is an antibody which comprises each variable region of a heavy chain and a light chain, but does not comprise a constant region. scFc is one that Fv is linked by a flexible linker. scFv-Fc is one that Fc is linked to scFV. The minibody is one that CH3 is linked to scFV. The diabody comprises two molecules of scFV.

Herein, "short-chain antibody (scAb)" is a single polypeptide chain comprising one variable region of a heavy chain or a light chain constant region in which a heavy chain and light chain variable region is linked by a flexible linker. The short-chain antibody may refer to for example, U.S. Pat. No. 5,260,203, and this is disclosed herein by reference.

Herein, "domain antibody (dAb)" is an immunologically functional immunoglobulin fragment comprising a variable region of heavy chain or a variable region of light chain only. In one embodiment, two or more of VH regions are linked by a covalent bond by a peptide linker, to form a bivalent domain antibody. Two VH regions of this bivalent domain antibody may target the same or different antigen.

Herein, "bivalent antigen-binding protein" or "bivalent antibody" comprises 2 antigen-binding sites. Two antigen-binding sites comprised in this bivalent antibody may have the same antigen specificity or may be a dual-specific antibody binding to different antigens separately.

Herein, "multi-specific antigen-binding protein" or "multi-specific antibody" is targeting two or more of antigens or epitopes.

Herein, "bispecific", "dual-specific" antigen-binding protein or antibody is a hybrid antigen-binding protein or antibody having 2 different antigen-binding sites. This bispecific antibody is one kind of multi-specific antigen-binding protein or multi-specific antibody, and it can be produced by known various methods, for example, fusion of hybridoma or linking of Fab' fragment. For example, Songsivilai and Lachmann, 1990, *Clin. Exp. Immunol.* 79:315-321; Kostelny et al., 1992, *J. Immunol.* 148:1547-1553, etc. may be referred. The 2 epitopes different each other to which 2 antigen-binding sites of the bispecific antigen-binding protein or antibody bind may be positioned on the same or different protein target.

Herein, the term "antigen" or "immunogen" means a molecule or a part of molecule which for example, an antigen-binding protein (for example, antibody or its immunologically functional antigen-binding fragment) can bind to, and can be used for production of an antibody which can bind to an antigen in an animal. The antigen may comprise one or more of epitopes which can interact with a different antibody or its fragment. In one embodiment, the antigen is an extracellular domain of a B7-H3 protein. In other embodiment, the antibody can recognize all of the extracellular domain of B7-H3 which is not present on a cell surface, or B7-H3 in a form present on a cell membrane.

Herein, "epitope" is a part of molecule which is bound by an antigen-binding protein or antibody or is recognized by them, and comprise any determining factor which can specifically bind to an antigen-binding protein, such as for example, an antibody or a T-cell receptor. The epitope may be sequential or unsequential, and for example, in a polypeptide sequence, it is not sequential each other, but in an aspect of molecule, like a conformational epitope, it may be an amino acid residue that is bound by one antigen-binding protein, but is not sequential and is positioned away each other. In one embodiment, the epitope comprises a three-dimensional structure similar to an antigen used for antibody production, but it may be a mimetic in an aspect that it can comprise no residue found in the epitope or can comprise some residues only. Commonly, the epitope is a protein, but it may be other kinds of materials such as a nucleic acid. The epitope determining factor may be a chemically active group formed on a surface by a molecule such as an amino acid, a sugar side chain, a phosphoryl group or a sulfonyl group, or may have specific three-dimensional structural properties and/or specific charge properties. Commonly, an antibody which is specific to a specific target antigen recognizes an epitope of a target antigen which is present in a complex of a protein and/or a polymer.

Herein, "therapeutic agent" means a molecule to be administered to a subject for a targeting therapeutic effect. The subject includes a non-human mammal, for example, primates, or a human. The example of the therapeutic agent includes a protein comprising a peptide and a polypeptide, a nucleic acid, an antibody or a small molecular compound. In other aspect, the therapeutic agent can be used as a therapeutic agent of related diseases such as cancer, by being bound to the antibody, or the antibody.

Herein, the term "treating" means alleviation or treatment of an injury, disease, or symptom of disease or morbid condition, including any objective or subjective parameters, including reduction, relief, alleviation of an injury, disease, or symptom of disease or condition, or making a patient better able to withstand an injury, disease, or symptom of disease or morbid condition, slowing the deteriorating rate of an injury, disease, or symptom of disease or morbid condition, or improving the quality of life of a patient mentally or physically. This treatment or improvement of an injury, disease, or symptom of disease or morbid condition may be judged on the basis of results of physical examination, examination of various indexes related to a disease and imaging examination.

Herein, "effective dose" commonly means an amount enough to reduce seriousness and/or occurrence frequency of symptoms due to a disease, particularly, a disease related to B7-H3, remove symptoms due to a disease, particularly, a disease related to B7-H3 and/or a root cause of disease occurrence, or prevent occurrence of symptoms due to a disease, particularly, a disease related to B7-H3 and/or a root cause, and/or improve or correct damages due to a disease, particularly, a disease related to B7-H3. In some embodiments, the effective dose is a therapeutic effective dose or a prophylactic effective dose. The "therapeutic effective dose" is an amount enough to treat a disease, particularly symptoms or conditions related to B7-H3, or prevent, delay a disease, particularly symptoms or conditions related to B7-H3, or reverse its progress.

The "prophylactic effective dose" is an amount for prevent or delay occurrence or reoccurrence of a disease, particularly, a disease related to B7-H3, or symptoms related to a disease, particularly, a disease related to B7-H3, and reduce its probability. The complete therapeutic or prophylactic effect can be caused by several times of administration of dose, rather than by a single administration of dose.

Therefore, the therapeutic or prophylactic effective dose may be delivered by once or more of administration.

Antibody or Antigen-Binding Fragment

The present invention discloses an antibody specifically binding to an extracellular domain of B7-H3 protein, or its antigen-binding fragment. The antibody or antigen-binding fragment has cross-reactivity to an extracellular domain of mouse and monkey B7-H3 protein.

The antibody disclosed herein, is a polypeptide comprising one or more of complementary determining regions or sites (CDR), as disclosed herein.

In some embodiments, a CDR is comprised in a "framework" region, and the framework orients a CDR(s) so that this CDR(s) can have appropriate antigen-binding properties.

The antibody specifically binds to a human, monkey and mouse-derived B7-H3 extracellular domain, and it can specifically bind to an isolated form of extracellular domain or an extracellular domain of B7-H3 expressed on a cell surface.

In one embodiment, the antibody includes a monoclonal antibody, dual-specific antibody, double antibody, multi-specific antibody, multiple antibody, minibody, domain antibody, antibody mimetic (or synthetic antibody), chimeric antibody, humanized antibody or antibody fusion (or antibody conjugate) and fragment thereof, but not limited thereto, and includes various forms of antibodies disclosed herein.

In one embodiment, the antibody fragment of the antibody disclosed herein may be Fab, Fab', F(ab')2, scFab, Fv, dsFv, scFV, scFV-Fc, minibody, diabody, scab, or dAb.

In other embodiment, the antibody disclosed herein may consist of a polypeptide of only light chains or only heavy chains comprising variable regions disclosed in Table 2a and Table 2b.

One antibody disclosed herein shares a specific region or sequence with another antibody disclosed herein. In one embodiment, it may share a constant region of the antibody or antigen-binding fragment. In another embodiment, it may share an Fc region. In another embodiment, it may share a frame of variable region.

In one embodiment, the antibody has a typical structure of an antibody found in nature. Camelid animals produces an antibody consisting of a single heavy chain, but the structural unit of this antibody commonly comprises a tetrameric polypeptide, and the tetramer comprises two of one pair of polypeptide chain bodies consisting of different 2 polypeptide chains. In a typical antibody, the one pair of polypeptide chain body comprises one full-length light chain (about 25 kDa) and one full-length heavy chain (about 50 to 70 kDa). Each chain shows a characteristic folding pattern, and consists of several immunoglobulin domains, consisting of about 90 to 110 amino acids. These domains are basic units consisting of an antibody polypeptide. The amino-terminal part of each chain typically comprises a part called a variable region or V region that is a part recognizing an antigen. The carboxy-terminal part is conserved evolutionarily more than the amino-terminal, and it comprises a part called a constant region or C region. The human light chain is commonly classified as kappa (κ) and lambda (λ) light chains, and these comprise one variable region and one constant region, respectively. The heavy chain is typically classified as mu (μ), delta (δ), gamma (γ), alpha (α) or epsilon (ε) chain, and these are defined as IgM, IgD, IgG, IgA and IgE isotypes, respectively. IgG includes IgG1, IgG2, IgG3 and IgG4, but has unlimited numerous subtypes. IgM subtype includes IgM and IgM2. IgA subtype includes IgA1 and IgA2. In human, IgA and IgD isotypes comprise 4 heavy chains and 4 light chains; IgG and IgE isotypes comprise 2 heavy chains and 2 light chains, and IgM isotype comprises 5 heavy chains and 5 light chains. The heavy chain constant region typically shows an effector function, but comprises one or more domains. The number of heavy chain constant region domains becomes different depending of isotypes. IgG heavy chain, for example, comprises 3 C region domains known as $C_H1$, $C_H2$ and $C_H3$, respectively. The antibody disclosed herein may be any one of these isotypes and subtypes. In one embodiment, the antibody is an IgG1, IgG2a, IgG2b, IgG3 or IgG4 subtype. In a further embodiment, the antibody of the present invention is an IgG1- or IgG2-type. In a further embodiment, the antibody of the present invention is an IgG1-type.

The heavy chain variable region and light chain variable region may be linked to at least a part of a human constant region. The selection of a constant region may be determined by whether the antibody-dependent cell-mediated cytotoxicity, antibody-dependent cell phagocytosis, and/or complement-dependent cytotoxicity is required partially. For example, human isotype IgG1 and IgG3 have complement-dependent cytotoxicity and human isotype IgG2 and IgG4 do not have this cytotoxicity. In addition, human IgG1 and IgG3 induce a cell-mediated effector function stronger than human IgG2 and IgG4. The light chain constant region may be lambda or kappa.

In other embodiment, the antibody provided by the present invention may be a human antibody, and the heavy chain constant region may be an IgG1-, IgG2- IgG3- or IgG4-type. In a further embodiment, the antibody of the present invention is an IgG1- or IgG2-type.

In other embodiment, the antibody provided by the present invention is a human antibody has cross-reactivity to mouse and monkey.

In full-length light chain and heavy chain, a variable region and a constant region are linked by "J" region that is about 12 or more of amino acids in length, and the heavy chain also comprises "D" region of about 10 or more of amino acids. For example, Fundamental Immunology, 2nd ed., Ch. 7 (Paul, W., ed.) 1989, New York: Raven Press may be referred. Typically, a variable region of light chain/heavy chain pair of an antibody forms an antigen-binding site.

A variable region of an immunoglobulin chain has the same overall structure commonly, and comprises a comparatively conserved framework region (FR) connected by 3 hypervariable regions called "complementary determining site or region or domain" or CDR (Complementary Determining Region). The CDR of a variable region derived from each chain consisting of heavy chain/light chain pair is arranged by a framework region typically, thereby forming a structure specifically binding to a specific epitope of a target protein. These factors of naturally occurring light chain and heavy chain regions are typically comprised from the N-terminal to the C-terminal in the following order: FR1, CDR1, FR2, CDR2, FR3, CDR3 and FR4. The position of amino acid sequences corresponding to each of them in the variable region may be determined by Kabat (Kabat et al., (1983) U.S. Dept. of Health and Human Services, "Sequences of Proteins of Immunological Interest"), Chothia (Chothia and Lesk, J. Mol. Biol. 196:901-917 (1987)) or a method related to OPAL library (Hye Young Yang et. al., 2009 Mol. Cells 27: 225). The CDRs determined by each definition may be a subset which is over-lapped or that one comprises the other, when comparing each other. However, herein, all CDRs to be defined by each method are included in the scope of the present invention.

Those skilled in the art will easily select a CDR sequence by each definition among them, when the sequence of variable region of an antibody is provided.

CDR sequences to be comprised in heavy chain and light chain variable regions of the antibody or antigen-binding fragment according to one embodiment of the present invention are disclosed in Table 1a to Table 1f, respectively.

TABLE 1a

| CDRH1 | |
|---|---|
| Sequence | SEQ ID NO |
| DYAMS | 1 |
| GYYMS | 2 |
| SYSMS | 3 |
| SYGMS | 4 |

TABLE 1b

| CDRH2 | |
|---|---|
| Sequence | SEQ ID NO |
| SISSGSGSIYYADSVKG | 5 |
| LISPSSGSIYYADSVKG | 6 |
| GIYSDGSNTYYADSVKG | 7 |
| GISPGGSNTYYADSVKG | 8 |
| GIYSGGSSKYYADSVKG | 9 |
| GIYSDASNTYYADSVKG | 68 |

TABLE 1c

| CDRH3 | |
|---|---|
| Sequence | SEQ ID NO |
| NLIPLDY | 10 |
| GLTKFDY | 11 |
| MLHRFDY | 12 |
| DAWIARLLLFDY | 13 |
| NRLRFDY | 14 |

TABLE 1d

| CDRL1 | |
|---|---|
| Sequence | SEQ ID NO |
| SGSSSNIGSNAVS | 15 |
| TGSSSNIGSNDVS | 16 |
| SGSSSNIGSNSVT | 17 |
| SGSSSNIGSNAVT | 18 |
| TGSSSNIGSNSVT | 19 |

TABLE 1e

| CDRL2 | |
|---|---|
| Sequence | SEQ ID NO |
| YNSHRPS | 20 |
| ANSHRPS | 21 |
| ADSQRPS | 22 |
| YNNKRPS | 23 |
| SDSHRPS | 24 |
| ADVQRPS | 69 |

TABLE 1f

| CDRL3 | |
|---|---|
| Sequence | SEQ ID NO |
| GSWDASLNAYV | 25 |
| GSWDDSLSGYV | 26 |
| GTWDSSLNAYV | 27 |
| GTWDDSLSGYV | 28 |
| GTWDASLNAYV | 29 |
| GSWDASLNAYV | 25 |

In one embodiment, heavy chain and light chain variable regions of the antibody or antigen-binding fragment comprising the light chain and heavy chain CDR sequences may be exemplified in the following Table 2a and Table 2b, respectively.

TABLE 2a

| Heavy Chain Variable Region (VH) Sequence | SEQ ID NO |
|---|---|
| EVQLLESGGGLVQPGGSLRLSCAASGFTFSDYAMSWVRQAPGKGLEWVSSISSGS GSIYYADSVKGRFTISRDNSKNTLYLQMNSLRAEDTAVYYCAKNLIPLDYWGQGT LVTVSS | 30 |
| EVQLLESGGGLVQPGGSLRLSCAASGFTFSGYYMSWVRQAPGKGLEWVSLISPSS GSIYYADSVKGRFTISRDNSKNTLYLQMNSLRAEDTAVYYCAKGLTKFDYWGQG TLVTVSS | 31 |
| EVQLLESGGGLVQPGGSLRLSCAASGFTFSSYSMSWVRQAPGKGLEWVSGIYSDG SNTYYADSVKGRFTISRDNSKNTLYLQMNSLRAEDTAVYYCAKMLHRFDYWGQ GTLVTVSS | 32 |

TABLE 2a-continued

| Heavy Chain Variable Region (VH) Sequence | SEQ ID NO |
|---|---|
| EVQLLESGGGLVQPGGSLRLSCAASGFTFSDYAMSWVRQAPGKGLEWVSGISPGG SNTYYADSVKGRFTISRDNSKNTLYLQMNSLRAEDTAVYYCAKDAWIARLLLFD YWGQGTLVTVSS | 33 |
| EVQLLESGGGLVQPGGSLRLSCAASGFTFSSYGMSWVRQAPGKGLEWVSGIYSGG SSKYYADSVKGRFTISRDNSKNTLYLQMNSLRAEDTAVYYCAKNRLRFDYWGQG TLVTVSS | 34 |
| EVQLLESGGGLVQPGGSLRLSCAASGFTFSSYSMSWVRQAPGKGLEWVSGIYSDA SNTYYADSVKGRFTISRDNSKNTLYLQMNSLRAEDTAVYYCAKMLHRFDYWGQ GTLVTVSS | 70 |

15

TABLE 2b

| Light Chain Variable Region (VL) Sequence | SEQ ID NO |
|---|---|
| QSVLTQPPSASGTPGQRVTISCSGSSSNIGSNAVSWYQQLPGTAPKLLIYYNSHRPS GVPDRFSGSKSGTSASLAISGLRSEDEADYYCGSWDASLNAYVFGGGTKLTVLG | 35 |
| QSVLTQPPSASGTPGQRVTISCTGSSSNIGSNDVSWYQQLPGTAPKLLIYANSHRPS GVPDRFSGSKSGTSASLAISGLRSEDEADYYCGSWDDSLSGYVFGGGTKLTVLG | 36 |
| QSVLTQPPSASGTPGQRVTISCSGSSSNIGSNSVTWYQQLPGTAPKLLIYADSQRPS GVPDRFSGSKSGTSASLAISGLRSEDEADYYCGTWDSSLNAYVFGGGTKLTVLG | 37 |
| QSVLTQPPSASGTPGQRVTISCSGSSSNIGSNAVTWYQQLPGTAPKLLIYYNNKRPS GVPDRFSGSKSGTSASLAISGLRSEDEADYYCGTWDDSLSGYVFGGGTKLTVLG | 38 |
| QSVLTQPPSASGTPGQRVTISCTGSSSNIGSNSVTWYQQLPGTAPKLLIYSDSHRPS GVPDRFSGSKSGTSASLAISGLRSEDEADYYCGTWDASLNAYVFGGGTKLTVLG | 39 |
| QSVLTQPPSASGTPGQRVTISCSGSSSNIGSNSVTWYQQLPGTAPKLLIYADVQRPS GVPDRFSGSKSGTSASLAISGLRSEDEADYYCGTWDSSLNAYVFGGGTKLTVLG | 71 |

In one embodiment, CDRs of each variable region of light chain and CDRs of each variable region of heavy chain disclosed in Table 1a to Table 1f can be combined freely.

In other embodiment, the variable regions of heavy chain and light chain disclosed in Table 2a and Table 2b can be combined freely for preparation of various forms of antibodies, and for example, a single antibody such as scFV, or domain antibody can be formed.

Each of heavy chain and light chain variable regions disclosed herein may bind to targeting various heavy chain and light chain constant regions to form heavy chain and light chain of an intact antibody, respectively. In addition, each of heavy chain and light chain sequences bound to constant regions like this may be also combined to form an intact antibody structure.

Any variable region of heavy chain and light chain of the antibody may be linked to at least a part of constant regions. The constant regions may be selected according to whether antibody-dependent cell-mediated cytotoxicity, antibody-dependent cell phagocytosis and/or complement-dependent cytotoxicity, etc. is required. For example, Human isotype IgG1 and IgG3 have complement-dependent cytotoxicity, and human isotype IgG2 and IgG4 do not have the cytotoxicity. Human IgG1 and IgG3 also induce a cell-mediated effector function stronger than human IgG2 and IgG4. For example, the heavy chain variable region may bind to a constant region of IgG, such as IgG1, IgG2, IgG2a, IgG2b, IgG3 and IgG4, and the light chain variable region may bind to a kappa or lambda constant region. For the constant region, one appropriate as desired can be used, and for example, a human or mouse-derived one can be used. In one embodiment, a human heavy chain constant region IgG1 is used, and this may be represented by the sequence of SEQ ID NO: 60. In other embodiment, as the light chain constant region, a human lambda region is used, and this may be represented by SEQ ID NO: 64.

Any variable region disclosed herein may be bound to a constant region, thereby forming heavy chain and light chain sequences. In one embodiment, the heavy chain variable region disclosed herein may be bound to a human IgG1 constant region, to form a heavy chain (full-length) comprising or consisting essentially of an amino acid sequence selected from SEQ ID NOs: 40 to 44, and 72. In other embodiment, the light chain variable region disclosed herein may be bound to a human lambda constant region, to form and the light chain (full-length) comprising or consisting essentially of an amino acid sequence selected from SEQ ID NOs: 45 to 49, and 73. The light chain and heavy chain can be combined as various combinations, thereby forming an intact antibody consisting of two light chains and two heavy chains.

However, such constant region sequences to be combined with the variable regions disclosed herein are exemplary, and those skilled in the art will know that other constant regions including IgG1 heavy chain constant region, IgG3 or IgG4 heavy chain constant region, any kappa or lambda light chain constant region, constant regions modified for stability, expression, manufacturability or other targeting properties, etc. may be used.

The present invention comprises one or more amino acid sequences having substantial sequence identity with one or more amino acid sequences disclosed herein. The substantial identity means maintaining the effect disclosed herein in which the sequence variation is present. In one embodiment, it has about 90%, 95%, or 99% identity to the heavy chain variable regions disclosed in Table 2a. In other embodiment, it has about 90%, 95%, or 99% identity to the light chain variable regions disclosed in Table 2b. For example, in case of variant showing 90%, 95%, or 99% identity to the antibody or antigen-binding fragment disclosed herein, any variation is occurred in a frame of variable regions than CDRs.

Herein, a nucleic acid encoding the antibody or its part disclosed herein is disclosed. The nucleic acid includes a PCR or sequence analysis primer used for amplification, investigation, analysis or mutant induction of a polynucleotide encoding each chain of antibody, or fragment of the antibody, its mutant, derivative, or variant, a polynucleotide encoding a light chain or heavy chain variable region or only CDR, a polynucleotide enough to be used as a hybridization probe, and a polynucleotide encoding a polypeptide. The nucleic acids can be of any length. These may be for example, 5, 10, 15, 20, 25, 30, 35, 40, 45, 50, 75, 100, 125, 150, 175, 200, 250, 300, 350, 400, 450, 500, 750, 1,000, 1,500, 2000, or 2500 or more of polynucleotides in length and/or may comprise one or more of additional sequences, for example, regulatory sequences, and/or may be a bigger nucleic acid, for example, a part of vector. The nucleic acid may be a single strand or double strand, and may comprise RNA and/or DNA polynucleotide, and its artificial variant (e.g. peptide nucleic acid).

In one embodiment, the nucleic acid encoding the antibody or its fragment disclosed herein is a nucleic acid encoding a CDR disclosed herein, a variable region comprising the CDR, a full-length antibody comprising the variable region and constant region. When the amino acid sequence is determined, the nucleic acid sequence may be usefully determined, considering a known reverse transcription program and codon usage, etc. The exemplary nucleic acid sequence of the heavy chain constant region encoding human IgG1 may be represented by SEQ ID NOs: 61 to 63. The exemplary nucleic acid sequence of the light chain constant region encoding human lambda may be represented by SEQ ID NOs: 65 to 67. The exemplary nucleic acid sequence of the full-length heavy chain comprising the nucleic acid sequence of the constant regions may be selected from SEQ ID NOs: 50 to 54, and 74 (heavy chain comprising a human IgG1 constant region), and the exemplary nucleic acid sequence may be selected from SEQ ID NOs: 60 to 59 and 75 (light chain comprising a human lambda constant region).

In addition, a nucleic acid sequence encoding CDR sequences of Table 1a to Table 1f, and variable regions of Table 2a and Table 2b is comprised. Since this nucleic acid sequence is included the aforementioned nucleic acid sequence encoding the full-length antibody, it is not disclosed separately, and those skilled in the art will easily confirm the nucleic acid sequence from the nucleic acid SEQ ID NOs: 50 to 59, based on the protein sequence of CDRs and variable regions disclosed herein.

The present invention also includes one or more nucleic acid sequences having the substantial sequence identity to one or more nucleic acid sequences disclosed herein. The substantial identity means that the antibody or antigen-binding fragment encoded by the nucleic acid maintains the effect disclosed herein, even in case of causing conservative substitution or amino acid variation in which the variation of nucleic acid does not accompany amino acid substitution.

Specificity and Affinity to Antigen of Antibody

The antibody or antigen-binding fragment particularly has specificity to B7-H3 antigen and appropriate affinity to be used as an antibody therapeutic agent/diagnostic agent. In one embodiment, according to Table 5, the affinity to an aggregate is $K_D<1.0\times10^{-9}$ M; in another embodiment, it is $K_D<1.0\times10^{-10}$ M. The antibody or antigen-binding fragment having the affinity has an advantage in that it can be administered in a lower amount of administration, compared to an antibody having low affinity, for example, more than $10^{-7}$ M of affinity. This does not limit the antibody, for example, it, but since the enough efficacy can be obtained, despite of administration by simpler way such as subcutaneous injection, there is a big advantage clinically.

Variable Region of Antibody

The present invention relates to the antibody light chain variable region or antibody heavy chain variable region shown in Table 2a and Table 2b, and an antibody (and corresponding nucleic acid sequence) including an immunological functional fragment, a derivative, a mutant protein and a variant of the light chain and heavy chain variable regions. The antibody in which the variable regions of heavy chain and light chain are combined variously may be represented by "VHx/VLy", wherein "x" corresponds to the heavy chain variable region SEQ ID NO, and "y" corresponds to the light chain variable region SEQ ID NO. In one embodiment, the variable region may comprise the following combinations, but not limited thereto: VH30/VL35, VH30/VL36, VH30/VL37, VH30/VL38, VH30/VL39, VH30/VL71, VH31/VL35, VH31/VL36, VH31/VL37, VH31/VL38, VH31/VL39, VH31/VL71, VH32/VL35, VH32/VL36, VH32/VL37, VH32/VL38, VH32/VL39, VH32/VL71, VH33/VL35, VH33/VL36, VH33/VL37, VH33/VL38, VH33/VL39, VH33/VL71, VH34/VL35, VH34/VL36, VH34/VL37, VH34/VL38, VH34/VL39, VH34/VL71, VH70/VL35, VH70/VL36, VH70/VL37, VH70/VL38, VH70/VL39, or VH70/VL71.

The various combinations of variable regions as aforementioned may be used as an intact antibody and various forms of antibodies comprising scFV, etc.

CDR

The antibody disclosed herein is a polypeptide in which one or more CDRs are grafted, inserted and/or linked. In one embodiment, the antibody may have 1, 2, 3, 4, 5 or 6 CDRs. Thus, the antibody may have for example, one heavy chain CDR1 ("CDRH1"), and/or one heavy chain CDR2 ("CDRH2"), and/or one heavy chain CDR3 ("CDRH3"), and/or one light chain CDR1 ("CDRL1"), and/or one light chain CDR2 ("CDRL2"), and/or one light chain CDR3 ("CDRL3").

The position of amino acid sequences corresponding a complementary determining region (CDR) and a frame region (FR) of an antibody in a variable region may be determined by Kabat (Kabat et al., (1983) U.S. Dept. of Health and Human Services, "Sequences of Proteins of Immunological Interest"), Chothia (Chothia and Lesk, J. Mol. Biol. 196:901-917 (1987)) or a method related to OPAL library (Hye Young Yang et. al., 2009 Mol. Cells 27: 225). The CDRs determined by each definition may be a subset which is overlapped or that one comprises the other, when comparing each other. However, herein, all CDRs to be defined by each method are included in the scope of the present invention. Those skilled in the art will easily select a CDR sequence by each definition among them, when the sequence of variable region of an antibody is provided.

In one embodiment, CDRs to be comprised in the heavy chain and light chain of the antibody are disclosed in Table 1a to 1f (or heavy chain CDRH1 is represented by any one selected from SEQ ID NOs: 1 to 4, and CDRH2 is represented by any one selected from SEQ ID NOs: 5 to 9 and 68, and CDRH3 is represented by any one selected from SEQ ID NOs: 10 to 14, and CDRL1 is represented by any one selected from SEQ ID NOs: 15 to 19, and CDRL2 is represented by any one selected from SEQ ID NOs: 20 to 24 and 69, and CDRL3 is represented by any one selected from SEQ ID NOs: 25 to 29).

An embodiment also comprises one or more amino acid sequences having substantial sequence identity with amino acid sequences of one or more CDRs disclosed in Table 1a to Table 1f. The substantial identity means maintaining the effect disclosed herein in which the sequence variation is present.

The structure and properties of CDR of a naturally or non-naturally occurring antibody are as aforementioned. Simply, in a typical antibody, the CDR is comprised in a framework of heavy chain and light chain variable regions consisting of a region which is involved in antigen binding and recognition. The variable region comprises 3 heavy chain CDRs and/or 3 light chain CDRs in a framework region. The CDRs may be determined and the amino acid residues may be numbered, in heavy chain and light chain, or their variable regions, according to Kabat definition (Kabat et al., (1983) U.S. Dept. of Health and Human Services, "Sequences of Proteins of Immunological Interest"), Chothia (Chothia and Lesk, J. Mol. Biol. 196:901-917 (1987)) or a method related to OPAL library (Hye Young Yang et. al., 2009 Mol. Cells 27: 225). However, the CDR disclosed herein is used for defining a typical antibody structure of antigen-binding domain, and in addition, as disclosed herein, it can be used as comprised in other various polypeptide structures.

Those skilled in the art will understand that disclosed each CDR can be selected and combined independently each other, when an antibody comprises one or more of CDRs disclosed herein. Thus, an antibody having 1, 2, 3, 4, 5 or 6 of independently selected CDRs. In addition, those skilled in the art may know that when the CDR is selected for combination, the same kind of CDR is not repeatedly used, and for example, the antibody is commonly not prepared as comprising two CDRH2 regions.

Monoclonal Antibody

The antibody disclosed herein may comprise a monoclonal antibody binding to B7-H3. In particular, it comprises a human monoclonal antibody specifically recognizing a B7-H3 extracellular domain, and shows cross-reactivity to mouse and monkey B7-H3.

The monoclonal antibody may be prepared by using any technique known in the art. For example, in addition, a technique to prepare an antibody having different properties such as an antibody having various affinity to an antigen is also known. This technique is for example, chain shuffling performed by displaying an immunoglobulin variable domain gene repertory on a surface of filament bacteriophage called a phage display. For example, what is disclosed in examples herein is referred, or as an additional technique, what is disclosed in Marks et al. 1991, J. Mol. Bio. 222: 581-597; Marks et al., 1992, BioTechnology 10:779-783 may be referred.

In addition, the monoclonal antibody may be prepared by using any technique known in the art. For example, it may be produced by immortalizing splenocytes collected from an immunized transformed animal. The splenocytes may be immortalized by using any technique known in the art, for example, by fusing them with myeloma cells to produce hybridoma. The myeloma cells to be used for the hybridoma-production fusion process are preferably non-antibody-productive, have high fusion efficiency, and make them unable to grow in a specific selective medium that lacks certain enzymes and supports the growth of only the targeting fusion cells (hybridoma). The examples of appropriate cell lines to be used for mouse fusion include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XXO Bul, and the examples of cell lines used for rat fusion include R210.RCY3, Y3-Ag 1.2.3, IR983F and 4B210. Other cell lines useful for cell fusion may be U-266, GM1500-GRG2, LICR-LON-HMy2 and UC729-6. In some cases, hybridoma cell lines are produced by collecting splenocytes from an animal (for example, transformed animal having a human immunoglobulin sequence, animal immunized by B7-H3 immunogen); fusing collected splenocytes to myeloma cells to produce hybridoma cells; establishing hybridoma cell lines from hybridoma cells, and identifying hybridoma cell lines producing an antibody binding to B7-H3. The monoclonal antibody secreted by hybridoma cell lines may be purified by using a technique known in the art.

Chimeric Antibody

The antibody can be also modified by various methods for various purposes. A chimeric antibody is an antibody forming an immunologically functional light chain, heavy chain or fragment thereof, by that polypeptide fragments derived from different antibodies are linked by covalent bonds. Commonly, a part of light chain and/or heavy chain of the chimeric antibody is a sequence belongs to a certain species or certain class or subtype, and the rest sequence belongs to other species or other class or subtype. For a method of preparation of a chimeric antibody, for example, U.S. Pat. No. 4,816,567; and Morrison et al., 1985, Proc. Natl. Acad. Sci. USA 81:6851-6855 may be referred. For CDR grafting, for example, U.S. Pat. Nos. 6,180,370, 5,693,762, 5,693,761, 5,585,089 and 5,530,101 may be referred.

Commonly, a purpose for preparing a chimeric antibody is to maximize the number of amino acids found in an organism in which an antibody is used. One example is a "CDR-grafted" antibody, wherein the antibody comprises one or more of CDRs derived from a certain species, or certain class or subtype, and the rest part is derived from other species, or other class or subtype antibody. For example, to use it to human, a naturally appearing variable region or CDR of human antibody by that a variable region or selected CDR of rodent antibody is grafted in the human antibody may be replaced or vice versa.

In addition, in one embodiment, for a constant region derived from species other than human, a hybrid antibody combined with a variable region derived from human may be used.

Complete Human Antibody

A complete human antibody is also disclosed. A complete human antibody specific to certain antigen can be prepared without exposing human to an antigen.

The complete human antibody may be also derived from a phage-display library (Hoogenboom et al., 1991, *J. Mol. Biol.* 227:381; and Marks et al., 1991, *J. Mol. Biol.* 222:581). The phage display technique is a method mimicking a kind of immune selection which displays an antibody repertoire on a surface of filamentous bacteriophage and therefrom, sorts a phage binding to a targeting antigen. This one technique may refer to examples herein or PCT laid-open publication No. WO 99/10494. In one embodiment, the complete human B7-H3 antibody of the present invention is sorted through the phage display method. This technique may refer to for example, examples herein or PCT laid-open publication No. WO 2005/012359.

Other method producing a complete human antibody is "humanizing" a mouse humoral immune system. An endogenous Ig gene may introduce human immunoglobulin (Ig) genetic loci to a non-activated mouse, thereby producing a complete human monoclonal antibody (mAb) in the mouse. If using the complete human antibody, an immunogenic reaction and allergic reaction which may be caused by administering a mouse or mouse-derived mAb into human may be minimized. This complete human antibody may be produced by immunizing a transformed animal (commonly, mouse) which can produce a human antibody by lacking production of an endogenous immunoglobulin. An antigen for this purpose typically has 6 or more of sequential amino acids, and randomly, is conjugated to a carrier, for example, hapten. For example, the followings may be referred: Jakobovits et al., 1993, *Proc. Natl. Acad. Sci. USA* 90:2551-2555; Jakobovits et al., 1993, *Nature* 362:255-258; and Bruggermann et al., 1993, *Year in Immunol.* 7:33. As one example, in this method, the transformed animal is produced by incapacitating endogenous mouse immunoglobulin gene loci encoding mouse heavy and light chain immunoglobulin chains and inserting a loci fragment comprising a human genome DNA encoding human heavy chain and light chain proteins. By cross-mating a partially modified mouse partially comprising human immunoglobulin genetic loci, a mouse in which the complete human immunoglobulin gene is introduced is produced. When an immunogen is administered to the animal, an antibody which is immunospecific to the immunogen, but comprises a variable region has a human amino acid sequence not murine. This method refers to for example, WO96/33735 and WO94/02602. A method related to a transformed mouse to prepare a human antibody may refer to U.S. Pat. Nos. 5,545,807; 6,713,610; 6,673,986; 6,162,963; 5,545,807; 6,300,129; 6,255,458; 5,877,397; 5,874,299 and 5,545,806; WO91/10741, No. WO90/04036, and EP No. 546073B1.

Then, using a hybridoma technique, the antigen-specific human mAb having a targeting specificity can be produced and selected from a transgenic mouse, for example, the aforementioned one. This antibody can be cloned and expressed by using appropriate vector and host cell, or the antibody can be collected from a cultured hybridoma cell.

Various Forms of Antibodies

The antibody disclosed herein is also a variant of the antibody disclosed herein. For example, a part of antigen comprises conservative amino acid substitution in one or more of residues of the heavy chain or light chain, variable region or CDR sequence disclosed above. The conservative amino acid substitution means substitution which does not substantially affect the activity of a polypeptide or antigenicity. In one embodiment, the conservative amino acid substitution refers to substitution to other residues which belongs to the same classification among the following amino acid classification. Naturally-occurring amino acids may be classified on the basis of common properties of side chain properties as follows: 1) hydrophobic: norleucine, Met, Ala, Val, Leu, Ile; 2) neutral, hydrophilic: Cys, Ser, Thr, Asn, Gln; 3) acidic: Asp, Glu; 4) basic: His, Lys, Arg; 5) residue affecting a chain direction: Gly, Pro; and 6) aromatic: Trp, Tyr, Phe.

The conservative amino acid substitution refers to substitution to other residue belonging to the same classification in the classification. The conservative amino acid substitution may also comprise a non-naturally-occurring amino acid residue such as a peptide mimetic, and this residue is typically introduced by chemical synthesis, not a cell.

Unlimited exemplary examples of conservative amino acid substitution are shown in Table 3.

TABLE 3

| Conservative amino acid substitution | |
|---|---|
| original residue | Exemplary subsititution |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Non-conservative substitution includes substitution to a residue which belongs to other classification among the above classification. This substitution may be introduced in a region of an antibody which is homologous to a human antibody or a non-homologous region.

For introducing this substitution, in one embodiment, an index showing hydrophobicity or hydrophilicity of an amino acid (hydropathic index) may be considered. The index profile of a protein (hydropathic profile) is calculated by designating the index for each amino acid, and then repeatedly averaging these values. The indexes of each amino acid is designated on the basis of hydrophobicity and charge property as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

For giving an interactional biological function to a protein, the importance of index profile is known in the art (Kyte et al., 1982, *J. Mol. Biol.* 157:105-131). It is known that a specific amino acid may be substituted with other amino acid having a similar numerical value index or score, and the similar biological activity may be maintained. In one embodiment, for performing a change based on the index, the substitution in which the index is in ±2, in ±1, or in ±0.5 is included.

In addition, substitution between similar amino acids, in particular, when a protein produced by substitution is a protein having activity immunologically as described herein, may be performed on the basis of hydrophilicity. In one embodiment, the maximum local average hydrophilicity value of a protein, which is determined by hydrophilicity of a close amino acid, is related to biological properties of a protein such as immunogenicity and antigen-binding property.

The hydrophilicity values of amino acid residues are as follows: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In case of substitution based on similar hydrophilicity values, in one embodiment, substitution of amino acids of which hydrophilicity values are in ±2, in ±1, or in ±0.5 is included. In addition, an epitope may be identified from the primary amino acid sequence on the basis of hydrophilicity. In addition, these regions are called "epitope core regions".

Those skilled in the art will determine an appropriate variant of the polypeptide disclosed herein using a known technique. Those skilled in the art will find a site which can change a protein without destroying the activity, by targeting a region that is not considered important for activity in the polypeptide. Those skilled in the art will also identify a residue or part to be conserved between similar polypeptides. In addition, in other embodiment, for a part considered as important for biological activity or structure, the conservative amino acid substitution may be performed, without destroying biological activity, or negatively affecting a polypeptide structure.

Moreover, those skilled in the art may perform a structural-functional analysis to identify a residue important for activity or structure in a similar polypeptide. Through this analysis, an important amino acid residue in a targeting protein may be predicted by finding a residue corresponding to an important amino acid residue for activity or structure of a protein similar to it, in one protein. Those skilled in the art may substitute the important amino acid residue predicted on this wise to an amino acid chemically similar to it.

Those skilled in the art, in addition, may predict an amino acid residue related to a three-dimensional structure of an antibody based on the three-dimensional structure of a similar polypeptide and amino acid sequence analysis related to it. Those skilled in the art do not introduce a rapid change, since the amino acid residue predicted as present on a surface of a protein may be involved in an important interaction with another molecule. Moreover, those skilled in the art may produce test variants comprising substitution of a single amino acid in each targeting amino acid residue. These variants, then, are screened by using the binding capacity to an antigen, thereby collecting information as to which amino acid substitution matches the purpose. Using this information, those skilled in the art may easily determine a position to be substituted or a position to be avoided.

In addition, a position to be substituted may be determined on the basis of secondary structure of a protein. For example, one method of predicting the secondary structure is based on homology modeling. For example, 2 polypeptides or proteins having more than 30% of sequence identity or more than 40% of similarity may have similar structural phases (Holm et al., 1999, *Nucl. Acid. Res.* 27:244-247). For additional methods of predicting the secondary structure, "threading" (Jones, 1977, *Curr. Opin. Struct. Biol.* 7:377-387; Sippl et al., 1996, *Structure* 4:15-19), "profile analysis" (Bowie et al., 1991, *Science* 253:164-170; Gribskov et al., 1990, *Meth. Enzym.* 183:146-159; Gribskov et al., 1987, *Proc. Nat. Acad. Sci.* 84:4355-4358), and "evolutionary linkage" (Holm, 1999, ibid; and Brenner, 1997, ibid) are included.

In some embodiments, amino acid substitution performs (1) reducing sensitivity to protein decomposition, (2) reducing sensitivity to oxidation, (3) modifying binding affinity for forming a protein complex, (4) modifying antigen binding affinity and/or (5) modifying so as to provide a protein with other physicochemical or functional properties. For example, substitution of single or multiple amino acids including conservative substitution may perform substitution in not a domain which is involved in an intermolecular contact, but other parts. In this embodiment, the conservative amino acid substitution that does not substantially change structural properties of a parent sequence, for example, substitution to one or more of amino acids which does not change the secondary structure of the antibody, may be used. Examples of secondary and tertiary structures of polypeptides known in the art may refer to Proteins, Structures and Molecular Principles (Creighton, Ed.), 1984, W. H. New York: Freeman and Company; Introduction to Protein Structure (Branden and Tooze, eds.), 1991, New York: Garland Publishing; and Thornton et al., 1991, *Nature* 354:105).

In additional preferable antibody variants, a variant in which one or more of cysteine residues are deleted, or the cysteine residues are substituted to other amino acids such as serine, in a parent sequence is included. The cysteine variant is, in particular, a structure in which an antibody has biological activity, and it is useful when needed to be folded again. The cysteine variant may have small number of cysteine residues compared to a parent antibody, and commonly, may be comprised in an even number in order to minimize interaction due to cysteines without a pair.

The heavy chain and light chain, variable region domain and CDR disclosed herein may be used for preparing a polypeptide comprising an antigen-binding region which can specifically bind to B7-H3. For example, one or more of CDRs disclosed in Table 4 may be non-covalently or covalently bound to a molecule like a polypeptide, and thereby they may be used as an immunogenic adhesion molecule. This immunogenic adhesion molecule may be that a CDR is integrated in a big polymer, or that a CDR is linked to another polypeptide. This immunogenic adhesion molecule allows specific binding to an antigen targeting a polypeptide linked thereto or other material, for example, B7-H3 or an epitope.

A peptide mimetic based on the variable region and CDR disclosed herein is also provided. This mimetic may be a peptide, non-peptide or combination of peptide and non-peptide, and the followings may be referred: Fauchere, 1986, *Adv. Drug Res.* 15:29; Veber and Freidinger, 1985, TINS p. 392; and Evans et al., 1987, *J. Med. Chem.* 30:1229. A peptide mimetic structurally similar to one useful polypeptide has a similar effect to the original polypeptide. This compound may be developed by using a computerized molecular modeling. Commonly, the peptide mimetic is structurally similar to an antibody showing specifically binding capacity to B7-H3 herein, but one or more of peptide bonds may be replaced with bonds selected from —$CH_2NH$—, —$CH_2S$—, —$CH_2$—$CH_2$—, —CH—CH— (cis and trans), —$COCH_2$—, —$CH(OH)CH_2$— and $CH_2SO$—, by a method widely known in the art. For production of a more stable protein, one or more of residues of a conservative sequence may be substituted to the same type of D-amino acid (for example, D-lysine instead of L-lysine). In addition, a molecule which can cyclize a peptide may introduce a crosslink forming cysteine residue on the inside, thereby producing a peptide structurally imposing restrictions to a conservative sequence (Rizo and Gierasch, 1992, *Ann. Rev. Biochem.* 61:387).

The present invention also provides a derivative of the antibody disclosed herein. The derivatized antibody may comprise any molecule or material providing targeting properties, for example, an increased half-life in certain uses to the antibody or its fragment. The derivatized antibody may comprise a detectable (or labeling) residue (e.g.: molecule binding to a radioactive, colorimetric, antigenic, or enzyme molecule, detectable bead (e.g.: magnetic or electron-dense (e.g.: gold) bead), or other molecules (e.g.: biotin or streptavidin)), a therapeutic or diagnostic residue (e.g.: radioactive, cytotoxic, or pharmaceutically active residue), or a molecule increasing suitability of the antibody for special uses (for example, administration to a subject, for example, a human subject, or other in vivo or in vitro uses). For examples of a molecule to be used for derivatizing an antibody, albumin (e.g.: human serum albumin) and polyethylene glycol (PEG) are included. The albumin-linked and pegylated derivatives of the antibody may be prepared by using techniques widely known in the art. In one embodiment, a pegylated single chain polypeptide is comprised. In another embodiment, the antibody may be conjugated or linked to transthyretin (TTR) or TTR variant. The TTR or TTR variant may be chemically modified by chemical materials selected from the group consisting of for example, dextran, poly(n-vinyl pyrrolidone), polyethylene glycol, propropylene glycol homopolymer, polypropylene oxide/ethylene oxide copolymer, polyoxyethylated polyol and polyvinyl alcohol.

Other derivatives include a covalent or agglomerating conjugate of an B7-H3 binding protein and other protein or polypeptide, which can be prepared for example, by expression of a recombinant fusion protein comprising a heterogeneous polypeptide fused in N-terminal or C-terminal of B7-H3 protein. For example, the conjugated peptide may be a heterogeneous signal (or reader) polypeptide, for example, a yeast alpha-factor reader, or a peptide, for example, an epitope tag. The B7-H3 antibody-comprising fusion protein may comprise a peptide added to make purification or identification of B7-H3 binding protein (e.g.: poly-His) easy. The B7-H3 binding protein may be also linked to FLAG peptide as described in Hopp et al., 1988, *Bio/Technology* 6:1204; and U.S. Pat. No. 5,011,912. The FLAG peptide has excellent antigenicity, and therefore acts as an epitope to be reversibly bound by a specific monoclonal antibody (mAb), thereby allowing rapid confirmation and easy purification of a recombinant protein.

In one embodiment, it relates to an oligomer comprising multiple B7-H3-binding polypeptides to be bound through covalent or non-covalent interaction between peptide residues fused to the B7-H3 binding protein. This peptide to be bound may be a peptide such as a peptide linker (spacer) or a leucine zipper having a property of facilitating oligomerization. In one embodiment, the oligomer comprises 2 or 4 of B7-H3 binding proteins. The B7-H3 binding protein residue of the oligomer may be aforementioned any form, for example, a variant or fragment. Preferably, the oligomer comprises an B7-H3 binding protein having B7-H3 binding activity.

In one embodiment, the oligomer is prepared by using a polypeptide derived form an immunoglobulin. The preparation of a fusion protein comprising heterogeneous polypeptides fused to various sites (including an Fc domain) of an antibody-derived polypeptide may refer to for example, Ashkenazi et al., 1991, *Proc. Natl. Acad. Sci. USA* 88:10535; Byrn et al., 1990, *Nature* 344:677; and Hollenbaugh et al., 1992 "Construction of Immunoglobulin Fusion Proteins", in *Current Protocols in Immunology, Suppl.* 4, pages 10.19.1-10.19.11.

Other embodiment relates to a dimer comprising 2 fusion proteins in which the B7-H3 binding protein is fused to a Fc region of an antibody. The dimer may be prepared by inserting a gene fusion encoding a fusion protein into an appropriate expression vector, expressing the gene fusion in a host cell transformed by a recombinant expression vector, and allowing the expressed fusion protein to combine similarly to an antibody molecule, and in this regard, a disulfide bond between chains is formed between Fc residues to collect the dimer.

The term "Fc polypeptide" used herein is a polypeptide derived from an Fc region of an antibody, and includes a wildtype or mutant form. A cut form of polypeptide comprising a hinge region which facilitates dimerization is also included. The fusion protein comprising an Fc residue or oligomer formed therefrom may have an advantage of being separated easily with an affinity chromatography using a protein A or protein G column.

For examples of appropriate Fc polypeptides, there are those described in U.S. Pat. Nos. 5,426,048 and 5,262,522, 5,457,035 and Baum et al., 1994, *EMBO J.* 13:3992-4001. In the amino acid sequence of this mutant protein, the wildtype amino acid $19^{th}$ residue is substituted from Leu to Ala, and the amino acid $20^{th}$ residue is substituted from Leu to Glu, and the amino acid $22^{th}$ residue is substituted from Gly to Ala. In the mutant protein, the affinity to an Fc receptor is reduced.

In other embodiment, the variable region of heavy chain and/or light chain of B7-H3 binding protein disclosed herein may be substituted and enter a variable region of heavy chain and/or light chain of another antibody.

Label and Effector Groups

In some embodiments, the antibody or antigen-binding fragment may comprise one or more of labels. "Label" means any detectable material. For examples of appropriate label groups, a radioactive isotope or radioactive nuclide (e.g.: $^{3}H$, $^{14}C$, $^{15}N$, $^{35}S$, $^{90}Y$, $^{99}Tc$, $^{111}In$, $^{125}I$, $^{131}I$), a fluorescent group (e.g.: FITC, rhodamine, lanthanoid fluorescent substance), an enzyme group (e.g.: horse radish peroxidase, β-galactosidase, luciferase, alkaline phosphatase), a chemiluminescent group, a biotinyl group, or certain polypeptide epitope recognized by a secondary reporter (for example, leucine zipper pair sequence, secondary antibody binding site, metal binding domain, epitope tag) is included, but not limited thereto. In some embodiments, the labeling group is coupled to an antibody through various length of space arms to reduce potential steric hindrance. Various methods to label a protein are known in the art, and those skilled in the art will select an appropriate label and a proper method for a specific purpose.

The term "effector group" is a material to be coupled or conjugated to an antibody or synthetic material. In one embodiment, the synthetic material means any material functioning for treatment. In one embodiment, examples of appropriate materials for treatment include radioactive materials for treatment such as a radioactive isotope or radioactive nuclide (e.g.: $^{3}H$, $^{14}C$, $^{15}N$, $^{35}S$, $^{90}Y$ $^{99}Tc$, $^{111}In$, $^{125}I$, $^{131}I$). As other proper examples, a cytotoxic agent or anti-cancer agent is included, and for example, paclitaxel, docetaxel, auristatin, geldanamycin, auristatin, geldanamycin, maytansine, anthracycline derivative, Calicheamicin, Duocarmycin, Camptothecin, amanitin, pyrrolobenzodiazepines (PBD) dimer, 1-(Chloromethyl)-2,3-dihydro-1H-benzo[e]indole (CBI) dimer and CBI-PBD heterogeneous dimer are included, but not limited thereto. In some embodiments, the effector group is coupled to an antibody through various length of spacer arms to reduce potential steric hindrance.

Commonly, labels may be classified according to detection methods: a) radioactive or isotope label; b) magnetic label (e.g.: magnetic particle); c) oxidation-reduction active residue; d) optical dye; enzyme group (for example, horse radish peroxidase, β-galactosidase, luciferase, alkaline phosphatase); e) biotinyl group; and f) certain polypeptide epitope recognized by a secondary reporter (e.g.: leucine zipper pair sequence, binding site for a secondary antibody, metal binding domain, epitope tag, etc.). In some embodiments, the labeling group is coupled to an antibody through various length of spacer arms to reduce potential steric hindrance. Various methods for labeling a protein are known in the art.

In one embodiment, the label comprises an optical dye comprising a chromophore, a phosphor and a fluorescent substance, but not limited thereto. The fluorescent substance may be a small-molecular fluorescent material or protein fluorescent material.

"Fluorescent label" means any molecule to be detected by fluorescent properties which a material has. For examples of the fluorescent label, fluorescein, rhodamine, tetramethylrhodamine, eosin, erythrosine, coumarin, methyl-coumarin, pyrene, malachite green, stilbene, lucifer yellow, cascade blue J, texas red, IAEDANS, EDANS, BODIPY FL, LC red 640, Cy 5, Cy 5.5, LC red 705, oregon green, alexa-fluor dye (alexa-fluor 350, alexa-fluor 430, alexa-fluor 488, alexa-fluor 546, alexa-fluor 568, alexa-fluor 594, alexa-fluor 633, alexa-fluor 647, alexa-fluor 660, alexa-fluor 680), cascade blue, cascade yellow and R-phycoerythrin (PE), FITC,), Cy5, Cy5.5, and Cy7 etc. are included, but not limited thereto. Various optical dyes may refer to Molecular Probes Handbook, Richard P. Haugland.

The protein fluorescent label substances include green fluorescent proteins including *Renilla, Ptilosarcus* or *Aequorea* species of GFP (Chalfie et al., 1994, *Science* 263:802-805), EGFP (Clontech Labs., Inc., Genbank Accession Number U55762), blue fluorescent proteins (BFP, Quantum Biotechnologies, Inc., Quebec, Canada; Stauber, 1998 Biotechniques 24:462-471; Heim et al., 1996, *Curr. Biol.* 6:178-182), enhanced yellow fluorescent proteins (EYFP, Clontech Labs., Inc.), luciferase (Ichiki et al., 1993, *J. Immunol.* 150:5408-5417), R galactosidase (Nolan et al., 1988, *Proc. Natl. Acad. Sci. U.S.A.* 85:2603-2607), but not limited thereto.

Nucleic Acid

In one aspect, the present invention relates to a nucleic acid confused to the nucleic acid disclosed herein under a specific hybridization condition. The hybridization method of the nucleic acid is widely known in the art. For example, Current Protocols in Molecular Biology, John Wiley & Sons, N.Y. (1989), 6.3.1-6.3.6 may be referred. Herein, a strict hybridization condition uses pre-washing solution comprising 5× sodium chloride/sodium citrate (SSC), 0.5% SDS, 1.0 mM EDTA (pH 8.0); a hybridization buffer of about 50% formamide, 6×SSC, and a hybridization temperature of 55° C. (or other similar hybridization solution, for example, a solution comprising about 50% formamide, a hybridization temperature of 42° C.), and a washing condition of 60° C. in 0.5×SSC, 0.1% SDS. The strict hybridization condition is hybridization by 6×SSC at 45° C., and then 0.1×SSC at 68° C., and one or more of washing in 0.2% SDS. Further, those skilled in the art will select proper hybridization conditions required so that a nucleic acid comprising at least 65%, 70%, 75%, 80%, 85%, 90%, 95%, 98% or 99% identical nucleotide sequences between sequences typically maintains a state hybridized each other.

Basic parameters affecting selection of hybridization conditions and appropriate conditions may refer to for example, Sambrook, Fritsch, and Maniatis, (2001, Molecular Cloning: A Laboratory Manual, Cold Spring Harbor Laboratory Press, Cold Spring Harbor, N.Y., above; and Current Protocols in Molecular Biology, 1995, Ausubel et al., eds., John Wiley & Sons, Inc., section 2.10 and 6.3-6.4. These conditions may be easily determined by those skilled in the art, based on for example, the length and/or base composition (configuration of A, G, C and T (U)) of the nucleic acid, etc.

The nucleic acid disclosed herein also includes a mutant variant. A change in an amino acid sequence of a polypeptide (antibody or antibody derivative) which the nucleic acid encodes may be induced by mutation in the nucleic acid. The mutant may be introduced by using any technique known in the art. For example, a site-directed mutagenesis method, a random mutagenesis method may be used. The nucleic acid mutant prepared likewise is sorted for a polypeptide having targeting properties.

Without significantly changing biological activity of a polypeptide encoded by the nucleic acid, the mutant may be introduced in the nucleic acid. For example, nucleotide substitution which causes amino acid substitution in a non-essential amino acid residue may be performed. Alternatively, one or more mutants which selectively change biological activity of a polypeptide encoded by the nucleic acid may be introduced in the nucleic acid. For example, the mutant may change biological activity quantitatively or qualitatively. The examples of quantitative changes include increase, decrease or removal of activity. The examples of qualitative changes include a change of specificity to an antigen of an antibody.

In addition, without changing an amino acid sequence of a polypeptide encoded by the nucleic acid, for example, variation for codon optimization for intracellular expression may be introduced in the nucleic acid. In this case, due to degeneracy of codon, numerous nucleic acids encoding the same polypeptide may be prepared.

The nucleic acid encoding any antibody or its fragment disclosed herein may be mutated so that the amino acid sequence is modified, by using a molecular biology technique widely known in the art.

In other aspect, in addition, the present invention relates to a nucleic acid molecule proper to be used as a primer or hybridization probe for detection of the nucleic acid sequence disclosed herein. This nucleic acid may comprise a part of full-length nucleic acid sequence, for example, a fragment of a nucleic acid encoding a full-length polypeptide, or fragment nucleic acid encoding an active part (B7-H3 binding part) of a polypeptide, to be used as a probe or a primer.

The primer and probe prepared based on the nucleic acid sequence may be used for detecting a transcriptome encoding the nucleic acid disclosed herein or similar nucleic acid, or polypeptide. In one embodiment, this probe may be used for identifying a cell expressing the polypeptide. The primer or probe may be labeled by a label material such as a radioactive isotope, fluorescent compound, enzyme or enzyme cofactor.

In other aspect, in addition, the present invention provides a vector comprising a nucleic acid encoding the polypeptide or its part (for example, fragment comprising one or more of CDRs or one or more of variable region domains). The examples of the vector include a plasmid, virus vector, non-episome mammal vector and (recombinant) expression vector, vector used for a CAR-T cell or CAR-NK cell therapeutic agent etc., but not limited thereto. The recombinant expression vector may comprise a suitable form of nucleic acid for expression of nucleic acid in a host cell. The recombinant expression vector comprises one or more of regulatory sequences based on a host cell to be used for expression, and these regulatory sequences are operably connected to a nucleic acid sequence to be expressed. In the regulatory sequence, for example, SV40 initial gene enhancer, promoter such as Rous sarcoma virus promoter and cytomegalovirus promoter, which can control expression of a nucleotide sequence in various kinds of host cells; or for example, tissue-specific regulatory sequence, which controls expression of a nucleotide sequence only in a specific host cell (Voss et al., 1986, Trends Biochem. Sci. 11:287, Maniatis et al., 1987, Science 236:1237), and metallothionein promoter working in a mammal cell, and tet-reactive and/or streptomycin reactive promoter working in both prokaryote and eukaryote systems, which instructs inductive expression of a nucleotide sequence by responding to special treatment or conditions, are included. Those skilled in the art will select an appropriate vector and a regulatory sequence, considering factors such as kinds of a host cell to be transformed, expression degree of a targeting protein. The selected expression vector may be delivered in a host cell and may be used for production of a protein encoded by the nucleic acid disclosed herein.

In other aspect, the present invention provides a host cell in which a recombinant vector is introduced. The host cell may be any prokaryote (for example, *E. coli*) or eukaryote (for example, yeast, insect, or mammal cell). The vector DNA may be introduced in a prokaryotic or eukaryotic cell through a known transformation or transfection technique. It is known that in case of stable transfection in a mammal cell, depending on kinds of expression vector used and transformation techniques, only small number of cells can integrate DNA delivered by transfection in its genome. Thus, to identify and select a transfected cell, commonly a gene encoding a selectable marker such as an antibiotic resistant marker is introduced into a host cell together with a targeting gene. For preferable selectable markers, drugs, for example, those providing resistance to for example, G418, hygromycin and methotrexate are included. The sorting of a cell in which a targeting nucleic acid is stably introduced may be achieved by selecting a survived cell only through drug treatment.

Treatment Method, Pharmaceutical Formulation

A treatment method using an antibody is also provided. In one embodiment, the antibody is provided to a patient. The antibody, in one embodiment, binds to human B7-H3 expressed on a cancer cell surface, cancer angiogenic blood vessel or antigen presenting cell and thereby inhibits the immune checkpoint of the T cell, thereby activating the T cell. The antibody binds to human B7-H3 expressed on a cancer cell surface or cancer angiogenic blood vessel, thereby inhibiting growth of a cancer cell. In one embodiment, the antibody is expressed on a surface of a cytotherapeutic agent such as CAR-T or CAR-NK, etc., and the antibody binds to human B7-H3, thereby specifically delivering the cytotherapeutic agent to the cancer cell, to induce the death of the cancer cell. In one embodiment, the antibody may be used in a combination with an anti-cancer immunoantibody, thereby inhibiting cancer through activation of the T cell.

A pharmaceutical composition comprising a therapeutically effective dose of the antibody and a pharmaceutically acceptable diluent, carrier, solubilizer, emulsifier, preservative and/or supplement is also provided. In addition, for example, a method for treating a cancer patient by administering such a pharmaceutical composition is included. Herein, the subject or patient includes a human patient.

An acceptable formulation material is non-toxic to a recipient, in used capacity and concentration. In a specific embodiment, a pharmaceutical composition comprising a therapeutically effective dose of human B7-H3 antibody is provided.

Hereinafter, desirable examples are presented to facilitate understanding of the present invention. However, the following examples are provided for a better understanding of the present invention, and the scope of the present invention is not limited by the following examples.

EXAMPLES

Example 1: Preparation of Antibody

Example 1-1: Preparation of Antigen

An antigen used for phage display performance for preparation of anti-B7-H3 antibody was purchased and used. In case of human B7-H3, the $1^{st}$ to $461^{th}$ of the amino acid sequence of NP_001019907.1 are comprised and a recombinant B7-H3 protein in which a histidine-tag (His tag) is linked to the C terminal (2318-B3/CF, R&D Systems) was used.

An antigen used for ELISA analysis, SPR analysis or T cell activity analysis of the following examples was purchased and used as follows. In case of human B7-H3, the $1^{st}$ to $461^{th}$ of the amino acid sequence of NP_001019907.1 are comprised and a recombinant B7-H3 protein in which a histidine-tag (His tag) is linked to the C terminal and a protein in which Fc region of human IgG1 is linked to the C terminal (Sino Biological, 11188-H02H) were used.

Example 1-2: Antibody Sorting Preparation Through Phage Library Screening

Preparation of Library Phage

After culturing $2\times10^{10}$ *E. coli* having a human-derived scFv (single-chain variable fragment) library (Mol. Cells OT, 225-235, Feb. 28, 2009) gene having the binding variety to various antigens in a medium comprising 2×YT (Amresco, J902-500G), ampicillin 100 μg/ml, and 2% glucose (sigma, G7021) at 37° C. for 2 hours to 3 hours so that OD600 value is 0.5 to 0.7. After infecting a helper phage by the cultured *E. coli*, it was cultured in a 2×YT [2×YT, ampicilin 100 μg/ml, 1 mM IPTG (Duchefa, I1401)] medium at 30° C. for 16 hours and thereby phage packaging was induced. Then, after centrifuging the cultured cells under the condition of 4° C., 4500 rpm for 20 minutes, 4% PEG 8000 (sigma, P2139) and 3% NaCl (Samchun, S2097) were added to a supernatant and melted well, and then it was reacted on ice for 1 hour. After centrifuging under the condition of 4° C., 8000 rpm again, PBS (Phosphate buffered saline, Gibco 10010-023) was added to a pellet and it was suspended. After the suspension was centrifuged under the condition of 4° C., 1200 rpm for 10 minutes, the supernatant was put into a new tube and it was stored at 4° C. before use.

Panning Through Phage Display

To sort antibodies binding to a human B7-H3 protein, using the recombinant B7-H3 protein, with which the histidine-tag (His tag) is linked, of Example 1-1, panning was progressed 3 times in total as follows.

Specifically, a protein was absorbed on a surface of test tube under conditions of 37° C., 200 rpm for 1 hr, by adding 2 μg/ml concentration of recombinant human B7-H3 protein of 1 ml into an immunotube (maxisorp 444202). Then, a supernatant was removed and a solution comprising 3% skim milk was added to the test tube and it was reacted at a room temperature for 1 hr. Though this, skim milk was adsorbed on the surface of the immunotube to which the recombinant human B7-H3 protein was not adsorbed, thereby blocking non-specific binding. After removing the supernatant, $10^{12}$ CFU of phage library prepared in Example 1-2 was mixed in the solution comprising 3% skim milk and put into the immunotest, and it was reacted under the conditions of 37° C., 150 rpm for 1 hr, so that the phages specific to human B7-H3 protein bound to an antigen.

Then, non-specifically bound phages were washed with PBS-T (Phosphate buffered saline-0.05% Tween 20) solution and removed, and the remained antigen-specific phage antibodies were collected by adding 1 ml of 100 mM triethylamine solution. After neutralizing the collected phages with 1M Tris buffer solution (pH 7.4) as the pH of triethylamine solution was low, it was infected to ER2537 *E. coli* grown as 0.8-1 at OD600 under the conditions of 37° C., 120 rpm for 1 hour and 30 minutes. The culture solution was centrifuged under the conditions of 4° C., 4500 rpm for 15 min and the supernatant was removed, and sunk cells were cultured at 37° C. for 16 hr or more by smearing infected *E. coli* on a 2×YT agar medium comprising ampicillin. Next day, all the cultured *E. coli* was scraped out and suspended in 5 ml of 2×YT ampicillin culture solution, and 505 glycerol was added, and a part was stored at −80° C. and the other was used for preparing a phage for the next experiment. After inoculating 20 μl of cultured *E. coli* in a 2×TB comprising ampicillin and growing it, a helper phage was infected and Examples 2-1 and 2-2 were repeated twice more, thereby amplifying and concentrating a human B7-H3 protein-specific phage pool.

Single Clone Screening

To sort monoclonal antibodies specifically binding to human B7-H3 protein from the phage pool obtained through the panning, the experiment as follows was performed.

To isolate monoclones from the concentrated pool, after smearing the phage pool on a LB-ampicillin agar medium and culturing, a single colony was secured. Then, after inoculating monoclones on a 96-deep well plate in which 200 μl of super broth (SB) medium was put per well and cultivating overnight, a part was transferred into other plate to make cell stock. 1 mM IPTG was put into the remained cell culture solution and it was cultured at 30° C. for 16 hrs, to induce production of scFv. After the cultured culture solution was centrifuged under the conditions of 4° C., 6000 rpm, the supernatant was discarded and only cells were obtained, and then cells were lysated using TES solution and then centrifuged again, thereby obtaining only the supernatant to use.

Then, clones expressing a soluble monoclonal scFv which binds to B7-H3-His antigen (2318-B3/CF, R&D Systems) were selected by using the ELISA method as follows (Steinberger. Rader and Barbas III. 2000. Phage display vectors. In: Phage Display Laboratory Manual. 1sted. ColdSpringHarborLaboratoryPress. NY. USA. pp. 11.9-11.12). Specifically, the recombinant human B7-H3-his protein prepared in Example 1 of 100 ng per well was put on a 96-well plate (Nunc-Immuno Plates, NUNC, Rochester, NY, USA) and it was adsorbed at 4° C. overnight. Next day, after washing the protein with PBST (Phosphate buffered saline-0.05% Tween 20), to prevent non-specific binding, PBS buffer solution comprising 3% BSA of 200 μL per well was put and it was reacted at 37° C. for 2 hours. Then, after washing it with PBST again, the supernatant comprising phages centrifuged and prepared in advance of 100 μl per well was put and it was reacted at 37° C. for about 1 hr. Then, after washing it with PBST, to detect phages bound to human B7-H3, the anti-HA HRP (Horseradish peroxidase)-binding antibody (Roche, 12 013 819 001) was diluted in PBS comprising 1% BSA by 1:5000, and 100 μl per well was put and it was reacted at 37° C. for about 1 hr. After washing it with PBST again, TMB (Tetramethylbenzidine, Thermo, 34028) 100 μl was put to develop color. After reacting at RT for 5-10 min, 50 ml of 1N $H_2SO_4$ was put to finish the reaction. The absorbance at 450 nm was measured to sort clones of which value was 1.0 or more.

Therefrom, 7 antibody clones binding to the recombinant human B7-H3 protein (B5, C41, D8G, F6V, 10F11, D8G M1 and D8G M3) were sorted, and the amino acid sequences and CDR sequences of heavy chain variable and light chain variable regions of each antibody were as the following tables. IDC-30 DNA

TABLE 4

| | CDR Sequences of Heavy Chain Variable (VH) | | | | | | |
|---|---|---|---|---|---|---|---|
| | CDRH1 | | CDRH2 | | CDRH3 | | VH |
| Clone | Sequence | SEQ ID NO | Sequence | SEQ ID NO | Sequence | SEQ ID NO | SEQ ID NO |
| B5 | DYAMS | 1 | SISSGSGSIYYADSVKG | 5 | NLIPLDY | 10 | 30 |
| C4I | GYYMS | 2 | LISPSSGSIYYADSVKG | 6 | GLTKFDY | 11 | 31 |
| D8G | SYSMS | 3 | GIYSDGSNTYYADSVKG | 7 | MLHRFDY | 12 | 32 |
| F6V | DYAMS | 1 | GISPGGSNTYYADSVKG | 8 | DAWIARLLLFDY | 13 | 33 |
| 10F11 | SYGMS | 4 | GIYSGGSSKYYADSVKG | 9 | NRLRFDY | 14 | 34 |

TABLE 4-continued

CDR Sequences of Heavy Chain Variable (VH)

| Clone | CDRH1 Sequence | SEQ ID NO | CDRH2 Sequence | SEQ ID NO | CDRH3 Sequence | SEQ ID NO | VH SEQ ID NO |
|---|---|---|---|---|---|---|---|
| D8G M1 | SYSMS | 3 | GIYSDASNTYYAD SVKG | 68 | MLHRFDY | 12 | 70 |
| D8G M3 | SYSMS | 3 | GIYSDASNTYYAD SVKG | 68 | MLHRFDY | 12 | 70 |

TABLE 5

CDR Sequences of Light Chain Variable (VL)

| Clone | CDRL1 Sequence | SEQ ID NO | CDRL2 Sequence | SEQ ID NO | CDRL3 Sequence | SEQ ID NO | VL SEQ ID NO |
|---|---|---|---|---|---|---|---|
| B5 | SGSSSNIGSNAVS | 15 | YNSHRPS | 20 | GSWDASLNAYV | 25 | 35 |
| C4I | TGSSSNIGSNDVS | 16 | ANSHRPS | 21 | GSWDDSLSGYV | 26 | 36 |
| D8G | SGSSSNIGSNSVT | 17 | ADSQRPS | 22 | GTWDSSLNAYV | 27 | 37 |
| F6V | SGSSSNIGSNAVT | 18 | YNNKRPS | 23 | GTWDDSLSGYV | 28 | 38 |
| 10F11 | TGSSSNIGSNSVT | 19 | SDSHRPS | 24 | GTWDASLNAYV | 29 | 39 |
| D8G M1 | SGSSSNIGSNSVT | 17 | ADSQRPS | 22 | GTWDSSLNAYV | 27 | 37 |
| D8G M3 | SGSSSNIGSNSVT | 17 | ADVQRPS | 69 | GTWDSSLNAYV | 27 | 71 |

The nucleic acid sequences encoding the variable regions and CDR sequences were comprised in the following full-length nucleic acid sequences in the order of B5, C41, D8G, F6V, 10F11, D8G M1, and D8G M3: SEQ ID NOs: 50 (heavy chain) and 55 (light chain); SEQ ID NOs: 51 (heavy chain) and 56 (light chain); SEQ ID NOs: 52 (heavy chain) and 57 (light chain); SEQ ID NOs: 53 (heavy chain) and 58 (light chain); SEQ ID NOs: 54 (heavy chain) and 59 (light chain); SEQ ID NOs: 74 (heavy chain) and 57 (light chain); and SEQ ID NOs: 74 (heavy chain) and 75 (light chain), respectively. In the nucleic acid sequences, the nucleic acid sequences encoding constant regions were SEQ ID NO: 61 to 63 (heavy chain), and SEQ ID NO: 65 to 67 (light chain).

Example 2: Conversion of Anti-B7-H3 scFv into Full IgG Form and Production Thereof

Example 2-1: Cloning of Anti-B7-H3 scFv into Full IgG Form

To convert each human B7-H3 specific monoclonal phage antibody, secured in Example 1, into a full IgG form, nucleic acids encoding heavy chain and light chain variable regions of each clone secured in Example 1 were synthesized (Genotech, Korea). Genes encoding human IgG1 subtype of heavy chain and light chain constant regions (SEQ ID Nos: 60 and 64, respectively) proteins (heavy chain constant regions SEQ ID NOs: 61 (C41, D8G, 10F11, D8G M1, D8G M3 clone), 62 (B5 clone), 63 (F6V clone) and light chain constant regions 65 (C41, D8G, 10F11, D8G M1, D8G M3 clone), 66 (B5 clone) and 67 (F6V clone)) were synthesized and were linked with the nucleic acid encoding each heavy chain and light chain variable region. The nucleic acids encoding light chain and heavy chain of each antibody were cloned in a pcDNA 3.1-based expression vector, respectively, and a vector encoding an antibody nucleic acid in a mammal cell line of CHO—S, etc. was secured. In addition, to use the conventional anti-B7-H3 antibody, Enoblituzumab as a comparison group antibody, the variable region sequence of the antibody was secured from the patent (U.S. Pat. No. 8,802,091) and the gene was secured, and it was cloned as same as the aforementioned method and named as 84D to use.

The IgG form of antibodies were disclosed as the following heavy chain and light chain full-length sequences in the order of B5, C41, D8G, F6V, 10F11, D8G M1, and D8G M3: SEQ ID NOs: 50 (heavy chain) and 55 (light chain); SEQ ID NOs: 51 (heavy chain) and 56 (light chain); SEQ ID NOs: 52 (heavy chain) and 57 (light chain); SEQ ID NOs: 53 (heavy chain) and 58 (light chain); SEQ ID NOs: 54 (heavy chain) and 59 (light chain); SEQ ID NOs: 74 (heavy chain) and 57 (light chain); and SEQ ID NOs: 74 (heavy chain) and 75 (light chain), respectively.

Example 2-2: Expression of Anti-B7-H3 Antibody

For expression of the anti-B7-H3 antibody, ExpiCHO-S™ (Thermo Fisher, A29127) cells developed by Theremo company were used, and the expression of the antibody was performed, following ExpiCHO™ Expression System Kit (Thermo Fisher, A29133) protocol of the manufacturer.

Briefly describing the preparation method, ExpiCHO-S cells were cultured under the condition of 120 rpm in a shaking incubator of 8% $CO^2$, 37° C. conditions. On the day of transfection, ExpiCHO-S cells were diluted by adding ExpiCHO™ Expression Medium (Thermo Fisher, A2910001) at a cell concentration of $6 \times 10^6$ cells/ml and prepared.

Then, each vector expressing the heavy chain and light chain from Example 2-1 was diluted in OptiPRO™ SFM medium (Thermo Fisher, 12309050), in 1 µg per medium ml, respectively, and 3.2 µl per ml of ExpiFectamine™CHO included in ExpiCHO Expression system was diluted in OptiPRO™ SFM medium. The vector and ExpiFectamine™CHO mixture were mixed each other and reacted at a room temperature for 5 min, and then the mixture was put into the prepared cells and it was cultured under the conditions of 8% $CO_2$, 37° C., 120 rpm for 20 hrs. In 20 hrs, after adding 2.2 µl/ml and 240 µl/ml of Enhencer1, ExpiCHO™ Feed, both included in ExpiCHO™ Expression System Kit (Thermo Fisher, A29133), were added to cells, respectively, it was cultured under the conditions of 8% $CO_2$, 37° C., 120 rpm for about 7 days to 10 days.

After culturing, the cell culture solution was centrifuged under the conditions of 4° C., 6000 rpm for 30 min, and then the supernatant was isolated and refrigerated.

Example 2-3: Separation and Purification of Anti-B7-H3 Antibody

After passing an equilibrium buffer solution (50 mM Tris-HCl, pH7.5, 100 mM NaCl) through Mab selectsure (GE healthcare, 5 ml) to equilibrate it, the culture solution of Example 2-2 through a column (Mab selectsure (GE healthcare, 5 ml)) in order to allow the expressed antibody to bind to the column. Then, after eluting it with a 50 mM Na-citrate (pH 3.4), 100 mM NaCl solution, it was neutralized by using 1M Tris-HCl (pH 9.0) so that the final pH was 7.2. The buffer solution was exchanged with PBS (phosphate buffered saline, pH 7.4).

Example 3: Analysis of Binding Specificity to B7-H3 of Anti-B7-H3 Antibody

Example 3-1: Analysis of Binding Specificity to Recombinant B7-H3 Antigen of Anti-B7-H3 IgG Antibody (ELISA)

To confirm the specific binding capacity to B7-H3 antigen of anti-B7-H3 IgG antibodies selected and prepared in Examples 1 and 2, ELISA-based solution binding test was performed.

Specifically, after diluting the recombinant human B7-H3 protein at a concentration of 1 µg/ml and putting it into a 96-well plate (Nunc-Immuno Plates, NUNC) in 100 µl per well, it was reacted at 4° C. for 16 hrs for coating. The recombinant human B7-H3 protein used in Example 1 was used here.

Then, after removing the protein and washing it with PBST, a PBS buffer comprising 1% BSA (bovine serum albumin) was put at 200 µl per well and it was reacted at 37° C. for 2 hrs to block non-specific binding. Then, after diluting anti-B7-H3 antibodies prepared in Example 2 at a concentration of 10 µg/ml on the 96-well plate, 100 µl was put in each well and it was reacted at 37° C. for 1 hr. Then after it was washed with PBST. In order to detect antibodies bound to human B7-H3, HRP-connected anti-human IgG F(ab')2 antibody (Goat anti-Human IgG F(ab')2 Cross-Adsorbed Secondary Antibody, HRP, Pierce, 31414) was diluted by 1:10,000 in PBS comprising 1% bovine serum albumin (BSA), and 100 µl was put per well and it was reacted at 37° C. for about 1 hr. After washing it with PBST again, TMB (Tetramethylbenzidine, Sigma, T0440) 100 µl was put to develop color. After reacting it at RT for 5-10 min, 50 µl of 1N $H_2SO_4$ was put to finish the reaction, and the absorbance at 450 nm and 650 nm was measured by using a micro plate reader (molecular device).

Figure 1A:
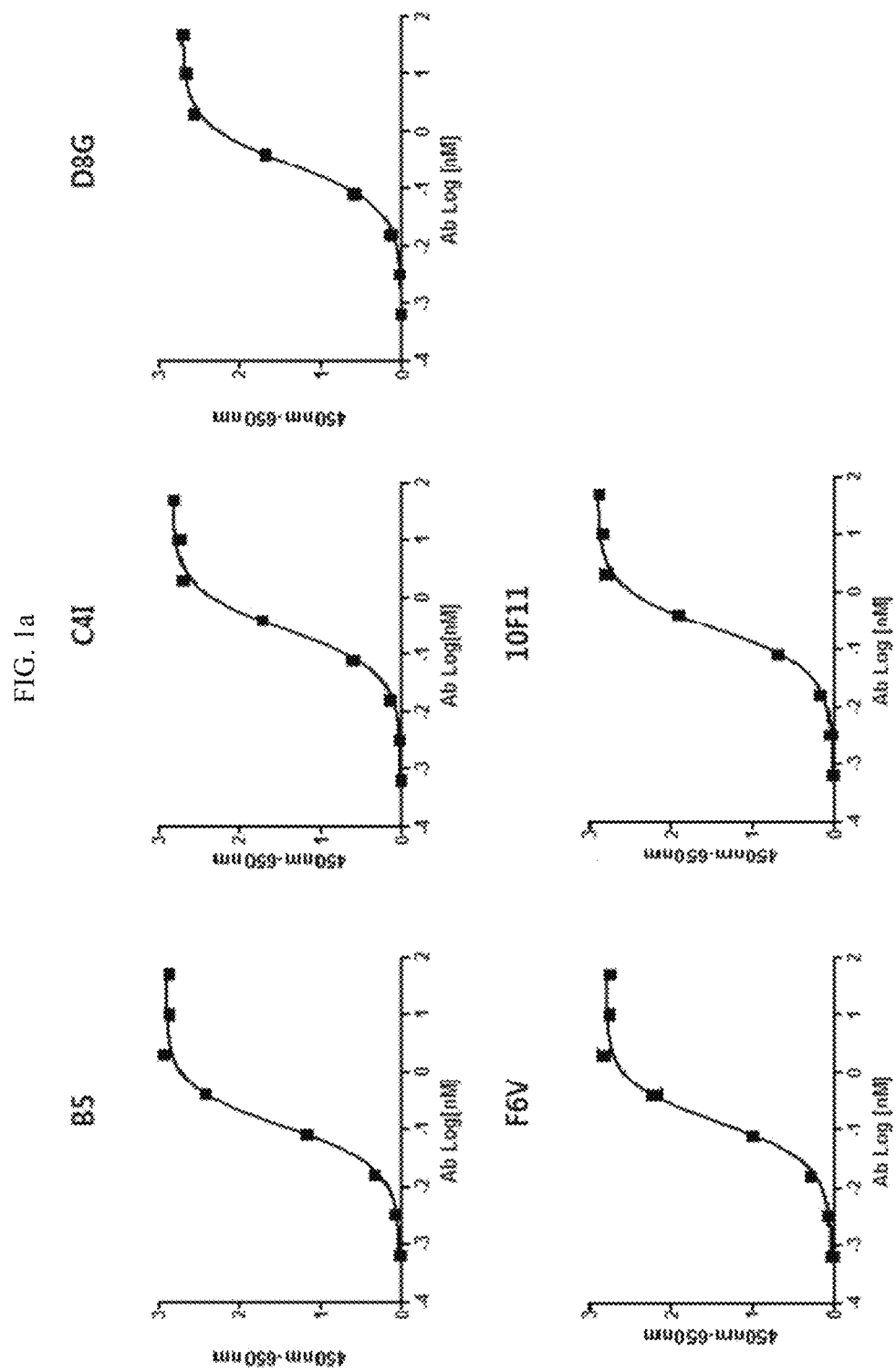
FIGS. 1a and 1b are the results of analysis (ELISA) of the binding capacity of the anti-B7-H3 antibody prepared according to one embodiment of the present invention to the extracellular domain (ECD) of B7-H3 protein. It was shown that every antibody bound to the extracellular domain of human B7-H3 protein in a concentration-dependent manner.
Figure 1B:
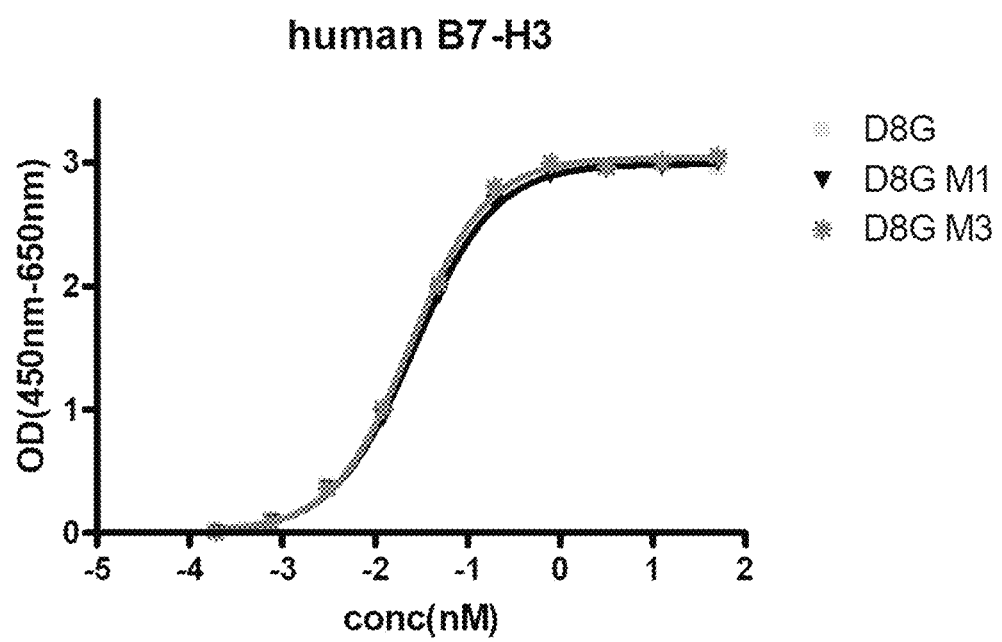

The result was described in FIGS. 1a and 1b. As the result of measuring the binding capacity using ELISA method, it was confirmed that anti-B7-H3 antibodies bound to an extracellular domain of human B7-H3 in a concentration-dependent manner.

Example 3-2: Analysis of Binding Capacity to Other Proteins of B7 Family of Anti-B7-H3 Antibody B7 family proteins share 20-40% of identical amino acids each other, and have structural relevance such as repeatability of immunoglobulin domain. Thus, it was analyzed whether the anti-B7-H3 antibodies of the present invention specifically bind to B7-H3 protein, not to other B7 family proteins, as follows.

To confirm immune specific binding capacity, B7 family component proteins having structural similarity: B7-1 (Sino Biological, Cat #: 10698-H08H), B7-2 (Sino Biological, Cat #: 10699-H08H), B7-DC(Sino Biological, Cat #: 10292-H08H), B7-H1 (Sino Biological, Cat #: 10084-H08H), B7-H2 (Sino Biological, Cat #: 11559-H08H), B7-H4 (Sino Biological, Cat #: 10738-H08H), B7-H5 (Sino Biological, Cat #: 13482-H08H), B7-H6 (Sino Biological, Cat #: 16140-H08H), B7-H7 (Sino Biological, Cat #: 16139-H02H) were purchased and used.

Specifically, after diluting the recombinant human B7 family proteins at a concentration of 1 µg/ml and putting them in a 96-well plate (Nunc-Immuno Plates, NUNC) in 100 µl per well, it was reacted at 4° C. for 16 hrs for coating. The recombinant proteins used in Example 1 was used.

Then, after removing proteins and washing it with PBST, 200 µl of PBS buffer comprising 1% BSA (bovine serum albumin) was put per well and it was reacted at 37° C. for 2 hrs to block non-specific binding. Then, after diluting the anti-B7-H3 antibodies prepared in Example 2 in 10 µg/ml on a 96-well plate, 100 µl was put per well and it was reacted at 37° C. for 1 hr. Then after it was washed with PBST. In order to detect antibodies bound to an antigen, HRP-connected anti-human IgG F(ab')2 antibody (Goat anti-Human IgG F(ab')2 Cross-Adsorbed Secondary Antibody, HRP, Pierce, 31414) was diluted in PBS comprising 1% bovine serum albumin (BSA) by 1:10,000. 100 µl was put per well and it was reacted at 37° C. for about 1 hr. After washing it with PBST again, TMB (Tetramethylbenzidine, Sigma, T0440) 100 µl was put to develop color. After reacting it at RT for 5-10 min, 50 µl of $H_2SO_4$ was put to finish the reaction, and the absorbance at 450 nm and 650 nm was measured by using a micro plate reader (molecular device).

Figure 2:
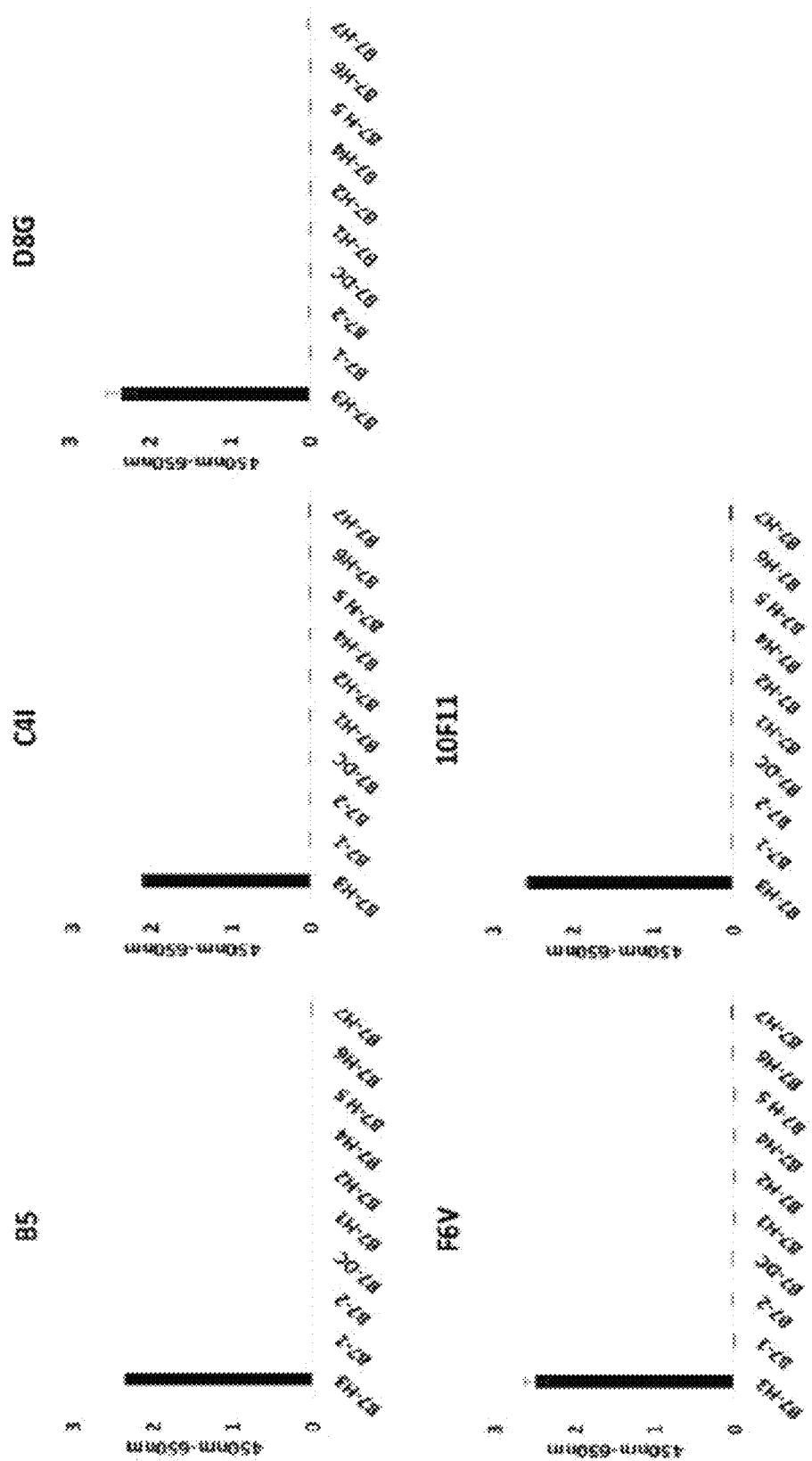
FIG. 2 is the result of analysis (ELISA) of the binding capacity of the anti-B7-H3 antibody prepared according to one embodiment of the present invention to ECD of the other proteins belonging to B7 family. It was shown that every antibody prepared according to one embodiment of the present invention did not bind to the other proteins and specifically recognized B7-H3 protein only.

The result was described in FIG. 2. As the result of measuring the binding capacity using ELISA method, it was confirmed that the anti-B7-H3 antibody specifically bound to B7-H3 only, not to the other B7 family proteins.

Example 3-3: Analysis of Intraspecific Cross-Reactivity to Human, Monkey and Mouse B7-H3 of Anti-B7-H3 Antibody To estimate the antibody efficacy and immune regulator activity of the anti-B7-H3 antibody before progressing clinical to human, estimation in rodents or primates model is important. The sequence of human B7-H3 shares 90% or more identity in monkey and mouse. The cross-reactivity to mouse or monkey B7-H3 of the anti-B7-H3 antibodies of the present invention prepared in Example 2 was analyzed by the ELISA analysis method as follows.

To confirm the intraspecific cross-reactivity, antigens of a recombinant mouse B7-H3 protein in which a histidine tag (His tag) was linked to the C terminal (Sino Biological, Cat #: 50973-M08H) and a recombinant monkey B7-H3 protein in which Fc region of human IgG1 was linked to the C terminal (Sino Biological, Cat #: 90806-C02H) were purchased and used.

After diluting the recombinant human B7-H3, mouse B7-H3 and monkey B7-H3 proteins in a concentration of 1 μg/ml and putting them in a 96-well plate (Nunc-Immuno Plates, NUNC) as 100 μl per well, it was reacted at 4° C. for 16 hrs and coated. For the used recombinant proteins, the product purchased for analysis in Example 1 was used.

Then, after removing proteins and washing it with PBST, 200 μl of PBS buffer comprising 1% BSA (bovine serum albumin) per well was put and it was reacted at 37° C. for 2 hrs to block non-specific binding. Then, after diluting the anti-B7-H3 antibodies prepared in Example 2 at certain concentrations ranging from 10 μg/ml on a 96-well plate, 100 μl was put per well and it was reacted at 37° C. for 1 hr. Then, after washing it with PBST, to detect antibodies bound to human B7-H3, mouse B7-H3 and monkey B7-H3, HRP-connected anti-human IgG F(ab')2 antibody (Goat anti-Human IgG F(ab')2 Cross-Adsorbed Secondary Antibody, HRP, Pierce, 31414) was diluted in PBS comprising 1% bovine serum albumin (BSA) by 1:10,000, and 100 μl was put per well and it was reacted at 37° C. for about 1 hr. After washing it with PBST again, TMB (Tetramethylbenzidine, Sigma, T0440) 100 μl was put to develop color. After reacting it at RT for 5-10 min, 50 μl of $H_2SO_4$ was put to finish the reaction, and the absorbance at 450 nm and 650 nm was measured by using a micro plate reader (molecular device).

Figure 3:
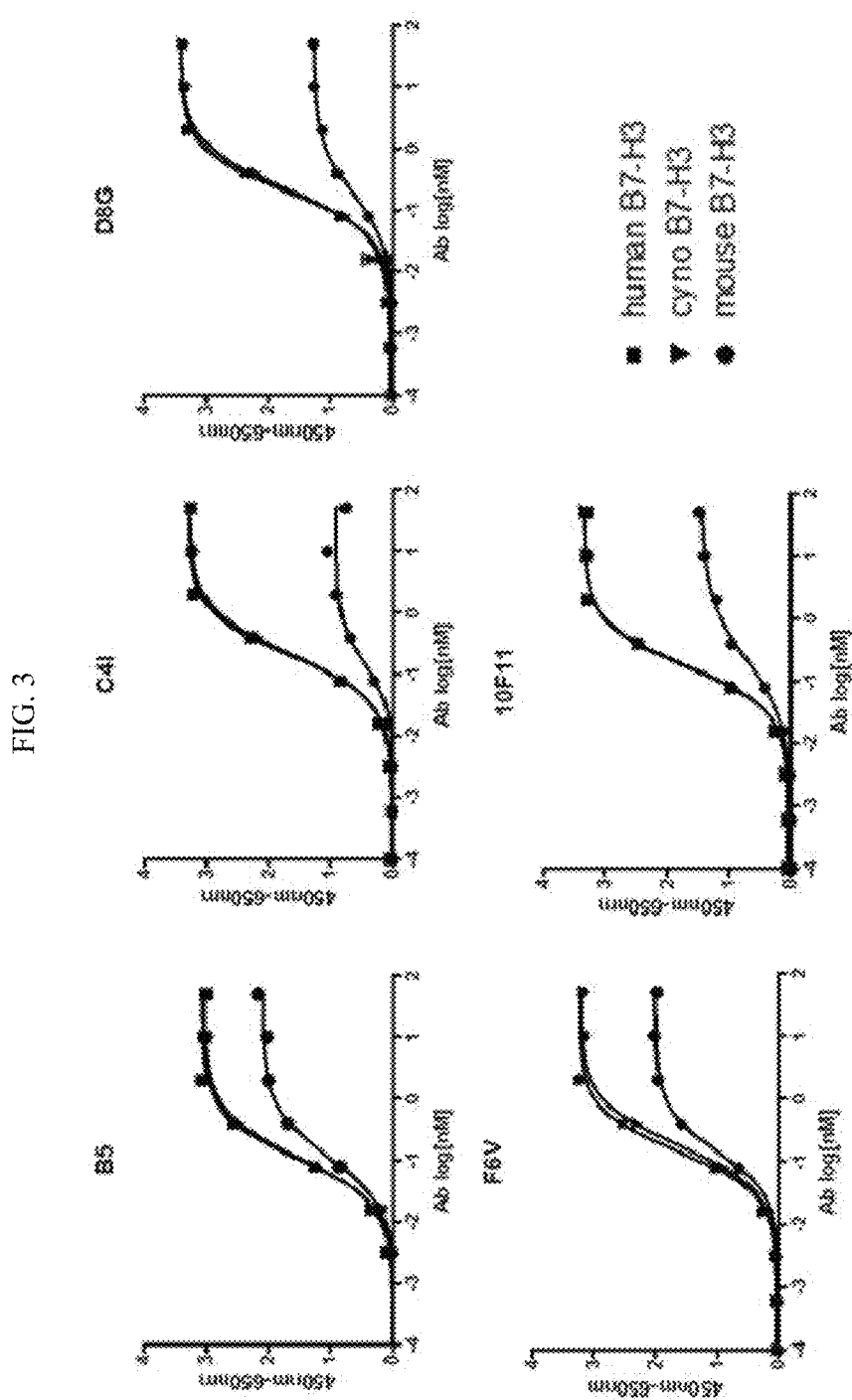
FIG. 3 is the result of analyzing intraspecific cross-reactivity of the anti-B7-H3 antibody prepared according to one embodiment of the present invention by ELISA. It was shown that every antibody bound to monkey (cynomolgus) B7-H3 and mouse B7-H3 in a concentration-dependent manner.
Figure 4:
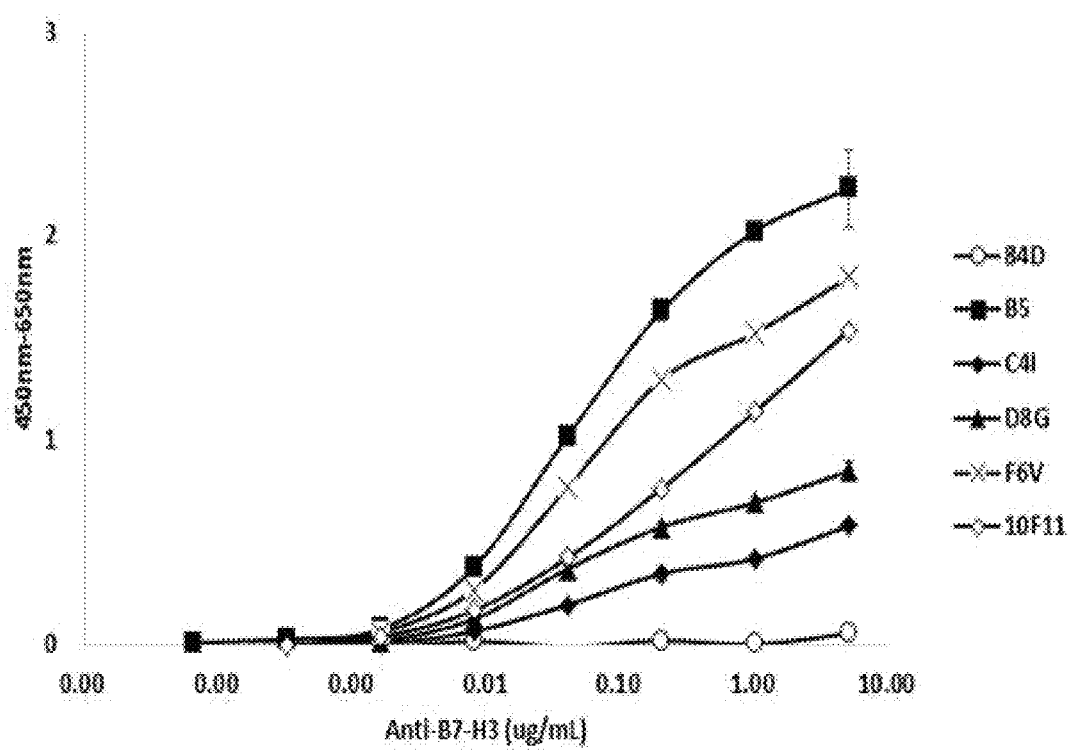
FIG. 4 is the result of comparing the binding capacity degree of various anti-B7-H3 antibodies prepared according to one embodiment of the present invention to mouse B7-H3 protein by ELISA. It was shown that the binding degree of antibodies to mouse B7-H3 are varied, but every antibody bound to mouse B7-H3 protein in a concentration-dependent manner. By Contrast, 84D antibody used as a comparison group antibody did not bind to mouse B7-H3 protein.

The result was described in FIG. 3 and FIG. 4. As the result of measuring the binding capacity using the ELISA method, it was confirmed that the anti-B7-H3 antibody specifically bound to human, monkey and mouse B7-H3s. The binding degrees of the anti-B7-H3 antibodies of the present invention to human and monkey B7-H3s were shown to be similar, but the binding degrees to mouse B7-H3 was relatively low (FIG. 3). It was observed that the binding degrees of the anti-B7-H3 antibodies to mouse B7-H3 were varying among the clones, and 84D antibody used as the comparison antibody did not bind to mouse B7-H3 protein (FIG. 4).

Example 3-4: Measurement of Binding Capacity to Cell Surface Expression B7-H3 Antigen of Anti-B7-H3 Antibody Then, through FACS analysis, the ability of the anti-B7-H3 antibody of the present invention prepared in Example 2 to bind to human B7-H3 expressed on a cell surface was measured.

For the experiment, the cancer cell lines expressing human B7-H3, MCF-7 (Human breast adenocarcinoma cell line, ATCC HTB-22™), DLD1 (colorectal adenocarcinoma cell lines, ATCC CCL-221™), HCC1954 (TNM stage IIA, grade 3, ductal carcinoma, ATCC CRL-2338™), and HCT116 (colon cancer cell, ATCC CCL-247™) and the cancer cell line, not expressing human B7-H3, Jurkat (acute T cell leukemia, ATCC TIB-152™) were used.

Specifically, after dissociating each cell line and washing it with PBS buffer, the number of cells was counted and adjusted to $2\times10^5$ cells per well, and prepared by putting 200 μl PBS. Each of anti-B7-H3 antibodies of Example 2 and comparison group antibody (84D) was reacted with the cells prepared in advance as diluted at a certain concentration of 10 μg/ml or more in PBS comprising 1% BSA, at 4° C. for 1 hr. After washing it twice using PBS buffer, the FITC-labeled anti-human Fc FITC (Goat anti-human IgG FITC conjugate, Fc specific, Sigma, F9512, concentration: 2.0 mg/ml) was diluted by 1:500 and treated in 100 μl per well, and it was reacted at 4° C. for 1 hr. The negative control group was treated with the FITC-labeled anti-human Fc FITC only. After washing it twice using PBS buffer again, the degree of binding of anti-BCMA IgG was measured using FACSCalibur device.

Figure 5:
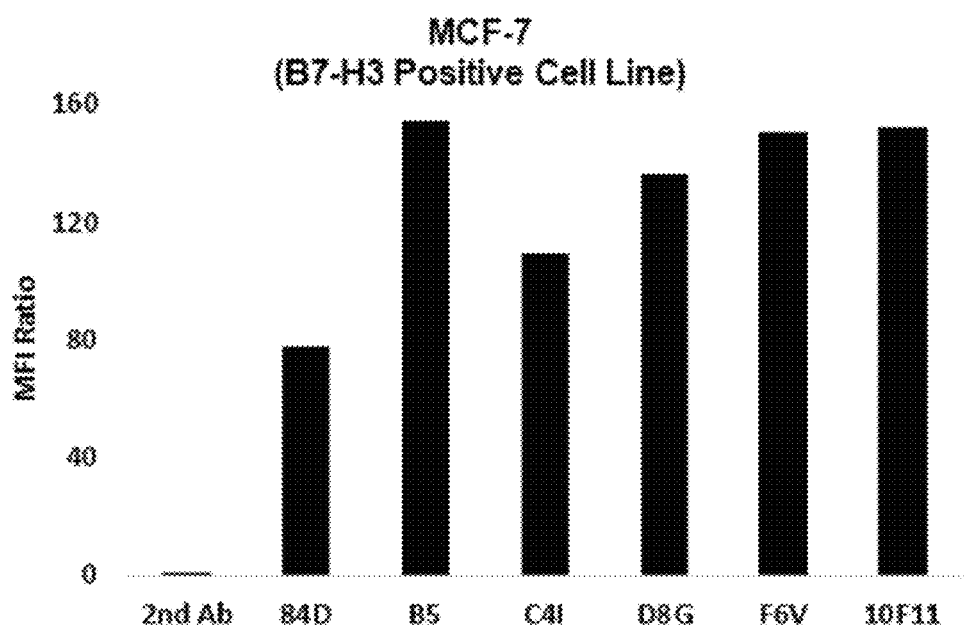
FIG. 5 is the result of measurement (FACS) for the binding capacity of the anti-B7-H3 antibody prepared according to one embodiment of the present invention to cell surface expression B7-H3 antigen. MCF-7 cell line is a cell line overexpressing B7-H3, and Jurkat is a cell line which does not express B7-H3. It was shown that the anti-B7-H3 antibodies of the present invention specifically bound to MCF-7, the cell line overexpressing B7-H3, but did not bind to Jurkat, the cell line which does not express B7-H3.
Figure 5:
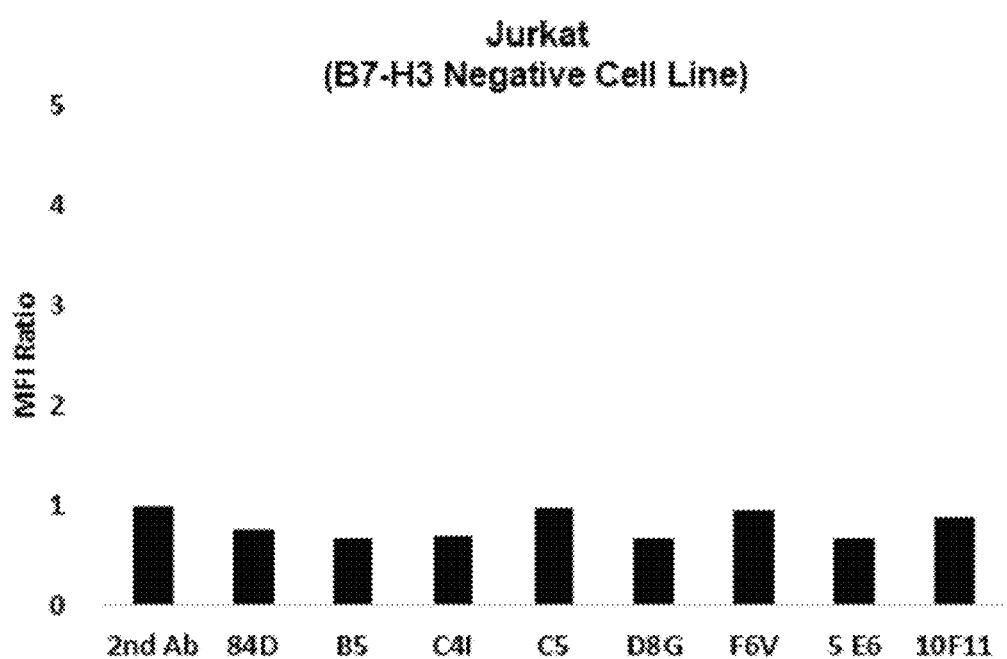
Figure 6:
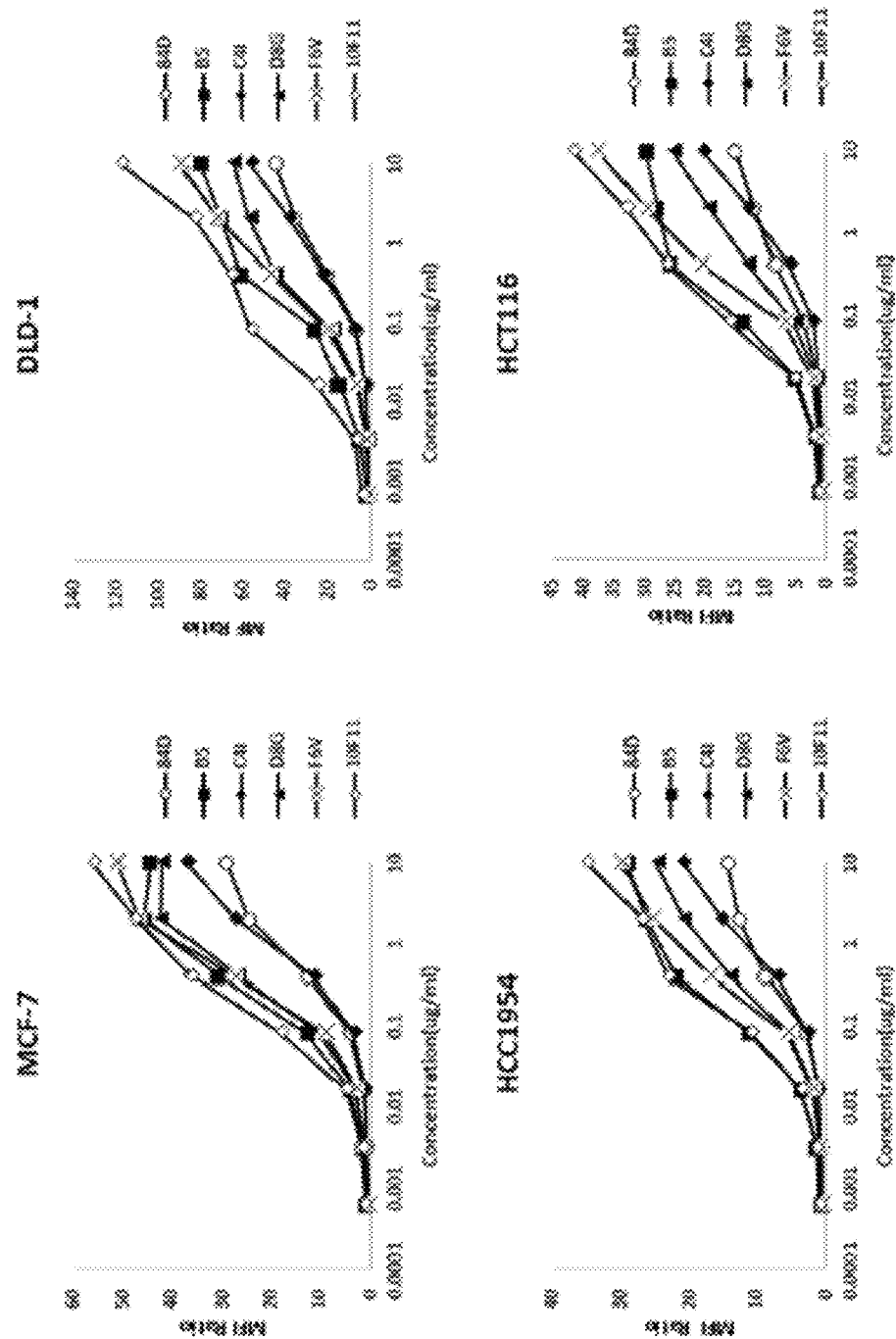
FIG. 6 is the result of measurement (FACS) for the binding capacity of the anti-B7-H3 antibody prepared according to one embodiment of the present invention to B7-H3 antigen expressed on the cell surface, for varying antibody concentrations. It was shown that every antibody bound to B7-H3 expressing cancer cell lines (MCF-7, DLD-1, HCC1954, and HCT116) in a concentration-dependent manner. The binding capacity of the antibodies to B7-H3 expressed in the other various cancer cell lines is described in Table 5.

The result of the peak shift for the human B7-H3-monoclonal antibody-FITC binding in experimental groups in which each B7-H3 monoclonal antibody was treated was compared to the negative control group binding. The result was represented by the value for the peak shift in the experimental groups treated with B7-H3 monoclonal antibody as divided by the value for the peak shift in the negative control group (Mean Fluorescence Intensity Ratio), and described in FIG. 5 and FIG. 6. As the result of measuring the binding capacity using FACS method, it was confirmed that the anti-B7-H3 antibody specifically binds to human B7-H3 expressed on a cell surface in a concentration-dependent manner.

Example 3-5: Measurement of Binding Capacity to Cell Surface Expression B7-H3 Antigen of Anti-B7-H3 IgG Antibody in Various Cancer Kinds Then, through FACS analysis, whether the anti-B7-H3 antibody of the present invention binds to cell surface expression B7-H3 in various kinds of cancer cell lines was confirmed.

Using various kinds of cancer cells A2780 (human ovarian cancer, ECACC, 93112519), SKOV-3 (human ovarian adenocarcinoma, ATCC® HTB-77™) OVCAR-3 (human ovarian adenocarcinoma, ATCC® HTB-161™), HCT116 (colon cancer cell, ThermoFIshcer Sci), HT29 (olorectal adenocarcinoma, ATCC® HTB-38™), DLD-1 (colorectal adenocarcinoma cell lines, ATCC® CCL-221™), Calu-6 (Non-small-cell lung carcinoma, ATCC® HTB-56™), HCC1954 (TNM stage IIA, grade 3, ductal carcinoma, ATCC® CRL-2338™), HCC1187 (TNM stage IIA, ATCC® CLC-2322™), renal cancer cell line 786-0 (renal cell adenocarcinoma, ATCC® CRL-1932™), A498 (kidney carcinoma, ATCC® HTB-44™), Panc-1 (pancreas epithelioid carcinoma, TCC CRL-1469™), NCI-N87 (gastric carcinoma, TCC CRL-5822™), HeLa (cervix adenocarcinoma, ATCC® CCL-2™), JeKo-1 (Lymphoma, ATCC® CRL-3006™) and FACSCalibur (BD Biosciences) device, the degree of binding of anti-B7-H3 antibody to B7-H3 was measured as follows.

After dissociating each cell line and washing it with PBS buffer, the number of cells was counted and adjusted to $2×10^5$ cells/200 µl PBS, and then was treated with 10 µg/ml of B7-H3 monoclonal antibodies prepared in Example 2. Reaction was allowed at 4° C. for 1 hr. After washing the reacted cells in PBS, the FITC-labeled constant region (Fc)-specific antibody (Goat anti-human IgG FITC conjugate, Fc specific, Sigma, F9512, concentration: 2.0 mg/ml)) was diluted by 1:500 and added 100 µl per well. and Reaction was allowed at 4° C. for 1 hr. After the reaction, cells were washed in PBS and analyzed using the FACSCalibur device. The negative control group was treated by the FITC-labeled constant region (Fc) specific antibody only. To compare expression degrees of B7-H3 among different cancer cell lines, the value for the peak shift in the experimental groups treated with the B7-H3 monoclonal antibody was divided by the value for the peak shift in the negative control group (MFI Ratio, Mean Fluorescence Intensity Ratio). The result was shown in Table 6.

TABLE 6

| Cancer Cell Line | | B5 | C4I | D8G | F6V | 10F11 | 84D |
|---|---|---|---|---|---|---|---|
| Ovarian Cancer | A2780 | 26.6 | 18.3 | 21.6 | 25.2 | 25.5 | 13.1 |
| | SKOV-3 | 29.5 | 20.4 | 23.3 | 27.7 | 28.5 | 11.9 |
| | OVCAR-3 | 33.1 | 22.4 | 26.7 | 33.1 | 35.6 | 13.7 |
| Colon Cancer | HCT116 | 11.9 | 6.8 | 7.9 | 10.8 | 12 | 5.9 |
| | HT29 | 17.6 | 12.7 | 11.9 | 15.9 | 18.7 | 8.9 |
| | DLD-1 | 24.9 | 14.9 | 18.5 | 25.6 | 24.6 | 10.7 |
| NSCLC | Calu-6 | 47.9 | 45.5 | 43.2 | N/D | 47.8 | 23.2 |
| TNBC | MDA-MB-231 | 11.4 | 6.2 | 8.5 | 11.3 | 12.4 | 5.4 |
| | MDA-MB-468 | 16.2 | 9.7 | 11.4 | 17.6 | 17.2 | 8.6 |
| Breast Cancer | MCF-7 | 154 | 109 | 136 | 151 | 152 | 78 |
| | HCC1954 | 29 | 21 | 25 | 30 | 35 | 14 |
| | HCC1187 | 21.8 | 11.2 | 13.3 | 18.4 | 22 | 14.9 |
| Kidney Cancer | 786-0 | 32 | 24 | 22 | 33 | 34 | 20 |
| | A-498 | 35 | 26 | 25 | 37 | 35 | 24 |
| Pancreatic Cancer | Panc-1 | 18 | 12 | 12 | 19 | 18 | 9 |
| Gastric Cancer | NCI-N87 | 27.3 | 17.6 | 21.5 | 33.4 | 31.7 | 12.8 |
| Cervical Cancer | Hela | 38.7 | 26.1 | 30.2 | 42.7 | 40.6 | 23.5 |
| MCL | JeKo-1 | 1.5 | 7.9 | 3.1 | N/D | 1.7 | 2.9 |

(MFI Ratio: MFI of anti-B7-H3/MFI of 2nd Ab)
(N/D: not determined)

As the result of measuring the binding capacity using FACS method, it was confirmed that the anti-B7-H-3 antibody of the present invention bound to various cancer cell lines derived from ovarian cancer, colorectal cancer, non-small cell lung cancer, breast cancer, renal cancer, pancreatic cancer, gastric cancer, cervical cancer and lymphoma. In addition, it was confirmed that the anti-B7-H-3 antibody of the present invention showed higher binding capacity compared to the antibody used as the comparison group, 84D, at the same concentration, and therefore the binding degree to the 1B7-H-3 expressed on a cell surface expression was superior.

Example 3-6: Measurement of Binding Capacity to Mouse B7-H3 Antigen of Mouse-Derived Cancer Cell of Anti-B7-H3 Antibody (FACS)

Then, through FACS analysis, the ability of binding to cell surface expression mouse B37-H-3 of the anti-B37-H-3 antibody of the present invention was measured. It was confirmed that the anti-B7-H-3 antibody bound to human B37-H-3 and mouse B37-H-3 recombinant proteins both through ELISA method in Example 3-3. To confirm whether the anti-B7-H3 antibody of the present invention binds to mouse B7-H3 expressed on a cell surface of a mouse cancer cell line, mouse-derived cancer cell lines, CT26 (Mus mesculus colon carcinoma, ATCC© CRL-2638™), B16F10 (Mus musculus skin melanoma, ATCC® CRL-6475™), TC-1 (Mus musulus Lung tumor, ATCC© CRL-2493™) were used.

For each cell line, cells were dissociated and washed with PBS buffer. The number of cells was counted and adjusted to $2×10^5$ cells per well. 200 µl PBS were added. The cells are prepared in a concentration of 10 µg/ml or more in 1% BSA-containing PBS. Each of the anti-B7-H3 antibodies prepared in Example 2 and comparison antibody (84D) was reacted with the above-prepared cells at 4° C. for 1 hr.

After washing the cells using PBS buffer, the FITC-labeled anti-human Fc FITC (Sigma, F9512) as diluted by 1:500 were added 100 µl per well, and reaction was allowed at 4° C. for 1 hr. For the control group, only the FITC-labeled anti-human Fc FITC was treated. After washing it twice using PBS buffer again, the degree of binding of the anti-B7-H3 IgG antibodies was measured using FACSCalibur device.

The value for the peak shift in the experimental groups treated with the B7-H3 monoclonal antibody was compared with the value for the peak shift in the negative control group. The result was described in FIG. 7. As the result of measurement using FACS method, it was confirmed that the anti-B7-H3 antibodies of the present invention specifically bound to mouse B7-H3 expressed on a cell surface.

Example 4: Measurement of Affinity to B7-H3 of Anti-B7-H3 Antibody

The binding affinity of antigen B7-H3 and anti-B7-H3 antibody was measured by SPR method. First, anti-B7-H3 antibody diluted by 1×HBS-EP buffer was captured with 50 RU on Protein A chip (GE healthcare, Cat. No. 29127556) at a contact time of 60 sec, a stabilization period of 60 sec and a flow rate of 30 µl/min. With 1×HBS-EP buffer, the antigen B7-H3 (R&D systems, 2318-B3-050/CF) was serially two-fold diluted starting from 100 nM to 3.125 nM. At this point, 1×HBS-EP buffer was additionally prepared as a blank. The B7-H3 antigen prepared on the chip in which the anti-B7-H3 antibody was captured was flowed at a flow rate of 30 µl/min for the association time of 60 sec and dissociation time of 180 sec. Regeneration was conducted with 10 mM Glycine-HCl pH1.5 (GE healthcare, Cat. No. BR100354) at a flow time of 30 µl/min and a contact time of 30 sec. The result was described in Table 7.

TABLE 7

Result of measurement of affinity to B7-H3 of anti-B7-H3 antibody

| Ab | Ka (1/Ms, ×10$^5$) | Kd (1/s, ×10$^{-3}$) | $K_D$ (M, ×10$^{-9}$) | $R_{max}$ (RU) | Chi$^2$ |
|---|---|---|---|---|---|
| 10F11 | 3.57 | 3.70 | 10.36 | 12.25 | 0.02 |
| B5 | 3.72 | 1.12 | 3.02 | 20.39 | 0.03 |
| C4I | 4.44 | 3.41 | 7.69 | 14.59 | 0.07 |
| D8G | 2.06 | 3.81 | 18.46 | 10.46 | 0.02 |
| F6V | 1.10 | 0.88 | 8.03 | 11.64 | 0.01 |

Example 5: Measurement of Antibody-Dependent Cell-Mediated Cytotoxicity of Anti-B7-H3 Antibody The ability of antibody-dependent cell-mediated cytotoxicity of the anti-B7-H3 antibody was confirmed by using ADCC Reporter Bioassay (Promega, G7018) kit. The experiment method was performed in accordance with the protocol of the manufacturer.

To analyze the ability of antibody-dependent cell-mediated cytotoxicity, MCF-7 breast cancer cell line, Calu-6 lung cancer cell line and DLD-1 colorectal cancer cell line as a cell line in which the expression degree of B7-H3 was relatively high, and Mino mantle cell lymphoma cell line as a cell line in which the expression degree of B7-H3 was relatively low were used. As a negative control group having no B7-H3 expression, Jurkat adult T cell leukemia cell line was used. Specifically, after dissociating an adherent culture cell lines, MCF-7, Calu-6 and DLD-1 cell lines one day before the experiment, and then centrifuging under the conditions of 4° C., 1200 rpm for 5 min, cells were suspended in RPMI 1640 medium comprising 10% fetal bovine serum (FBS) and $5 \times 10^3$ or $1 \times 10^4$ cells per well were inoculated and cultured. After removing the medium at the day of experiment and washing it with PBS, it was prepared by adding 25 µl of RPMI 1640 medium in which 4% of Low IgG Serum (Promega, AX20A) into cells. After centrifuging the suspension culture cell lines, Mino and Jurkat cell lines under the conditions of 4° C., 1200 rpm for 5 min, it was suspended in RPMI 1640 (4% Low IgG Serum) medium and $5 \times 10^3$ or $1 \times 10^4/25$ µl cells per well were inoculated on a 96 well plate.

After preparing the anti-B7-H3 antibody and comparison antibody (84D) of the present invention prepared in Example 2, by diluting them from the concentration of 10 pg/ml or 15 µg/ml or 18 µg/ml, respectively, at a certain ratio in RPMI 1640 (4% Low IgG Serum) medium, 25 µl per well was added. Then, after putting Jurkat/NFAT-FcγRIIIa cells comprised in ADCC reporter Bioassay into a 37° C. water bath and dissolving them, 3.6 mL of RPMI 1640 medium (4% Low IgG Serum) was added and mixed. After adding 25 µl of Jurkat/NFAT-FcγRIIIa cells per well, it was reacted at 37° C. for 6 hrs. Then, After dissolving substrates comprised in Bio-Glo luciferase assay (Promega, G7941) and adding 75 µl per well and reacting it for from 5 min to 10 min, the fluorescence was measured.

The antibody-dependent cell-mediated cytotoxicity effect of the anti-B7-H3 antibody was described in FIG. 8. It was confirmed that the antibody-dependent cell-mediated cytotoxicity was not observed in the negative control group not expressing B7-H3, Jurkat cell line, but the antibody-dependent cell-mediated cytotoxicity effect was shown specifically to the anti-B7-H3 antibody in MCF-7, Calu-6, DLD-1 and Mino cell lines expressing B7-H3. This shows that the antibody can be effectively used for death of cancer cells, since it induces the antibody-dependent cell-mediated cytotoxicity by specifically binding to cancer cells expressing B7-H3. In particular, it shows that the anti-B7-H3 antibody of the present invention can be more effectively used for cancer treatment, since the half maximal effective concentration (EC50) is low and the strength of antibody-dependent cell-mediated cytotoxicity signal is strong, compared to the comparison antibody, 84D.

Example 6: Measurement of Inducing Capacity of T Cell Activation of Anti-B7-H3 Antibody Example 6-1. Measurement of Inhibitory Effect of T Cell Activity by B7-H3 Protein in Human Peripheral Blood Mononuclear Cell (PBMC)

B7-H3 is a protein belonging to an immune checkpoint ligand, and it has been known to induce inhibition of immunoreaction of a T cell by binding to a B7-H3 receptor on a T cell surface. Thus, to confirm whether the release of cytokine (interferon gamma) by a T cell activated in advance is inhibited by a B7-H3 protein, the amount of release of cytokine of a human T cell was measured after a B7-H3 protein was treated on PBMC.

Specifically, to activate a human T cell, the anti-CD3 antibody (UCHT1, Biolegend) was prepared by diluting it in PBS to be 5 µg/ml, and the B7-H3 protein (Sino Biological, 11188-H08H) or a negative control group, IgG1 (BioXCell, BP0297, labeled as IgG1 or Cont. Ab) was added to the anti-CD3 antibody diluted in 5 µg/ml, thereby preparing it by progressing 4 times sequential dilution from 40 µg/ml. The anti-CD3 antibody and B7-H3 protein or the anti-CD3 antibody and negative control group prepared by diluting were aliquoted on a 96-well cell culture plate (Corning) in 50 µl/well and reacted at 4° C. overnight or at 37° C. for 2 hrs, and then it was washed with PBS once. The human peripheral blood mononuclear cell (CTL) prepared by purchasing was suspended in RPMI 1640 culture solution with 10% FBS (fetal bovine serum), and it was aliquoted as $1 \times 10^6$ cells/well on a plate coated by treating the anti-CD3 antibody and B7-H3 protein or the anti-CD3 antibody and negative control group and cultured. In 3 days after culturing, an experiment of analysis of interferon gamma release amount of a human T cell was progressed with ELISA analyzer (R&D system) according to instructions of the manufacturer of the analyzer using the culture supernatant. The result was described in FIG. 9a. As the result of measuring the interferon gamma release amount of a human T cell, it was confirmed that the activity of a T cell was inhibited by a B7-H3 protein and thereby the interferon gamma production was reduced.

Example 6-2. Measurement of T Cell Activation-Inducing Capacity of Anti-B7-H3 Antibody in Human Peripheral Blood Mononuclear Cell (PBMC)

Then an experiment was carried out, using a human peripheral blood mononuclear cell (PBMC), to investigate whether the anti-B7-H3 antibody could reactivate the activity of a T cell as inhibited by a B7-H3 protein. The anti-B7-H3 antibody which can block the binding between the B7-H3 protein and B7-H3 receptor on a T cell surface can reactivate immunoreaction of the T cell as inhibited by B7-H3. This means that the T cell activated as above can show an immune anti-cancer therapeutic effect.

An experiment was carried out to confirm whether the anti-B7-H3 antibody prepared in the present invention could block B7-H3's inhibition on the release of cytokine (interferon gamma) by the activated T cells.

PBMC was placed in a plate coated with the B7-H3 protein, then the plate was treated with the anti-B7-H3 antibody of the present invention. The measurement of release amount of cytokine of a human T cell was conducted.

To activate the human T cell, the anti-CD3 antibody (UCHT1, Biolegend) was prepared by diluting in PBS at 5 µg/ml, and for the inhibition of T cell activation by the B7-H3 protein, the B7-H3 protein was added at a concentration of 10 µg/ml to the prepared anti-CD3 antibody. The above prepared B7-H3 protein was aliquoted on a 96-well cell culture plate (Corning) with 50 µl per well and was reacted at 4° C. overnight or at 37° C. for 2 hrs, and then it was washed with PBS once. The anti-B7-H3 antibody and negative control group, IgG1 (BioXCell, BP0297, labeled as IgG1 or Cont. Ab) were added to RPMI-1640 culture solution (Invitrogen) with 10% FBS (fetal bovine serum), thereby preparing it by 4-fold sequential dilution starting from 16 μg/ml.

The human peripheral blood mononuclear cell (PBMC, CTL) prepared by purchasing was suspended in RPMI 1640 culture solution with 10% FBS (fetal bovine serum), and it was added in 1×10$^6$ cells/well on the plate coated with the anti-CD3 antibody and B7-H3 protein.

Onto the plate in which PBMC was placed, the anti-B7-H3 antibody and the negative control group IgG1 as prepared by serial 4-fold dilution were added (50 μl/well). Then, RPMI 1640 culture solution with 10% FBS was added by 100 μl per well so that the final concentration at the highest concentration in which the antibody was treated to a cell was 4 μg/ml (27 nM). In case in which the anti-B7-H3 antibody was treated at a single concentration, the final concentration of the antibody was 10 μg/ml. In 3 days after culturing, analysis of interferon gamma release amount of a human T cell was progressed with ELISA analyzer (R&D system) according to instructions of the manufacturer of the analyzer, using the culture supernatant.

The result was described in FIG. 9b. As the result of measuring the interferon gamma release amount of a human T cell, it was confirmed that the anti-B7-H3 antibody prepared in the present invention reactivated the T cell inhibited by the B7-H3 protein and thereby the interferon gamma production was facilitated. This result suggests that the anti-B7-H3 antibody of the present invention can be developed as an immune checkpoint inhibitor.

Example 6-3: Analysis of Co-Treatment Effect of Anti-B7-H3 Antibody and Immune Anti-Cancer Therapeutic Agent in Human Peripheral Blood Mononuclear Cell (PBMC)

Whether the release of cytokine (interferon gamma) by a T cell was increased by co-treatment of the anti-B7-H3 antibody and the immune anti-cancer therapeutic agent was investigated. An anti-PD-1 antibody was used by genetically synthesizing and producing Pembrolizumab of Merck company based on the sequence disclosed in WO2008-156712.

Specifically, anti-CD3 antibody (UCHT1, Biolegend) was diluted in PBS at 5 μg/ml, the B7-H3 protein was added to the prepared anti-CD3 antibody. The prepared B7-H3 protein as added to the anti-CD3 antibody was placed on a 96-well cell culture plate (Corning) in 50 μl per well and reacted at 4° C. overnight or at 37° C. for 2 hrs, and then it was washed with PBS once.

The anti-B7-H3 antibody of the present invention, a negative control group, IgG1 (BioXCell, BP0297, labeled as IgG1 or Cont. Ab), and the above prepared anti-PD-1 antibody were prepared by serial 4-fold dilution, with the addition of RPMI-1640 culture solution (Invitrogen) with 10% FBS (fetal bovine serum, Invitrogen).

The human peripheral blood mononuclear cell (CTL) prepared by purchasing was suspended in RPMI 1640 culture solution with 10% FBS (fetal bovine serum), and it was placed by 1×10$^6$ cells per well on a plate coated with the anti-CD3 antibody and B7-H3 protein.

Onto the plate in which PBMC was placed, the anti-B7-H3 antibody and the negative control group IgG1 as prepared by serial 4-fold dilution were added (50 pO/well). Then, RPMI 1640 culture solution with 10% FBS was added by 100 μl per well In case in which the anti-B7-H3 antibody was treated at a single concentration, the final concentration of the antibody was 10 μg/ml. In case in which the anti-B7-H3 antibody was treated at varying concentrations, serial 4-fold diluted concentrations were applied with the final concentration starting from the highest concentration of 20 nM. In 3 days after culturing, analysis of interferon gamma release amount of a human T cell was progressed with ELISA analyzer (R&D system) according to instructions of the manufacturer of the analyzer, using the culture supernatant.

The result was described in FIG. 10. As the result of measuring the release amount of interferon gamma of a human T cell, it was confirmed that the production of interferon gamma was more facilitated by activating the T cell strongly, when the anti-B7-H3 antibody was co-treated with the anti-PD-1 antibody, compared to single treatment of each antibody.

Example 7: Analysis of Anti-Cancer Efficacy by Co-Administration of Anti-B7-H3 Antibody and Anti-PD-1 Antibody in Mouse Isogenic Tumor Transplantation Model To confirm the efficacy of immune checkpoint inhibition of an antibody in an animal model, a mouse isogenic tumor transplantation model can be used when the antibody has intraspecific cross-reactivity between human and mouse.

As confirmed in Examples 3-3 and 3-6, the anti-B7-H3 antibody of the present invention has intraspecific cross-reactivity to a mouse B7-H3 antigen. The inhibition efficacy on tumor proliferation of the anti-B7-H3 antibody of the present invention was confirmed by co-treating it with the anti-mouse PD-1 antibody, RMP1-14 (BioXCell, BE0146) in a mouse isogenic tumor model as follows.

CT26 is a colon carcinoma derived from a mouse (BALB/c) and a cell line overexpressing a mouse B7-H3. It was confirmed that the anti-B7-H3 antibody prepared in Example 2 bound to the mouse B7-H3 expressed on the surface of CT26 mouse cancer cell line in Example 3-6 (FIG. 7).

To explain the experimental method in detail, after disassociating CT26 (BALB/c origin) cell line and washing it with PBS buffer, the number of cells was counted and adjusted to 5×10$^5$ cells per well. The prepared cells were administered by subcutaneous injection into a mouse (BALB/c, 6-week old, Samtako), and when the size of tumor was 50-100 mm$^3$, the antibodies were administered by 200 μg each, five times at a 3-day interval, a total of 1 mg. The respective tumor sizes for the control group, anti-PD-1 (RMP1-14) antibody single treatment group, and anti-PD-1 antibody and anti-B7-H3 antibody co-treatment group were calculated using a caliper by measuring the longest diameter of tumor (D1) and the diameter vertical to it (D2), to get the volume (0.5*D1*D2$^2$) (FIG. 11).

When the size of tumor was bigger than 2000 mm$^3$ or an ulcer was occurred during tumor observation, the corresponding mice were sacrificed. The survival rate and size of tumor were measured during a total of 30 day observation period after antibody administration was completed.

The result was shown in FIG. 11. As a result, compared to the group in which the anti-PD-1 (RMP1-14) antibody was treated alone, the tumor proliferation inhibition effect and enhancement of survival rate were confirmed in the group in which the anti-PD-1 and anti-B7-H3 antibody were co-administered. The result means that the anti-cancer therapeutic effect is intensified, when the anti-B7-H3 antibody of the present invention showing the immune checkpoint inhibitory efficacy and the anti-PD-1 antibody activating an immunocyte through a different mechanism as another immune inhibitor. As can be confirmed in Example 3-3, the binding capacity to mouse B7-H3 of the anti-B7-H3 antibody of the present invention is relatively low compared to human B7-H3. Despite of low binding capacity to mouse B7-H3, the anti-B7-H3 antibody of the present invention showed distinct cancer growth inhibition efficacy and enhancement of survival rate in co-administration with the anti-PD-1 antibody in an isogenic tumor transplantation model, compared to single administration of the anti-PD-1 antibody. The anti-B7-H3 antibody of the present invention is expected to have a stronger immune checkpoint inhibitory effect in human, by stronger binding to human B7-H3, than the result in the mouse isogenic tumor transplantation model.

Example 8: Analysis of Tumor-Infiltrating Lymphocyte (TIL) Change by Co-Administration of Anti-B7-H3 Antibody and Anti-PD-1 Antibody in Mouse Isogenic Tumor Transplantation Model Tumor-infiltrating lymphocytes (TIL) refer to white blood cells which leave bloodstream and move toward tumor. The tumor-infiltrating lymphocytes can comprise a T cell and a B cell, and include mononuclear and polymorphous nuclear immunocytes, are varying depending on the types and stages of tumor, and are related to disease prognosis. In particular, the mechanism of an immune anti-cancer antibody can be investigated through analysis of tumor-infiltrating lymphocytes.

To analyze an anti-cancer effect mechanism by co-administration (combi) of the anti-B7-H3 antibody (F6V) and the anti-PD-1 antibody (RMP-14-1), tumor-infiltrating lymphocytes were analyzed. The experiment was carried out by the same method as Example 8. The tumor was isolated from the mouse after 3 times of administration of each antibody was completed, to obtain the tumor-infiltrating lymphocytes.

The tumor infiltrating cells harvested were restimulated with PMA 50 ng/ml and Ionomycine 1 μM, and the changes in immunocytes were analyzed (FIG. 12). The representative immunocytes playing a major role of anti-cancer immunoreaction are a cytotoxic T cell and a regulatory T cell. As the result of experiment, in tumor-infiltrating lymphocytes isolated from the mouse in which the anti-B7-H3 antibody and the anti-PD-1 antibody of the present invention were co-administered, the activation of the cytotoxic T cell and proliferation inhibition of the regulatory T cell were clearly observed.

In the tumor-infiltrating lymphocytes isolated from the mouse in which the anti-B7-H3 antibody and anti-PD-1 antibody of the present invention were co-administered, the levels of IFNγ+Granzyme B+ among CD8+ T cells was significantly increased, and the increase in the release of Granzyme B among CD8+ T cells was observed.

In the tumor-infiltrating lymphocytes isolated from the mouse in which the anti-B7-H3 antibody and anti-PD-1 antibody of the present invention were co-administered, the frequency of regulatory T cell and the number of cells were confirmed by using an anti-Foxp3 antibody (eBioscience, FJK-16s), and the proliferative capacity of regulatory T cell was confirmed by using an anti-Ki67 (BD, B56) antibody.

The result was described in FIG. 12. As the result of experiment, it was confirmed that in the group in which the anti-B7-H3 antibody and anti-PD-1 were co-administered, not only the number of regulatory T cells was decreased, but also the Ki67+ frequency showing the proliferative capacity of the regulatory T cell was reduced. Such a result means that the co-administration of the anti-B7-H3 antibody and anti-PD-1 antibody induces increase of activity of the cytotoxic T cell and inhibition of the regulatory T cell at the same time, thereby showing an anti-cancer effect through immune activation.

The aforementioned description is intended to be illustrative, and those skilled in the art will understand that changes into other specific forms may be easily made, without modifying the technical spirit or necessary properties.

The invention claimed is:

1. An isolated antibody specifically recognizing B7-H3 or its antigen-binding fragment, wherein the antibody or antigen-binding fragment comprises (i) heavy chain complementarity determining regions of CDRH1, CDRH2 and CDRH3, and (ii) light chain complementarity determining regions of CDRL1, CDRL2 and CDRL3, and wherein, (a) the CDRH1, CDRH2 and CDRH3 are SEQ ID NOs: 1, 5, and 10, respectively, and the CDRL1, CDRL2, and CDRL3 are SEQ ID NOs: 15, 20 and 25, respectively;

(b) the CDRH1, CDRH2 and CDRH3 are SEQ ID NOs: 2, 6, and 11, respectively, and the CDRL1, CDRL2, and CDRL3 are SEQ ID NOs: 16, 21 and 26, respectively;

(c) the CDRH1, CDRH2 and CDRH3 are SEQ ID NOs: 3, 7, and 12, respectively, and the CDRL1, CDRL2, and CDRL3 are SEQ ID NOs: 17, 22 and 27, respectively;

(d) the CDRH1, CDRH2 and CDRH3 are SEQ ID NOs: 1, 8, and 13, respectively, and the CDRL1, CDRL2, and CDRL3 are SEQ ID NOs: 18, 23 and 28, respectively;

(e) the CDRH1, CDRH2 and CDRH3 are SEQ ID NOs: 4, 9, and 14, respectively, and the CDRL1, CDRL2, and CDRL3 are SEQ ID NOs: 19, 24 and 29, respectively (f) the CDRH1, CDRH2 and CDRH3 are SEQ ID NOs: 3, 68, and 12, respectively, and the CDRL1, CDRL2, and CDRL3 are SEQ ID NOs: 17, 22, and 27, respectively; or (g) the CDRH1, CDRH2 and CDRH3 are SEQ ID NOs: 3, 68, and 12, respectively, and the CDRL1, CDRL2, and CDRL3 are SEQ ID NOs: 17, 69, and 27, respectively.

2. The isolated antibody specifically recognizing B7-H3 or its antigen-binding fragment according to claim 1, comprising a combination of a heavy chain variable region and a light chain variable region, represented by the following sequence:

SEQ ID NOs: 30 and 35; SEQ ID NOs: 31 and 36; SEQ ID NOs: 32 and 37; SEQ ID NOs: 33 and 38; SEQ ID NOs: 34 and 39; SEQ ID NOs: 70 and 37; or SEQ ID NOs: 70 and 71.

3. The isolated antibody specifically recognizing B7-H3 or its antigen-binding fragment according to claim 1, comprising a combination of a heavy chain and a light chain, represented by the following sequence:

SEQ ID NOs: 50 and 55; SEQ ID NOs: 51 and 56; SEQ ID NOs: 52 and 57; SEQ ID NOs: 53 and 58; SEQ ID NOs: 54 and 59; SEQ ID NOs: 74 and 57; or SEQ ID NOs: 74 and 75.

4. The isolated antibody specifically recognizing B7-H3 or its antigen-binding fragment according to claim 1, wherein the antibody or antigen-binding fragment is a monoclonal antibody.

5. The isolated antibody specifically recognizing B7-H3 or its antigen-binding fragment according to claim 1, wherein the monoclonal antibody is an IgG1, IgG2, IgG3 or IgG4 type.

6. The isolated antibody specifically recognizing B7-H3 or its antigen-binding fragment according to claim 1, wherein the B7-H3 is B7-H3 of human, mouse or monkey.

7. The isolated antibody specifically recognizing B7-H3 or its antigen-binding fragment according to claim 1, wherein the antibody or antigen-binding fragment is Fab, Fab', F(ab')$_2$, scFab, Fv, dsFv, scFV, scFV-Fc, minibody, diabody, scAb, bivalent antibody or multivalent antibody.

8. An isolated polynucleotide encoding the antibody or its antigen-binding fragment according to claim 1.

9. A vector comprising a polynucleotide encoding the antibody or its antigen-binding fragment according to claim 1.

10. A cell line transformed with a vector comprising the polynucleotide encoding the antibody or its antigen-binding fragment according to claim 1.

11. A pharmaceutical composition, comprising the antibody or its antigen-binding fragment according to claim 1 and a pharmaceutically acceptable excipient.

12. A method for treating a disease related to overexpression of B7-H3, comprising a step of administering the antibody or its antigen-binding fragment according to claim 1 and a pharmaceutically acceptable excipient, to a subject in need thereof, wherein the disease related to overexpression of B7-H3 is cancer.

13. A method for diagnosing a disease related to overexpression of B7-H3, comprising a step of contacting the antibody or its antigen-binding fragment according to claim 1 with a biological sample, and a step of determining the biological sample or a patient from who the biological sample obtained as having a disease related to overexpression of B7-H3, when B7-H3 is present or the concentration of B7-H3 is increased in the biological sample as compared to a control group contacted with the antibody or its antigen-binding fragment, wherein the disease related to overexpression of B7-H3 is cancer.

14. The method according to claim 12, wherein the method comprises reactivating an activity of a T cell inhibited by a B7-H3 immune checkpoint.

* * * * *